United States Patent
Steines et al.

(10) Patent No.: US 9,495,483 B2
(45) Date of Patent: *Nov. 15, 2016

(54) AUTOMATED SYSTEMS FOR MANUFACTURING PATIENT-SPECIFIC ORTHOPEDIC IMPLANTS AND INSTRUMENTATION

(75) Inventors: Daniel Steines, Lexington, MA (US); Alexey Zhuravlev, Canton, MA (US); John Slamin, Wrentham, MA (US); Philipp Lang, Lexington, MA (US)

(73) Assignee: ConforMIS, Inc., Bedford, MA (US)

( * ) Notice: Subject to any disclaimer, the term of this patent is extended or adjusted under 35 U.S.C. 154(b) by 216 days.

This patent is subject to a terminal disclaimer.

(21) Appl. No.: 13/561,696

(22) Filed: Jul. 30, 2012

(65) Prior Publication Data

US 2013/0197870 A1    Aug. 1, 2013

Related U.S. Application Data

(63) Continuation of application No. 12/712,072, filed on Feb. 24, 2010, now Pat. No. 8,234,097, and a continuation-in-part of application No. 11/671,745, filed on Feb. 6, 2007, now Pat. No. 8,066,708, and a
(Continued)

(51) Int. Cl.
*G06F 17/50* (2006.01)
*A61F 2/30* (2006.01)
(Continued)

(52) U.S. Cl.
CPC ............ *G06F 17/50* (2013.01); *A61B 17/1675* (2013.01); *A61F 2/30942* (2013.01);
(Continued)

(58) Field of Classification Search
CPC .......... A61B 17/1675; A61B 17/1662; A61B 2017/00526; A61B 2019/508; A61F 2/30942; A61F 2/38; A61F 2002/30943; A61F 2002/30945; A61F 2002/30948; A61F 2002/30952; A61F 2002/3895; A61F 2002/30878; G06F 17/50
USPC ....... 606/86 R, 87–89; 703/1–3; 700/117, 98
See application file for complete search history.

(56) References Cited

U.S. PATENT DOCUMENTS 3,314,420 A   4/1967   Smith et al. ................... 128/92
3,605,123 A   9/1971   Hahn ................................ 3/1
(Continued)

FOREIGN PATENT DOCUMENTS

CN   86209787   11/1987   ............... A61F 2/38
CN   2305966    2/1999    ............... A61F 2/28
(Continued)

OTHER PUBLICATIONS

Adam et al., "NMR tomography of the cartilage structures of the knee joint with 3-D volume image combined with a rapid optical-imaging computer," ROFO Fortschr. Geb. Rontgenstr. Nuklearmed., 150(1): 44-48 (1989) Abstract Only.
(Continued)

*Primary Examiner* — Pedro Philogene
(74) *Attorney, Agent, or Firm* — Sunstein Kann Murphy & Timbers LLP

(57) ABSTRACT

Disclosed herein are devices, systems and methods for the automated design and manufacture of patient-specific/patient-matched orthopedic implants. While the embodiments described herein specifically pertain to unicompartmental resurfacing implants for the knee, the principles described are applicable to other types of knee implants (including, without limitation, other resurfacing implants and joint replacement implants) as well as implants for other joints and other patient-specific orthopedic applications.

28 Claims, 12 Drawing Sheets

Related U.S. Application Data continuation-in-part of application No. 11/002,573, filed on Dec. 2, 2004, now Pat. No. 7,534,263, which is a continuation-in-part of application No. 10/724,010, filed on Nov. 25, 2003, now Pat. No. 7,618,451, which is a continuation-in-part of application No. 10/305,652, filed on Nov. 27, 2002, now Pat. No. 7,468,075, which is a continuation-in-part of application No. 10/160,667, filed on May 28, 2002, said application No. 11/671,745 is a continuation-in-part of application No. 10/728,731, filed on Dec. 4, 2003, now Pat. No. 7,634,119, said application No. 11/671,745 is a continuation-in-part of application No. 10/681,750, filed on Oct. 7, 2003.

(60) Provisional application No. 61/208,440, filed on Feb. 24, 2009, provisional application No. 61/208,444, filed on Feb. 24, 2009, provisional application No. 60/765,592, filed on Feb. 6, 2006, provisional application No. 60/785,168, filed on Mar. 23, 2006, provisional application No. 60/788,339, filed on Mar. 31, 2006, provisional application No. 60/293,488, filed on May 25, 2001, provisional application No. 60/363,527, filed on Mar. 12, 2002, provisional application No. 60/380,695, filed on May 14, 2002, provisional application No. 60/380,692, filed on May 14, 2002, provisional application No. 60/431,176, filed on Dec. 4, 2002, provisional application No. 60/467,686, filed on May 2, 2003, provisional application No. 60/416,601, filed on Oct. 7, 2002.

(51) Int. Cl.
  *A61F 2/38* (2006.01)
  *A61B 17/16* (2006.01)
  *A61B 17/00* (2006.01)

(52) U.S. Cl.
  CPC ............ *A61F 2/38* (2013.01); *A61B 17/1662* (2013.01); *A61B 2017/00526* (2013.01); *A61B 2034/108* (2016.02); *A61F 2002/30878* (2013.01); *A61F 2002/30943* (2013.01); *A61F 2002/30945* (2013.01); *A61F 2002/30948* (2013.01); *A61F 2002/30952* (2013.01); *A61F 2002/3895* (2013.01)

(56) References Cited

U.S. PATENT DOCUMENTS

| | | | | |
|---|---|---|---|---|
| 3,694,820 | A | 10/1972 | Scales et al. | 3/1 |
| 3,798,679 | A | 3/1974 | Ewald | 3/1 |
| 3,808,606 | A | 5/1974 | Tronzo | 3/1 |
| 3,816,855 | A | 6/1974 | Saleh | 3/1 |
| 3,843,975 | A | 10/1974 | Tronzo | 3/1 |
| 3,852,830 | A | 12/1974 | Marmor | 3/1 |
| 3,855,638 | A | 12/1974 | Pilliar | 3/1 |
| 3,938,198 | A | 2/1976 | Kahn et al. | 3/1.912 |
| 3,982,281 | A | 9/1976 | Giliberty | 3/1.913 |
| 3,987,499 | A | 10/1976 | Scharbach et al. | 3/1.91 |
| 3,991,425 | A | 11/1976 | Martin et al. | 3/1.91 |
| 4,000,525 | A | 1/1977 | Klawitter et al. | 3/1.911 |
| 4,052,753 | A | 10/1977 | Dedo | 3/1 |
| 4,055,862 | A | 11/1977 | Farling | 3/1.91 |
| 4,085,466 | A | 4/1978 | Goodfellow et al. | 3/1.91 |
| 4,098,626 | A | 7/1978 | Graham et al. | 149/19.4 |
| 4,164,793 | A | 8/1979 | Swanson | 3/1.91 |
| 4,178,641 | A | 12/1979 | Grundei et al. | 3/1.911 |
| 4,203,444 | A | 5/1980 | Bonnell et al. | 128/276 |
| 4,207,627 | A | 6/1980 | Cloutier | 3/1.911 |
| 4,211,228 | A | 7/1980 | Cloutier | 128/303 R |
| 4,213,816 | A | 7/1980 | Morris | 156/245 |
| 4,219,893 | A | 9/1980 | Noiles | 3/1.911 |
| 4,280,231 | A | 7/1981 | Swanson | 3/1.91 |
| 4,309,778 | A | 1/1982 | Buechel et al. | 3/1.911 |
| 4,340,978 | A | 7/1982 | Buechel et al. | 3/1.911 |
| 4,344,193 | A | 8/1982 | Kenny | 3/1.911 |
| 4,368,040 | A | 1/1983 | Weissman | 433/36 |
| 4,436,684 | A | 3/1984 | White | 264/138 |
| 4,459,985 | A | 7/1984 | McKay et al. | 128/303 R |
| 4,502,161 | A | 3/1985 | Wall | 3/1.91 |
| 4,575,805 | A | 3/1986 | Moermann et al. | 364/474 |
| 4,586,496 | A | 5/1986 | Keller | 128/92 E |
| 4,594,380 | A | 6/1986 | Chapin et al. | 524/144 |
| 4,601,290 | A | 7/1986 | Effron et al. | 128/305 |
| 4,609,551 | A | 9/1986 | Caplan et al. | 424/95 |
| 4,627,853 | A | 12/1986 | Campbell et al. | 623/16 |
| 4,655,227 | A | 4/1987 | Gracovetsky | 128/781 |
| 4,662,889 | A | 5/1987 | Zichner et al. | 623/20 |
| 4,699,156 | A | 10/1987 | Gracovetsky | 128/781 |
| 4,714,472 | A | 12/1987 | Averill et al. | 623/20 |
| 4,714,474 | A | 12/1987 | Brooks, Jr. et al. | 623/20 |
| 4,769,040 | A | 9/1988 | Wevers | 623/20 |
| 4,813,436 | A | 3/1989 | Au | 128/779 |
| 4,822,365 | A | 4/1989 | Walker et al. | 623/20 |
| 4,823,807 | A | 4/1989 | Russell et al. | 128/773 |
| 4,841,975 | A | 6/1989 | Woolson | 128/653 |
| 4,846,835 | A | 7/1989 | Grande | 623/11 |
| 4,865,607 | A | 9/1989 | Witzel et al. | 623/20 |
| 4,872,452 | A | 10/1989 | Alexson | 128/92 VJ |
| 4,880,429 | A | 11/1989 | Stone | 623/18 |
| 4,883,488 | A | 11/1989 | Bloebaum et al. | |
| 4,888,021 | A | 12/1989 | Forte et al. | 623/20 |
| 4,936,853 | A | 6/1990 | Fabian et al. | 623/20 |
| 4,936,862 | A | 6/1990 | Walker et al. | 623/23 |
| 4,944,757 | A | 7/1990 | Martinez et al. | 623/20 |
| 4,979,949 | A | 12/1990 | Matsen, III et al. | 606/53 |
| 5,007,936 | A | 4/1991 | Woolson | 623/23 |
| 5,019,103 | A | 5/1991 | Van Zile et al. | 623/20 |
| 5,021,061 | A | 6/1991 | Wevers et al. | 623/20 |
| 5,041,138 | A | 8/1991 | Vacanti et al. | 623/16 |
| 5,047,057 | A | 9/1991 | Lawes | 623/20 |
| 5,059,216 | A | 10/1991 | Winters | 623/20 |
| 5,067,964 | A | 11/1991 | Richmond et al. | 623/18 |
| 5,099,859 | A | 3/1992 | Bell | 128/781 |
| 5,108,452 | A | 4/1992 | Fallin | 623/23 |
| 5,123,927 | A | 6/1992 | Duncan et al. | 623/20 |
| 5,129,908 | A | 7/1992 | Peterson | 606/88 |
| 5,133,759 | A | 7/1992 | Turner | 623/20 |
| 5,150,304 | A | 9/1992 | Berchem et al. | 364/474.24 |
| 5,152,797 | A | 10/1992 | Luckman et al. | 623/20 |
| 5,154,178 | A | 10/1992 | Shah | 128/653.2 |
| 5,162,430 | A | 11/1992 | Rhee et al. | 525/54.1 |
| 5,171,244 | A | 12/1992 | Caspari et al. | 606/88 |
| 5,171,322 | A | 12/1992 | Kenny | 623/18 |
| 5,192,283 | A | 3/1993 | Ling et al. | 606/93 |
| 5,197,985 | A | 3/1993 | Caplan et al. | 623/16 |
| 5,206,023 | A | 4/1993 | Hunziker | 424/423 |
| 5,226,914 | A | 7/1993 | Caplan et al. | 623/16 |
| 5,234,433 | A | 8/1993 | Bert et al. | 606/88 |
| 5,236,461 | A | 8/1993 | Forte | 623/20 |
| 5,245,282 | A | 9/1993 | Mugler, III et al. | 324/309 |
| 5,246,013 | A | 9/1993 | Frank et al. | 128/774 |
| 5,246,530 | A | 9/1993 | Bugle et al. | 156/643 |
| 5,258,032 | A | 11/1993 | Bertin | 623/20 |
| 5,270,300 | A | 12/1993 | Hunziker | 514/12 |
| 5,274,565 | A | 12/1993 | Reuben | 364/474.24 |
| 5,282,868 | A | 2/1994 | Bahler | 623/20 |
| 5,288,797 | A | 2/1994 | Khalil et al. | 524/872 |
| 5,299,288 | A | 3/1994 | Glassman et al. | 395/80 |
| 5,303,148 | A | 4/1994 | Mattson et al. | 364/413.01 |
| 5,306,307 | A | 4/1994 | Senter et al. | 623/17 |
| 5,306,311 | A | 4/1994 | Stone et al. | 623/18 |
| 5,314,478 | A | 5/1994 | Oka et al. | 623/18 |
| 5,314,482 | A | 5/1994 | Goodfellow et al. | 623/20 |
| 5,320,102 | A | 6/1994 | Paul et al. | 128/653.2 |
| 5,326,363 | A | 7/1994 | Aikins | 623/20 |
| 5,326,365 | A | 7/1994 | Alvine | 623/21 |
| 5,336,266 | A | 8/1994 | Caspari et al. | 623/20 |
| 5,344,459 | A | 9/1994 | Swartz | 623/18 |
| 5,360,446 | A | 11/1994 | Kennedy | 623/16 |

(56) References Cited

U.S. PATENT DOCUMENTS

| | | | |
|---|---|---|---|
| 5,365,996 A | 11/1994 | Crook | 164/45 |
| 5,368,858 A | 11/1994 | Hunziker | 424/423 |
| 5,403,319 A | 4/1995 | Matsen, III et al. | 606/88 |
| 5,405,395 A | 4/1995 | Coates | 623/20 |
| 5,413,116 A | 5/1995 | Radke et al. | 128/777 |
| 5,423,828 A | 6/1995 | Benson | 606/102 |
| 5,433,215 A | 7/1995 | Athanasiou et al. | 128/774 |
| 5,445,152 A | 8/1995 | Bell et al. | 128/653.5 |
| 5,448,489 A | 9/1995 | Reuben | 364/474.05 |
| 5,452,407 A | 9/1995 | Crook | 395/121 |
| 5,468,787 A | 11/1995 | Braden et al. | 523/113 |
| 5,478,739 A | 12/1995 | Slivka et al. | 435/240.23 |
| 5,489,309 A | 2/1996 | Lackey et al. | 623/19 |
| 5,501,687 A | 3/1996 | Willert et al. | 606/94 |
| 5,503,162 A | 4/1996 | Athanasiou et al. | 128/774 |
| 5,507,820 A | 4/1996 | Pappas | 623/20 |
| 5,510,121 A | 4/1996 | Rhee et al. | 424/520 |
| 5,522,900 A | 6/1996 | Hollister | 623/18 |
| 5,523,843 A | 6/1996 | Yamane et al. | 356/363 |
| 5,541,515 A | 7/1996 | Tsujita | 324/318 |
| 5,549,690 A | 8/1996 | Hollister et al. | 623/21 |
| 5,554,190 A | 9/1996 | Draenert | 623/16 |
| 5,556,432 A | 9/1996 | Kubein-Meesenburg et al. | 623/20 |
| 5,560,096 A | 10/1996 | Stephens | 29/558 |
| 5,564,437 A | 10/1996 | Bainville et al. | 128/774 |
| 5,571,191 A | 11/1996 | Fitz | 623/17 |
| 5,571,205 A | 11/1996 | James | 623/24 |
| 5,609,640 A | 3/1997 | Johnson | 623/20 |
| 5,611,802 A | 3/1997 | Samuelson et al. | 606/86 |
| 5,616,146 A | 4/1997 | Murray | 606/80 |
| 5,632,745 A | 5/1997 | Schwartz | 606/75 |
| 5,671,741 A | 9/1997 | Lang et al. | 128/653.2 |
| 5,681,354 A | 10/1997 | Eckhoff | 623/20 |
| 5,682,886 A | 11/1997 | Delp et al. | 128/653.1 |
| 5,683,466 A | 11/1997 | Vitale | 623/18 |
| 5,683,468 A | 11/1997 | Pappas | 623/20 |
| 5,684,562 A | 11/1997 | Fujieda | 351/212 |
| 5,687,210 A | 11/1997 | Maitrejean et al. | 378/57 |
| 5,690,635 A | 11/1997 | Matsen, III et al. | 606/88 |
| 5,702,463 A | 12/1997 | Pothier et al. | 623/20 |
| 5,723,331 A | 3/1998 | Tubo et al. | 435/366 |
| 5,728,162 A | 3/1998 | Eckhoff | 623/20 |
| 5,735,277 A | 4/1998 | Schuster | 128/653.1 |
| 5,737,506 A | 4/1998 | McKenna et al. | 395/125 |
| 5,741,215 A | 4/1998 | D'Urso | 600/407 |
| 5,743,918 A | 4/1998 | Calandruccio et al. | 623/21 |
| 5,749,362 A | 5/1998 | Funda et al. | 128/653.1 |
| 5,749,874 A | 5/1998 | Schwartz | 606/75 |
| 5,749,876 A | 5/1998 | Duvillier et al. | 606/88 |
| 5,759,205 A | 6/1998 | Valentini | 623/16 |
| 5,762,125 A | 6/1998 | Mastrorio | 164/4.1 |
| 5,768,134 A | 6/1998 | Swaelens et al. | 364/468.28 |
| 5,769,092 A | 6/1998 | Williamson, Jr. | 128/898 |
| 5,769,899 A | 6/1998 | Schwartz et al. | 623/18 |
| 5,772,595 A | 6/1998 | Votruba et al. | 600/415 |
| 5,779,651 A | 7/1998 | Buschmann et al. | 600/587 |
| 5,786,217 A | 7/1998 | Tubo et al. | 435/402 |
| 5,810,006 A | 9/1998 | Votruba et al. | 128/653.2 |
| 5,824,085 A | 10/1998 | Sahay et al. | 623/16 |
| 5,824,102 A | 10/1998 | Buscayret | 623/20 |
| 5,827,289 A | 10/1998 | Reiley et al. | 606/86 |
| 5,832,422 A | 11/1998 | Wiedenhoefer | 702/154 |
| 5,835,619 A | 11/1998 | Morimoto et al. | 382/132 |
| 5,842,477 A | 12/1998 | Naughton et al. | 128/898 |
| 5,847,804 A | 12/1998 | Sarver et al. | 351/206 |
| 5,853,746 A | 12/1998 | Hunziker | 424/426 |
| 5,871,018 A | 2/1999 | Delp et al. | 128/898 |
| 5,871,540 A | 2/1999 | Weissman et al. | 623/20 |
| 5,871,542 A | 2/1999 | Goodfellow et al. | 623/20 |
| 5,871,546 A | 2/1999 | Colleran et al. | 623/20 |
| 5,879,390 A | 3/1999 | Kubein-Meesenburg et al. | 623/20 |
| 5,880,976 A | 3/1999 | DiGioia III et al. | 364/578 |
| 5,885,296 A | 3/1999 | Masini | 606/86 |
| 5,885,298 A | 3/1999 | Herrington et al. | 606/88 |
| 5,897,559 A | 4/1999 | Masini | 606/86 |
| 5,899,859 A | 5/1999 | Votruba et al. | 600/415 |
| 5,900,245 A | 5/1999 | Sawhney et al. | 424/426 |
| 5,906,643 A | 5/1999 | Walker | 623/20 |
| 5,906,934 A | 5/1999 | Grande et al. | 435/325 |
| 5,913,821 A | 6/1999 | Farese et al. | 600/425 |
| 5,916,220 A | 6/1999 | Masini | 606/88 |
| 5,928,945 A | 7/1999 | Seliktar et al. | 435/395 |
| 5,939,323 A | 8/1999 | Valentini et al. | 435/395 |
| 5,961,523 A | 10/1999 | Masini | 606/86 |
| 5,968,051 A | 10/1999 | Luckman et al. | 606/88 |
| 5,968,099 A | 10/1999 | Badorf et al. | 623/20 |
| 5,972,385 A | 10/1999 | Liu et al. | 424/486 |
| 5,995,738 A | 11/1999 | DiGioia, III et al. | 395/500.32 |
| 5,997,577 A | 12/1999 | Herrington et al. | 623/20 |
| 6,002,859 A * | 12/1999 | DiGioia et al. | 703/11 |
| 6,013,103 A | 1/2000 | Kaufman et al. | 623/20 |
| 6,046,379 A | 4/2000 | Stone et al. | 623/11 |
| 6,057,927 A | 5/2000 | Lévesque et al. | 356/432 T |
| 6,078,680 A | 6/2000 | Yoshida et al. | 382/128 |
| 6,081,577 A | 6/2000 | Webber | 378/23 |
| 6,082,364 A | 7/2000 | Balian et al. | 128/898 |
| 6,090,144 A | 7/2000 | Letot et al. | 623/20 |
| 6,093,204 A | 7/2000 | Stone | 623/14.12 |
| 6,102,916 A | 8/2000 | Masini | 606/88 |
| 6,102,955 A | 8/2000 | Mendes et al. | 623/20 |
| 6,110,209 A | 8/2000 | Stone | 623/16.11 |
| 6,112,109 A | 8/2000 | D'Urso | 600/407 |
| 6,120,541 A | 9/2000 | Johnson | 623/14.12 |
| 6,120,543 A | 9/2000 | Kubein-Meesenburg et al. | 623/20 |
| 6,126,690 A | 10/2000 | Ateshian et al. | 623/18 |
| 6,132,468 A | 10/2000 | Mansmann | 623/20.16 |
| 6,139,578 A | 10/2000 | Lee et al. | 623/16.11 |
| 6,146,422 A | 11/2000 | Lawson | 623/17.16 |
| 6,151,521 A | 11/2000 | Guo et al. | 600/407 |
| 6,152,960 A | 11/2000 | Pappas | 623/20.31 |
| 6,156,069 A | 12/2000 | Amstutz | 623/22.11 |
| 6,161,080 A * | 12/2000 | Aouni-Ateshian et al. | 703/11 |
| 6,162,208 A | 12/2000 | Hipps | 606/1 |
| 6,165,221 A | 12/2000 | Schmotzer | 623/20.11 |
| 6,171,340 B1 | 1/2001 | McDowell | 623/18.11 |
| 6,175,655 B1 | 1/2001 | George, III et al. | 382/257 |
| 6,178,225 B1 | 1/2001 | Zur et al. | 378/98.2 |
| 6,187,010 B1 | 2/2001 | Masini | 606/86 |
| 6,197,064 B1 | 3/2001 | Haines et al. | 623/20.31 |
| 6,197,325 B1 | 3/2001 | MacPhee et al. | 424/426 |
| 6,200,606 B1 | 3/2001 | Peterson et al. | 424/574 |
| 6,203,576 B1 | 3/2001 | Afriat et al. | 623/20.27 |
| 6,205,411 B1 * | 3/2001 | DiGioia et al. | 703/11 |
| 6,206,927 B1 | 3/2001 | Fell et al. | 623/20.29 |
| 6,214,369 B1 | 4/2001 | Grande et al. | 424/423 |
| 6,217,894 B1 | 4/2001 | Sawhney et al. | 424/426 |
| 6,219,571 B1 | 4/2001 | Hargreaves et al. | 600/410 |
| 6,224,632 B1 | 5/2001 | Pappas et al. | 623/20.34 |
| 6,235,060 B1 | 5/2001 | Kubein-Meesenburg et al. | 623/20.31 |
| 6,249,692 B1 | 6/2001 | Cowin | 600/407 |
| 6,251,143 B1 | 6/2001 | Schwartz et al. | 623/23.72 |
| 6,254,639 B1 | 7/2001 | Peckitt | 623/11.11 |
| 6,261,296 B1 | 7/2001 | Aebi et al. | 606/90 |
| 6,277,151 B1 | 8/2001 | Lee et al. | 623/23.61 |
| 6,281,195 B1 | 8/2001 | Rueger et al. | 514/21 |
| 6,283,980 B1 | 9/2001 | Vibe-Hansen et al. | 606/151 |
| 6,289,115 B1 | 9/2001 | Takeo | 382/130 |
| 6,289,753 B1 | 9/2001 | Basser et al. | 73/866 |
| 6,299,645 B1 | 10/2001 | Ogden | 623/20.21 |
| 6,299,905 B1 | 10/2001 | Peterson et al. | 424/486 |
| 6,302,582 B1 | 10/2001 | Nord et al. | 378/207 |
| 6,310,477 B1 | 10/2001 | Schneider | 324/307 |
| 6,310,619 B1 | 10/2001 | Rice | 345/420 |
| 6,316,153 B1 | 11/2001 | Goodman et al. | 430/8 |
| 6,319,712 B1 | 11/2001 | Meenen et al. | 435/395 |
| 6,322,588 B1 | 11/2001 | Ogle et al. | 623/1.46 |
| 6,325,828 B1 | 12/2001 | Dennis et al. | 623/20.14 |
| 6,328,765 B1 | 12/2001 | Hardwick et al. | 623/23.72 |
| 6,334,006 B1 | 12/2001 | Tanabe | 385/12 |
| 6,334,066 B1 | 12/2001 | Rupprecht et al. | 600/411 |

(56) References Cited

U.S. PATENT DOCUMENTS

| | | |
|---|---|---|
| 6,342,075 B1 | 1/2002 | MacArthur ............... 623/20.14 |
| 6,344,043 B1 | 2/2002 | Pappas ........................... 606/96 |
| 6,344,059 B1 | 2/2002 | Krakovits et al. ......... 623/20.31 |
| 6,352,558 B1 | 3/2002 | Spector ..................... 623/18.11 |
| 6,358,253 B1 | 3/2002 | Torrie et al. ................... 606/96 |
| 6,365,405 B1 | 4/2002 | Salzmann et al. ............ 435/366 |
| 6,371,958 B1 | 4/2002 | Overaker ....................... 606/72 |
| 6,373,250 B1 | 4/2002 | Tsoref et al. ................. 324/309 |
| 6,375,658 B1 | 4/2002 | Hangody et al. ............... 606/80 |
| 6,379,367 B1 | 4/2002 | Vibe-Hansen et al. ....... 606/151 |
| 6,379,388 B1 | 4/2002 | Ensign et al. ............. 623/20.34 |
| 6,382,028 B1 | 5/2002 | Wooh et al. .................... 73/602 |
| 6,383,228 B1 | 5/2002 | Schmotzer ................. 623/23.35 |
| 6,387,131 B1 | 5/2002 | Miehlke et al. ............ 623/20.15 |
| 6,402,786 B1 | 6/2002 | Insall et al. ................ 623/20.35 |
| 6,429,013 B1 | 8/2002 | Halvorsen et al. ........... 435/377 |
| 6,443,988 B2 | 9/2002 | Felt et al. .................. 623/17.12 |
| 6,443,991 B1 | 9/2002 | Running .................... 623/20.27 |
| 6,444,222 B1 | 9/2002 | Asculai et al. ................ 424/484 |
| 6,450,978 B1 | 9/2002 | Brosseau et al. ............. 600/595 |
| 6,459,948 B1 | 10/2002 | Ateshian et al. ............. 700/117 |
| 6,468,314 B2 | 10/2002 | Schwartz et al. .......... 623/23.72 |
| 6,479,996 B1 | 11/2002 | Hoogeveen et al. ......... 324/309 |
| 6,482,209 B1 | 11/2002 | Engh et al. ..................... 606/79 |
| 6,510,334 B1 | 1/2003 | Schuster et al. ............. 600/407 |
| 6,514,514 B1 | 2/2003 | Atkinson et al. ............. 424/423 |
| 6,520,964 B2 | 2/2003 | Tallarida et al. ............. 396/567 |
| 6,533,737 B1 | 3/2003 | Brosseau et al. ............. 600/595 |
| 6,556,855 B2 | 4/2003 | Thesen ......................... 600/419 |
| 6,558,421 B1 | 5/2003 | Fell et al. ................... 623/14.12 |
| 6,560,476 B1 | 5/2003 | Pelletier et al. .............. 600/410 |
| 6,575,980 B1 | 6/2003 | Robie et al. .................... 606/88 |
| 6,591,581 B2 | 7/2003 | Schmieding ..................... 53/396 |
| 6,592,624 B1 | 7/2003 | Fraser et al. ............... 623/17.16 |
| 6,623,526 B1 | 9/2003 | Lloyd ........................ 623/20.28 |
| 6,626,945 B2 | 9/2003 | Simon et al. ............... 623/17.19 |
| 6,632,235 B2 | 10/2003 | Weikel et al. ................ 606/192 |
| 6,652,587 B2 | 11/2003 | Felt et al. ................... 623/20.16 |
| 6,679,917 B2 | 1/2004 | Ek .............................. 623/20.14 |
| 6,690,816 B2 | 2/2004 | Aylward et al. .............. 382/128 |
| 6,692,448 B2 | 2/2004 | Tanaka et al. ................ 600/587 |
| 6,702,821 B2 | 3/2004 | Bonutti .......................... 606/88 |
| 6,712,856 B1 | 3/2004 | Carignan et al. ........... 623/20.35 |
| 6,719,794 B2 | 4/2004 | Gerber et al. .............. 623/17.11 |
| 6,770,078 B2 | 8/2004 | Bonutti .......................... 606/86 |
| 6,772,026 B2 | 8/2004 | Bradbury et al. ............. 700/98 |
| 6,799,066 B2 | 9/2004 | Steines et al. ................ 600/407 |
| 6,816,607 B2 | 11/2004 | O'Donnell et al. .......... 382/131 |
| 6,835,377 B2 | 12/2004 | Goldberg et al. ............ 424/93.7 |
| 6,855,165 B2 | 2/2005 | Fell et al. ................... 623/14.12 |
| 6,873,741 B2 | 3/2005 | Li .................................. 382/266 |
| 6,893,463 B2 | 5/2005 | Fell et al. ................... 623/14.12 |
| 6,893,467 B1 | 5/2005 | Bercovy .................... 623/20.14 |
| 6,902,582 B2 | 6/2005 | Kubein-Meesenburg et al. ............................ 623/20.31 |
| 6,905,514 B2 | 6/2005 | Carignan et al. ........... 623/20.35 |
| 6,911,044 B2 | 6/2005 | Fell et al. ................... 623/14.12 |
| 6,916,341 B2 | 7/2005 | Rolston ........................ 623/20.3 |
| 6,923,817 B2 | 8/2005 | Carson et al. ................. 606/130 |
| 6,923,831 B2 | 8/2005 | Fell et al. ................... 623/14.12 |
| 6,932,842 B1 | 8/2005 | Litschko et al. ............ 623/16.11 |
| 6,964,687 B1 | 11/2005 | Bernard et al. ............. 623/17.16 |
| 6,966,928 B2 | 11/2005 | Fell et al. ................... 623/14.12 |
| 6,978,188 B1 | 12/2005 | Christensen .................. 700/118 |
| 6,984,981 B2 | 1/2006 | Tamez-Peña et al. ....... 324/309 |
| 6,998,841 B1 | 2/2006 | Tamez-Peña et al. ....... 324/302 |
| 7,013,191 B2 | 3/2006 | Rubbert et al. ................ 700/98 |
| 7,020,314 B1 | 3/2006 | Suri et al. ..................... 382/130 |
| 7,048,741 B2 | 5/2006 | Swanson ........................ 606/88 |
| 7,050,534 B2 | 5/2006 | Lang ............................. 378/54 |
| 7,058,159 B2 | 6/2006 | Lang et al. ..................... 378/54 |
| 7,058,209 B2 | 6/2006 | Chen et al. .................... 382/117 |
| 7,060,101 B2 | 6/2006 | O'Connor et al. .......... 623/20.32 |
| 7,105,026 B2 | 9/2006 | Johnson et al. ............ 623/20.14 |
| 7,115,131 B2 | 10/2006 | Engh et al. ..................... 606/79 |
| 7,117,027 B2 | 10/2006 | Zheng et al. ................. 600/426 |
| 7,172,596 B2 | 2/2007 | Coon et al. ..................... 606/87 |
| 7,174,282 B2 | 2/2007 | Hollister et al. .................. 703/2 |
| 7,184,814 B2 | 2/2007 | Lang et al. .................... 600/416 |
| 7,204,807 B2 | 4/2007 | Tsoref .......................... 600/438 |
| 7,238,203 B2 | 7/2007 | Bagga et al. ............... 623/17.11 |
| 7,239,908 B1 | 7/2007 | Alexander et al. ........... 600/427 |
| 7,244,273 B2 | 7/2007 | Pedersen et al. ........... 623/14.12 |
| 7,245,697 B2 | 7/2007 | Lang ............................. 378/54 |
| 7,264,635 B2 | 9/2007 | Suguro et al. ............. 623/20.14 |
| 7,292,674 B2 | 11/2007 | Lang ............................. 378/54 |
| 7,326,252 B2 | 2/2008 | Otto et al. .................. 623/20.15 |
| 7,379,529 B2 | 5/2008 | Lang ............................. 378/54 |
| 7,427,200 B2 | 9/2008 | Noble et al. .................. 434/274 |
| 7,438,685 B2 | 10/2008 | Burdette et al. ............. 600/439 |
| 7,467,892 B2 | 12/2008 | Lang et al. .................. 378/207 |
| 7,468,075 B2 | 12/2008 | Lang et al. ................. 623/16.11 |
| 7,517,358 B2 | 4/2009 | Petersen ...................... 606/247 |
| 7,520,901 B2 | 4/2009 | Engh et al. ................. 623/20.21 |
| 7,534,263 B2 | 5/2009 | Burdulis, Jr. et al. ..... 623/14.12 |
| 7,572,293 B2 | 8/2009 | Rhodes et al. ............. 623/20.32 |
| 7,603,192 B2 | 10/2009 | Martin et al. .................. 700/98 |
| 7,611,519 B2 | 11/2009 | Lefevre et al. ............... 606/102 |
| 7,611,653 B1 | 11/2009 | Elsner et al. ................. 264/255 |
| 7,615,054 B1 | 11/2009 | Bonutti .......................... 606/88 |
| 7,618,451 B2 | 11/2009 | Berez et al. ................ 623/14.12 |
| 7,634,119 B2 | 12/2009 | Tsougarakis et al. ........ 382/128 |
| 7,678,152 B2 | 3/2010 | Suguro et al. ............. 623/20.27 |
| 7,718,109 B2 | 5/2010 | Robb et al. ................... 264/308 |
| 7,796,791 B2 | 9/2010 | Tsougarakis et al. ........ 382/128 |
| 7,799,077 B2 | 9/2010 | Lang et al. ................. 623/14.12 |
| 7,806,896 B1 | 10/2010 | Bonutti ...................... 606/86 R |
| 7,842,092 B2 | 11/2010 | Otto et al. .................. 623/18.11 |
| 7,881,768 B2 | 2/2011 | Lang et al. ................... 600/407 |
| 7,914,582 B2 | 3/2011 | Felt et al. ................... 623/20.16 |
| 7,935,151 B2 | 5/2011 | Haines ....................... 623/20.35 |
| 7,981,158 B2 | 7/2011 | Fitz et al. ................... 623/17.16 |
| 7,983,777 B2 | 7/2011 | Melton et al. .................. 700/98 |
| 8,036,729 B2 | 10/2011 | Lang et al. ................... 600/407 |
| 8,062,302 B2 | 11/2011 | Lang et al. ..................... 606/87 |
| 8,066,708 B2 | 11/2011 | Lang et al. ..................... 606/88 |
| 8,070,821 B2 | 12/2011 | Roger ........................ 623/20.17 |
| 8,077,950 B2 | 12/2011 | Tsougarakis et al. ........ 382/128 |
| 8,083,745 B2 | 12/2011 | Lang et al. ..................... 606/87 |
| 8,086,336 B2 | 12/2011 | Christensen .................. 700/98 |
| 8,094,900 B2 | 1/2012 | Steines et al. ................ 382/128 |
| 8,105,330 B2 | 1/2012 | Fitz et al. ....................... 606/88 |
| 8,112,142 B2 | 2/2012 | Alexander et al. ........... 600/407 |
| RE43,282 E | 3/2012 | Alexander et al. ........... 600/427 |
| 8,192,498 B2 | 6/2012 | Wagner et al. ............. 623/20.21 |
| 8,211,181 B2 | 7/2012 | Walker ....................... 623/20.21 |
| 8,221,430 B2 | 7/2012 | Park et al. ...................... 606/88 |
| 8,234,097 B2 * | 7/2012 | Steines et al. .................. 703/1 |
| 8,236,061 B2 | 8/2012 | Heldreth et al. ............ 623/20.31 |
| 8,265,730 B2 | 9/2012 | Alexander et al. ........... 600/410 |
| 8,306,601 B2 | 11/2012 | Lang et al. ................... 600/407 |
| 8,311,306 B2 | 11/2012 | Pavlovskaia et al. ........ 382/131 |
| 8,337,501 B2 | 12/2012 | Fitz et al. ................... 606/86 R |
| 8,337,507 B2 | 12/2012 | Lang et al. ................... 606/102 |
| 8,343,218 B2 | 1/2013 | Lang et al. ................. 623/16.11 |
| 8,352,056 B2 | 1/2013 | Lee et al. ....................... 700/97 |
| 8,361,076 B2 | 1/2013 | Roose et al. .................... 606/88 |
| 8,366,771 B2 | 2/2013 | Burdulis, Jr. et al. ..... 623/14.12 |
| 8,369,926 B2 | 2/2013 | Lang et al. ................... 600/407 |
| 8,377,073 B2 | 2/2013 | Wasielewski ................. 606/102 |
| 8,377,129 B2 | 2/2013 | Fitz et al. ................... 623/14.12 |
| 8,380,471 B2 | 2/2013 | Iannotti et al. .................... 703/6 |
| 8,407,067 B2 | 3/2013 | Uthgenannt et al. ........... 705/2 |
| 8,439,926 B2 | 5/2013 | Bojarski et al. ................ 606/88 |
| 8,457,930 B2 | 6/2013 | Schroeder ........................ 703/1 |
| 8,460,304 B2 | 6/2013 | Fitz et al. ....................... 606/88 |
| 8,473,305 B2 | 6/2013 | Belcher et al. .................. 705/2 |
| 8,480,754 B2 | 7/2013 | Bojarski et al. ............ 623/20.35 |
| 8,486,150 B2 | 7/2013 | White et al. ................ 623/20.21 |
| 8,500,740 B2 | 8/2013 | Bojarski et al. ............ 606/86 R |
| 8,521,492 B2 | 8/2013 | Otto et al. ........................ 703/6 |
| 8,529,568 B2 | 9/2013 | Bouadi ........................... 606/84 |
| 8,529,630 B2 | 9/2013 | Bojarski et al. ............ 623/20.14 |
| 8,532,807 B2 | 9/2013 | Metzger ......................... 700/98 |

(56) References Cited

U.S. PATENT DOCUMENTS

| | | | | |
|---|---|---|---|---|
| 8,545,569 | B2 | 10/2013 | Fitz et al. | 623/20.14 |
| 8,551,099 | B2 | 10/2013 | Lang et al. | 606/86 R |
| 8,551,102 | B2 | 10/2013 | Fitz et al. | 606/88 |
| 8,551,103 | B2 | 10/2013 | Fitz et al. | 606/88 |
| 8,551,169 | B2 | 10/2013 | Fitz et al. | 623/14.12 |
| 8,556,906 | B2 | 10/2013 | Fitz et al. | 606/87 |
| 8,556,907 | B2 | 10/2013 | Fitz et al. | 606/87 |
| 8,556,971 | B2 | 10/2013 | Lang | 623/14.12 |
| 8,556,983 | B2 | 10/2013 | Bojarski et al. | 623/20.35 |
| 8,561,278 | B2 | 10/2013 | Fitz et al. | 29/407.09 |
| 8,562,611 | B2 | 10/2013 | Fitz et al. | 606/80 |
| 8,562,618 | B2 | 10/2013 | Fitz et al. | 606/88 |
| 8,568,479 | B2 | 10/2013 | Fitz et al. | 623/14.12 |
| 8,568,480 | B2 | 10/2013 | Fitz et al. | 623/14.12 |
| 8,617,172 | B2 | 12/2013 | Fitz et al. | 606/88 |
| 8,617,175 | B2 | 12/2013 | Park et al. | 606/89 |
| 8,617,242 | B2 | 12/2013 | Philipp | 623/16.11 |
| 8,623,023 | B2 | 1/2014 | Ritchey et al. | 606/96 |
| 8,634,617 | B2 | 1/2014 | Tsougarakis et al. | 382/128 |
| 8,638,998 | B2 | 1/2014 | Steines et al. | 382/128 |
| 8,641,716 | B2 | 2/2014 | Fitz et al. | 606/80 |
| 8,682,052 | B2 | 3/2014 | Fitz et al. | 382/131 |
| 8,690,945 | B2 | 4/2014 | Fitz et al. | 623/16.11 |
| 8,709,089 | B2 | 4/2014 | Lang et al. | 623/18.11 |
| 8,735,773 | B2 | 5/2014 | Lang | 219/121.72 |
| 8,768,028 | B2 | 7/2014 | Lang et al. | 382/131 |
| 8,771,365 | B2 | 7/2014 | Bojarski et al. | 623/20.32 |
| 8,801,720 | B2 * | 8/2014 | Park et al. | 606/88 |
| 8,882,847 | B2 | 11/2014 | Burdulis, Jr. et al. | 623/20.32 |
| 8,906,107 | B2 | 12/2014 | Bojarski et al. | 623/20.35 |
| 8,926,706 | B2 | 1/2015 | Bojarski et al. | 623/20.3 |
| 8,932,363 | B2 | 1/2015 | Tsougarakis et al. | 623/20.14 |
| 8,945,230 | B2 | 2/2015 | Lang et al. | 623/20.31 |
| 8,965,088 | B2 | 2/2015 | Tsougarakis et al. | 382/128 |
| 8,968,320 | B2 * | 3/2015 | Park et al. | 606/88 |
| 8,974,539 | B2 | 3/2015 | Bojarski et al. | 623/20.35 |
| 9,020,788 | B2 | 4/2015 | Lang et al. | 703/6 |
| 9,180,015 | B2 | 11/2015 | Fitz et al. | 382/128 |
| 9,186,254 | B2 | 11/2015 | Fitz et al. | |
| 9,308,091 | B2 | 4/2016 | Lang | |
| 9,320,620 | B2 | 4/2016 | Bojarski et al. | 606/79 |
| 9,333,085 | B2 | 5/2016 | Fitz et al. | 623/16.11 |
| 2001/0001120 | A1 | 5/2001 | Masini | 606/86 |
| 2001/0010023 | A1 | 7/2001 | Schwartz et al. | 623/23.72 |
| 2001/0039455 | A1 | 11/2001 | Simon et al. | 623/23.51 |
| 2002/0013626 | A1 | 1/2002 | Geistlich et al. | 623/23.57 |
| 2002/0016543 | A1 | 2/2002 | Tyler | 600/410 |
| 2002/0022884 | A1 | 2/2002 | Mansmann | 623/14.12 |
| 2002/0028980 | A1 | 3/2002 | Thierfelder et al. | 600/37 |
| 2002/0045940 | A1 | 4/2002 | Giannetti et al. | 623/11.11 |
| 2002/0052606 | A1 | 5/2002 | Bonutti | 606/88 |
| 2002/0059049 | A1 | 5/2002 | Bradbury et al. | 703/11 |
| 2002/0067798 | A1 | 6/2002 | Lang et al. | 378/54 |
| 2002/0068979 | A1 | 6/2002 | Brown et al. | 623/20.3 |
| 2002/0072821 | A1 | 6/2002 | Baker | 700/98 |
| 2002/0082703 | A1 | 6/2002 | Repicci | 623/20.29 |
| 2002/0082741 | A1 | 6/2002 | Mazumder et al. | 700/123 |
| 2002/0087274 | A1 | 7/2002 | Alexander et al. | 702/19 |
| 2002/0106625 | A1 | 8/2002 | Hung et al. | 435/1.1 |
| 2002/0111694 | A1 | 8/2002 | Ellingsen et al. | 623/23.57 |
| 2002/0115647 | A1 | 8/2002 | Halvorsen et al. | 514/171 |
| 2002/0120274 | A1 | 8/2002 | Overaker et al. | 606/72 |
| 2002/0120281 | A1 | 8/2002 | Overaker | 606/151 |
| 2002/0127264 | A1 | 9/2002 | Felt et al. | 424/423 |
| 2002/0133230 | A1 | 9/2002 | Repicci | 623/14.12 |
| 2002/0143402 | A1 | 10/2002 | Steinberg | 623/22.16 |
| 2002/0147392 | A1 | 10/2002 | Steines et al. | 600/407 |
| 2002/0151986 | A1 | 10/2002 | Asculai et al. | 424/484 |
| 2002/0156150 | A1 | 10/2002 | Williams et al. | 523/113 |
| 2002/0173852 | A1 | 11/2002 | Felt et al. | 623/20.32 |
| 2002/0177770 | A1 | 11/2002 | Lang et al. | 600/410 |
| 2002/0183850 | A1 | 12/2002 | Felt et al. | 623/20.16 |
| 2003/0015208 | A1 | 1/2003 | Lang et al. | 128/922 |
| 2003/0031292 | A1 | 2/2003 | Lang | 378/54 |
| 2003/0035773 | A1 | 2/2003 | Totterman et al. | 424/9.1 |
| 2003/0045935 | A1 | 3/2003 | Angelucci et al. | 623/17.11 |
| 2003/0055500 | A1 | 3/2003 | Fell et al. | 623/14.12 |
| 2003/0055501 | A1 | 3/2003 | Fell et al. | 623/14.12 |
| 2003/0055502 | A1 | 3/2003 | Lang et al. | 623/16.11 |
| 2003/0060882 | A1 | 3/2003 | Fell et al. | 623/14.12 |
| 2003/0060883 | A1 | 3/2003 | Fell et al. | 623/14.12 |
| 2003/0060884 | A1 | 3/2003 | Fell et al. | 623/14.12 |
| 2003/0060885 | A1 | 3/2003 | Fell et al. | 623/14.12 |
| 2003/0063704 | A1 | 4/2003 | Lang | 378/54 |
| 2003/0069591 | A1 | 4/2003 | Carson et al. | 606/130 |
| 2003/0100953 | A1 | 5/2003 | Rosa et al. | 623/20.3 |
| 2003/0158606 | A1 | 8/2003 | Coon et al. | 623/20.15 |
| 2003/0171757 | A1 | 9/2003 | Coon et al. | 606/87 |
| 2003/0216669 | A1 | 11/2003 | Lang et al. | 600/587 |
| 2003/0225457 | A1 | 12/2003 | Justin et al. | 623/20.14 |
| 2003/0236473 | A1 | 12/2003 | Dore et al. | 600/587 |
| 2004/0006393 | A1 | 1/2004 | Burkinshaw | 623/20.3 |
| 2004/0062358 | A1 | 4/2004 | Lang et al. | 378/207 |
| 2004/0081287 | A1 | 4/2004 | Lang et al. | 378/210 |
| 2004/0098132 | A1 | 5/2004 | Andriacchi et al. | 623/20.35 |
| 2004/0098133 | A1 | 5/2004 | Carignan et al. | 623/20.35 |
| 2004/0102851 | A1 | 5/2004 | Saladino | 623/20.15 |
| 2004/0102852 | A1 | 5/2004 | Johnson et al. | 623/20.15 |
| 2004/0102866 | A1 * | 5/2004 | Harris et al. | 700/117 |
| 2004/0117015 | A1 | 6/2004 | Biscup | 623/16.11 |
| 2004/0117023 | A1 | 6/2004 | Gerbec et al. | 623/18.11 |
| 2004/0122521 | A1 | 6/2004 | Lee et al. | 623/20.15 |
| 2004/0133276 | A1 | 7/2004 | Lang et al. | 623/14.12 |
| 2004/0136583 | A1 | 7/2004 | Harada et al. | 382/131 |
| 2004/0138754 | A1 | 7/2004 | Lang et al. | 623/20.14 |
| 2004/0138755 | A1 | 7/2004 | O'Connor et al. | 623/20.32 |
| 2004/0147927 | A1 | 7/2004 | Tsougarakis et al. | 606/53 |
| 2004/0153079 | A1 | 8/2004 | Tsougarakis et al. | 606/77 |
| 2004/0153162 | A1 | 8/2004 | Sanford et al. | 623/20.3 |
| 2004/0153164 | A1 | 8/2004 | Sanford et al. | 623/20.29 |
| 2004/0167390 | A1 | 8/2004 | Alexander et al. | 600/410 |
| 2004/0167630 | A1 | 8/2004 | Rolston | 623/20.14 |
| 2004/0193280 | A1 | 9/2004 | Webster et al. | 623/20.33 |
| 2004/0199249 | A1 | 10/2004 | Fell | 623/14.12 |
| 2004/0199258 | A1 | 10/2004 | MacAra | 623/22.32 |
| 2004/0204644 | A1 | 10/2004 | Tsougarakis et al. | 600/410 |
| 2004/0204760 | A1 | 10/2004 | Fitz et al. | 623/14.12 |
| 2004/0204766 | A1 | 10/2004 | Siebel | 623/20.31 |
| 2004/0236424 | A1 | 11/2004 | Berez et al. | 623/14.12 |
| 2005/0010106 | A1 | 1/2005 | Lang et al. | 600/425 |
| 2005/0015153 | A1 | 1/2005 | Goble et al. | 623/23.46 |
| 2005/0021042 | A1 | 1/2005 | Marnay et al. | 606/99 |
| 2005/0033424 | A1 | 2/2005 | Fell | 623/14.12 |
| 2005/0043807 | A1 | 2/2005 | Wood | 623/20.14 |
| 2005/0055028 | A1 | 3/2005 | Haines | 606/79 |
| 2005/0078802 | A1 | 4/2005 | Lang et al. | 387/207 |
| 2005/0107883 | A1 | 5/2005 | Goodfried et al. | 623/20.15 |
| 2005/0107884 | A1 | 5/2005 | Johnson et al. | 623/20.15 |
| 2005/0119664 | A1 | 6/2005 | Carignan et al. | 606/96 |
| 2005/0125029 | A1 | 6/2005 | Bernard et al. | 606/205 |
| 2005/0148843 | A1 | 7/2005 | Roose | 700/117 |
| 2005/0154471 | A1 | 7/2005 | Aram et al. | 623/20.15 |
| 2005/0171612 | A1 | 8/2005 | Rolston | 623/20.19 |
| 2005/0197814 | A1 | 9/2005 | Aram et al. | 703/11 |
| 2005/0203384 | A1 | 9/2005 | Sati et al. | 600/426 |
| 2005/0216305 | A1 | 9/2005 | Funderud | 705/2 |
| 2005/0226374 | A1 | 10/2005 | Lang et al. | 378/54 |
| 2005/0234461 | A1 | 10/2005 | Burdulis, Jr. et al. | 606/79 |
| 2005/0244239 | A1 | 11/2005 | Shimp | 409/132 |
| 2005/0267584 | A1 | 12/2005 | Burdulis et al. | 623/20.19 |
| 2005/0278034 | A1 | 12/2005 | Johnson et al. | 623/20.15 |
| 2006/0009853 | A1 | 1/2006 | Justin et al. | 623/20.3 |
| 2006/0015120 | A1 | 1/2006 | Richard et al. | 606/102 |
| 2006/0058884 | A1 | 3/2006 | Aram et al. | 623/20.15 |
| 2006/0069318 | A1 | 3/2006 | Keaveny et al. | 600/300 |
| 2006/0094951 | A1 | 5/2006 | Dean et al. | 600/407 |
| 2006/0111722 | A1 | 5/2006 | Bouadi | 606/79 |
| 2006/0111726 | A1 | 5/2006 | Felt et al. | 606/86 |
| 2006/0129246 | A1 | 6/2006 | Steffensmeier | 623/20.29 |
| 2006/0136058 | A1 | 6/2006 | Pietrzak | 623/13.14 |
| 2006/0149283 | A1 | 7/2006 | May et al. | 606/96 |
| 2006/0149374 | A1 | 7/2006 | Winslow et al. | 623/17.11 |
| 2006/0190086 | A1 | 8/2006 | Clemow et al. | 623/20.15 |
| 2006/0210017 | A1 | 9/2006 | Lang | 378/54 |

(56) References Cited

U.S. PATENT DOCUMENTS

| | | |
|---|---|---|
| 2006/0210018 A1 | 9/2006 | Lang .................... 378/54 |
| 2006/0265078 A1 | 11/2006 | McMinn ............ 623/20.14 |
| 2007/0005143 A1 | 1/2007 | Ek et al. ............. 623/20.32 |
| 2007/0015995 A1 | 1/2007 | Lang .................... 600/407 |
| 2007/0038223 A1 | 2/2007 | Marquart et al. ....... 606/86 |
| 2007/0047794 A1 | 3/2007 | Lang et al. ............. 378/132 |
| 2007/0067032 A1 | 3/2007 | Felt et al. ............ 623/14.12 |
| 2007/0083266 A1 | 4/2007 | Lang .................. 623/17.11 |
| 2007/0100462 A1 | 5/2007 | Lang et al. ........... 623/20.29 |
| 2007/0118055 A1 | 5/2007 | McCombs .............. 600/587 |
| 2007/0118222 A1 | 5/2007 | Lang .................. 623/17.12 |
| 2007/0118243 A1 | 5/2007 | Schroeder et al. ...... 700/118 |
| 2007/0156171 A1 | 7/2007 | Lang et al. ............ 606/205 |
| 2007/0190108 A1 | 8/2007 | Datta et al. ............ 424/423 |
| 2007/0198022 A1 | 8/2007 | Lang et al. ............. 606/88 |
| 2007/0203430 A1 | 8/2007 | Lang et al. ............. 600/587 |
| 2007/0226986 A1 | 10/2007 | Park et al. .............. 29/592 |
| 2007/0233156 A1 | 10/2007 | Metzger ................ 606/130 |
| 2007/0233269 A1 | 10/2007 | Steines et al. ....... 623/20.21 |
| 2007/0239165 A1 | 10/2007 | Amirouche ............ 606/86 |
| 2007/0250169 A1 | 10/2007 | Lang .................. 623/17.12 |
| 2007/0255288 A1 | 11/2007 | Mahfouz et al. ........ 606/102 |
| 2007/0274444 A1 | 11/2007 | Lang .................... 378/54 |
| 2007/0276224 A1 | 11/2007 | Lang et al. .............. 600/410 |
| 2007/0276501 A1 | 11/2007 | Betz et al. ............ 623/17.16 |
| 2007/0282451 A1 | 12/2007 | Metzger et al. ...... 623/20.28 |
| 2008/0009950 A1 | 1/2008 | Richardson ......... 623/20.29 |
| 2008/0015433 A1 | 1/2008 | Alexander et al. ...... 600/427 |
| 2008/0025463 A1 | 1/2008 | Lang .................... 378/54 |
| 2008/0031412 A1 | 2/2008 | Lang et al. ............. 378/54 |
| 2008/0058613 A1 | 3/2008 | Lang et al. ............. 600/300 |
| 2008/0058945 A1 | 3/2008 | Hajaj et al. ........... 623/20.14 |
| 2008/0119938 A1 | 5/2008 | Oh .................. 623/20.14 |
| 2008/0119940 A1 | 5/2008 | Otto et al. ........... 623/20.31 |
| 2008/0140212 A1 | 6/2008 | Metzger et al. ....... 623/20.31 |
| 2008/0147072 A1 | 6/2008 | Park et al. ............. 606/87 |
| 2008/0170659 A1 | 7/2008 | Lang et al. ............. 378/56 |
| 2008/0172125 A1 | 7/2008 | Ek ...................... 623/14.12 |
| 2008/0195108 A1 | 8/2008 | Bhatnagar et al. ...... 606/87 |
| 2008/0195216 A1 | 8/2008 | Philipp ............... 623/18.11 |
| 2008/0208348 A1 | 8/2008 | Fitz .................... 623/19.14 |
| 2008/0215059 A1 | 9/2008 | Carignan et al. ........ 606/96 |
| 2008/0219412 A1 | 9/2008 | Lang .................... 378/207 |
| 2008/0243127 A1 | 10/2008 | Lang et al. .............. 606/87 |
| 2008/0255445 A1 | 10/2008 | Neubauer et al. ....... 600/416 |
| 2008/0257363 A1 | 10/2008 | Schoenefeld et al. .... 128/897 |
| 2008/0262624 A1 | 10/2008 | White et al. ......... 623/20.32 |
| 2008/0275452 A1 | 11/2008 | Lang et al. .............. 606/88 |
| 2008/0281328 A1 | 11/2008 | Lang et al. .............. 606/87 |
| 2008/0281329 A1 | 11/2008 | Fitz et al. ........... 623/17.16 |
| 2008/0281426 A1 | 11/2008 | Fitz et al. ........... 623/17.16 |
| 2008/0319448 A1 | 12/2008 | Lavallee et al. ........ 606/102 |
| 2009/0062925 A1 | 3/2009 | Samuelson ........... 623/23.12 |
| 2009/0076371 A1 | 3/2009 | Lang et al. .............. 600/407 |
| 2009/0076508 A1 | 3/2009 | Weinans et al. ......... 606/62 |
| 2009/0088865 A1 | 4/2009 | Brehm ................ 623/22.21 |
| 2009/0110498 A1 | 4/2009 | Park .................... 408/1 |
| 2009/0118830 A1 | 5/2009 | Fell .................... 623/14.12 |
| 2009/0131941 A1 | 5/2009 | Park et al. ............. 606/87 |
| 2009/0138020 A1 | 5/2009 | Park et al. ............. 606/88 |
| 2009/0149977 A1 | 6/2009 | Schendel ............... 700/98 |
| 2009/0151736 A1 | 6/2009 | Belcher et al. ........ 128/898 |
| 2009/0222103 A1 | 9/2009 | Fitz et al. ........... 623/18.11 |
| 2009/0226068 A1 | 9/2009 | Fitz et al. ........... 382/131 |
| 2009/0228111 A1 | 9/2009 | Otto .................. 623/20.19 |
| 2009/0228113 A1 | 9/2009 | Lang et al. ........... 623/20.32 |
| 2009/0270868 A1 | 10/2009 | Park et al. ............. 606/87 |
| 2009/0276045 A1 | 11/2009 | Lang .................. 623/14.12 |
| 2009/0306676 A1 | 12/2009 | Lang et al. ............. 606/102 |
| 2009/0312805 A1 | 12/2009 | Lang et al. ........... 606/86 R |
| 2009/0326666 A1 | 12/2009 | Wyss et al. .......... 623/20.39 |
| 2009/0326670 A1 | 12/2009 | Keefer et al. ........ 623/22.22 |
| 2010/0042105 A1 | 2/2010 | Park et al. ............. 606/87 |
| 2010/0049195 A1 | 2/2010 | Park et al. ............. 606/87 |
| 2010/0054572 A1 | 3/2010 | Tsougarakis et al. ...... 382/131 |
| 2010/0152741 A1 | 6/2010 | Park et al. ............. 606/89 |
| 2010/0191244 A1 | 7/2010 | White et al. ........... 606/88 |
| 2010/0217270 A1 | 8/2010 | Polinski et al. ......... 606/87 |
| 2010/0274534 A1 | 10/2010 | Steines et al. ......... 703/1 |
| 2010/0292963 A1 | 11/2010 | Schroeder .............. 703/1 |
| 2010/0303313 A1 | 12/2010 | Lang et al. ............. 382/128 |
| 2010/0303317 A1 | 12/2010 | Tsougarakis et al. ...... 382/128 |
| 2010/0303324 A1 | 12/2010 | Lang et al. ............. 382/131 |
| 2010/0305575 A1 | 12/2010 | Wilkinson et al. ....... 606/88 |
| 2010/0305708 A1 | 12/2010 | Lang et al. ........... 623/20.18 |
| 2010/0305907 A1 | 12/2010 | Fitz et al. .............. 703/1 |
| 2010/0329530 A1 | 12/2010 | Lang et al. ............. 382/131 |
| 2010/0331991 A1 | 12/2010 | Wilkinson et al. ..... 623/20.32 |
| 2010/0332194 A1 | 12/2010 | McGuan et al. .......... 703/1 |
| 2011/0022179 A1 | 1/2011 | Andriacchi et al. ..... 623/20.18 |
| 2011/0029091 A1 | 2/2011 | Bojarski et al. ....... 623/20.32 |
| 2011/0029093 A1 | 2/2011 | Bojarski et al. ....... 623/20.35 |
| 2011/0040387 A1 | 2/2011 | Ries et al. ............ 623/20.27 |
| 2011/0046735 A1 | 2/2011 | Metzger et al. ........ 623/14.12 |
| 2011/0066245 A1 | 3/2011 | Lang et al. ............ 623/18.11 |
| 2011/0071645 A1 | 3/2011 | Bojarski et al. ....... 623/20.35 |
| 2011/0071802 A1 | 3/2011 | Bojarski et al. .......... 703/1 |
| 2011/0087332 A1 | 4/2011 | Bojarski et al. ....... 623/20.32 |
| 2011/0087465 A1 | 4/2011 | Mahfouz .................. 703/1 |
| 2011/0092804 A1 | 4/2011 | Schoenefeld et al. .... 600/416 |
| 2011/0093108 A1 | 4/2011 | Ashby et al. ........... 700/103 |
| 2011/0125009 A1 | 5/2011 | Lang et al. ............. 600/425 |
| 2011/0144760 A1 | 6/2011 | Wong et al. ........... 623/20.14 |
| 2011/0184526 A1 | 7/2011 | White et al. ......... 623/20.32 |
| 2011/0218635 A1 | 9/2011 | Amis et al. .......... 623/20.18 |
| 2011/0264097 A1 | 10/2011 | Hodorek et al. .......... 606/88 |
| 2011/0266265 A1 | 11/2011 | Lang .................. 219/121.72 |
| 2011/0288669 A1 | 11/2011 | Sanford et al. ......... 700/103 |
| 2011/0295378 A1 | 12/2011 | Bojarski et al. ....... 623/20.35 |
| 2011/0305379 A1 | 12/2011 | Mahfouz ............... 382/131 |
| 2012/0022659 A1 | 1/2012 | Wentorf ............... 623/20.32 |
| 2012/0093377 A1 | 4/2012 | Tsougarakis et al. ...... 382/128 |
| 2012/0116203 A1 | 5/2012 | Vancraen et al. ......... 600/407 |
| 2012/0158671 A1 | 6/2012 | Tzur et al. ........... 623/20.35 |
| 2012/0191205 A1 | 7/2012 | Bojarski et al. ....... 623/20.32 |
| 2012/0191420 A1 | 7/2012 | Bojarski et al. .......... 703/1 |
| 2012/0197408 A1 | 8/2012 | Lang et al. ........... 623/18.11 |
| 2012/0201440 A1 | 8/2012 | Steines et al. ......... 382/131 |
| 2012/0209394 A1 | 8/2012 | Bojarski et al. ....... 623/20.32 |
| 2012/0232669 A1 | 9/2012 | Bojarski et al. ......... 623/20.3 |
| 2012/0232670 A1 | 9/2012 | Bojarski et al. ....... 623/20.35 |
| 2012/0232671 A1 | 9/2012 | Bojarski et al. ....... 623/20.35 |
| 2012/0265496 A1 | 10/2012 | Mahfouz .................. 703/1 |
| 2013/0006598 A1 | 1/2013 | Alexander et al. ....... 703/11 |
| 2013/0012553 A1 | 1/2013 | MacDonald et al. ...... 514/365 |
| 2013/0030419 A1 | 1/2013 | Fitz et al. ................ 606/1 |
| 2013/0071828 A1 | 3/2013 | Lang et al. ............. 434/274 |
| 2013/0079781 A1 | 3/2013 | Fitz et al. .............. 606/80 |
| 2013/0079876 A1 | 3/2013 | Fitz et al. ........... 623/14.12 |
| 2013/0081247 A1 | 4/2013 | Fitz et al. ........... 29/407.09 |
| 2013/0103363 A1 | 4/2013 | Lang et al. .............. 703/1 |
| 2013/0110471 A1 | 5/2013 | Lang et al. .............. 703/1 |
| 2013/0144570 A1 | 6/2013 | Axelson, Jr. et al. ...... 703/1 |
| 2013/0158671 A1 | 6/2013 | Uthgenannt et al. ..... 623/20.35 |
| 2013/0165939 A1 | 6/2013 | Ries et al. ............. 606/88 |
| 2013/0197870 A1 | 8/2013 | Steines et al. .......... 703/1 |
| 2013/0199259 A1 | 8/2013 | Smith ................... 72/362 |
| 2013/0203031 A1 | 8/2013 | McKinnon et al. ....... 434/262 |
| 2013/0211531 A1 | 8/2013 | Steines et al. ......... 623/20.35 |
| 2013/0245803 A1 | 9/2013 | Lang ..................... 700/98 |
| 2013/0297031 A1 | 11/2013 | Hafez ................ 623/20.14 |
| 2014/0005792 A1 | 1/2014 | Lang et al. ........... 623/20.32 |
| 2014/0029814 A1 | 1/2014 | Fitz et al. ............. 382/128 |
| 2014/0039631 A1 | 2/2014 | Bojarski et al. ....... 623/18.11 |
| 2014/0086780 A1 | 3/2014 | Miller et al. ............ 419/1 |
| 2014/0109384 A1 | 4/2014 | Lang ................... 29/557 |
| 2014/0115872 A1 | 5/2014 | Steines et al. .......... 29/592 |
| 2014/0136154 A1 | 5/2014 | Bojarski et al. .......... 703/1 |
| 2014/0153798 A1 | 6/2014 | Tsougarakis et al. ...... 382/128 |
| 2014/0172111 A1 | 6/2014 | Lang et al. .......... 623/20.32 |
| 2014/0194996 A1 | 7/2014 | Bojarski et al. ....... 623/20.35 |
| 2014/0207243 A1 | 7/2014 | Fitz et al. ........... 623/20.16 |
| 2014/0222390 A1 | 8/2014 | Asseln et al. ............. 703/1 |
| 2014/0228860 A1 | 8/2014 | Steines et al. .......... 606/130 |

(56) References Cited

U.S. PATENT DOCUMENTS

| | | | |
|---|---|---|---|
| 2014/0250676 A1 | 9/2014 | Lang et al. | 29/592 |
| 2014/0250677 A1 | 9/2014 | Lang | 29/592 |
| 2014/0257508 A1 | 9/2014 | Bojarski et al. | 623/20.35 |
| 2014/0259629 A1 | 9/2014 | Dion et al. | 29/558 |
| 2014/0303629 A1 | 10/2014 | Lang et al. | 606/87 |
| 2014/0324205 A1 | 10/2014 | Park et al. | 700/98 |
| 2014/0336774 A1 | 11/2014 | Fitz et al. | 623/20.35 |
| 2015/0032215 A1 | 1/2015 | Slamin et al. | 623/20.21 |
| 2015/0032217 A1 | 1/2015 | Bojarski et al. | 623/20.32 |
| 2015/0081029 A1 | 3/2015 | Bojarski et al. | 623/20.32 |
| 2015/0157461 A1 | 6/2015 | Burdulis, Jr. et al. | |
| 2015/0216615 A1 | 8/2015 | Tsougarakis et al. | |
| 2016/0143744 A1 | 5/2016 | Bojarski et al. | |

FOREIGN PATENT DOCUMENTS

| | | | |
|---|---|---|---|
| CN | 1480111 A | 3/2004 | |
| CN | 1586432 A | 3/2005 | |
| CN | 101278866 A | 10/2008 | |
| CN | 101288597 | 10/2008 | A61B 17/56 |
| DE | 2306552 | 8/1974 | A61F 1/00 |
| DE | 3516743 | 11/1986 | A61F 2/36 |
| DE | 8909091 | 9/1989 | A61F 2/35 |
| DE | 44 34 539 | 4/1996 | A61F 2/38 |
| DE | 19803673 | 8/1999 | A61L 27/54 |
| DE | 19926083 | 12/2000 | A61L 27/54 |
| DE | 10135771 | 2/2003 | A61B 17/70 |
| EP | 0528084 | 2/1993 | A61F 2/30 |
| EP | 0600806 | 6/1994 | A61L 25/00 |
| EP | 0600806 B1 | 6/1994 | |
| EP | 0672397 | 9/1995 | A61F 2/38 |
| EP | 0681817 A1 | 11/1995 | |
| EP | 0 704 193 | 4/1996 | A61F 2/30 |
| EP | 0626156 | 7/1997 | A61F 2/38 |
| EP | 0613380 | 12/1999 | A61L 27/00 |
| EP | 1074229 | 2/2001 | A61F 2/38 |
| EP | 1077253 | 2/2001 | C12N 5/00 |
| EP | 1120087 | 8/2001 | A61B 17/06 |
| EP | 1129675 | 9/2001 | A61F 2/30 |
| EP | 0732091 | 12/2001 | A61F 2/38 |
| EP | 0896825 | 7/2002 | A61L 27/00 |
| EP | 0814731 | 8/2002 | A61F 2/30 |
| EP | 1234552 | 8/2002 | A61F 2/00 |
| EP | 1234555 | 8/2002 | A61F 2/30 |
| EP | 0809987 | 10/2002 | A61F 2/38 |
| EP | 0833620 | 10/2002 | A61K 9/22 |
| EP | 1327423 | 7/2003 | A61F 2/38 |
| EP | 1329205 | 7/2003 | A61F 2/38 |
| EP | 0530804 | 6/2004 | A61L 25/00 |
| EP | 1437101 | 7/2004 | A61F 2/08 |
| EP | 1070487 | 9/2005 | A61F 2/08 |
| EP | 1886640 | 2/2008 | A61B 19/00 |
| EP | 1886640 A1 | 2/2008 | |
| EP | 2324799 | 5/2011 | A61F 2/38 |
| EP | 2173260 | 1/2012 | A61B 17/15 |
| FR | 2589720 | 11/1985 | A61F 2/38 |
| FR | 2740326 | 4/1997 | A61F 2/38 |
| GB | 1451283 | 9/1976 | A61F 1/24 |
| GB | 2291355 | 1/1996 | A61F 2/38 |
| GB | 2304051 | 3/1997 | A61F 2/38 |
| GB | 2348373 | 10/2000 | A61F 2/38 |
| JP | 56-083343 | 7/1981 | A61F 1/03 |
| JP | 61-247448 | 11/1986 | A61F 2/30 |
| JP | 1-249049 | 10/1989 | A61F 2/38 |
| JP | 5-503644 | 6/1993 | |
| JP | 05-184612 | 7/1993 | A61F 2/30 |
| JP | 7-236648 | 9/1995 | A61F 2/28 |
| JP | 8-173465 | 7/1996 | A61F 2/38 |
| JP | 8-506042 A | 7/1996 | |
| JP | 9-108249 A | 4/1997 | |
| JP | 9-206322 | 8/1997 | A61F 2/36 |
| JP | 11-19104 | 1/1999 | A61F 2/28 |
| JP | 11-276510 | 10/1999 | A61F 2/28 |
| JP | 2007-521881 | 8/2007 | A61F 2/44 |
| WO | WO 87/02882 | 5/1987 | A61F 2/38 |
| WO | WO 90/09769 | 9/1990 | A61F 2/28 |
| WO | 92/03108 A1 | 3/1992 | |
| WO | WO 92/03108 | 3/1992 | A61F 2/38 |
| WO | WO 93/04710 | 3/1993 | A61L 25/00 |
| WO | WO 93/09819 | 5/1993 | A61L 27/00 |
| WO | WO 93/25157 | 12/1993 | A61B 17/56 |
| WO | WO 95/27450 | 10/1995 | A61F 2/38 |
| WO | WO 95/28688 | 10/1995 | G06T 15/00 |
| WO | WO 95/30390 | 11/1995 | A61F 2/38 |
| WO | WO 95/32623 | 12/1995 | A01N 1/02 |
| WO | WO 96/24302 | 8/1996 | A61B 17/90 |
| WO | WO 97/25942 | 7/1997 | A61F 2/32 |
| WO | 97/29703 A1 | 8/1997 | |
| WO | WO 97/27885 | 8/1997 | A61L 27/00 |
| WO | WO 97/29703 | 8/1997 | A61B 17/56 |
| WO | WO 97/38676 | 10/1997 | A61K 9/10 |
| WO | WO 97/46665 | 12/1997 | C12N 5/06 |
| WO | WO 98/08469 | 3/1998 | A61F 2/30 |
| WO | WO 98/12994 | 4/1998 | A61F 2/28 |
| WO | WO 98/20816 | 5/1998 | A61F 2/38 |
| WO | WO 98/30617 | 7/1998 | C08G 63/12 |
| WO | WO 98/52498 | 11/1998 | A61F 2/28 |
| WO | WO 99/02654 | 1/1999 | C12N 5/00 |
| WO | WO 99/08598 | 2/1999 | A61B 8/00 |
| WO | WO 99/08728 | 2/1999 | A61L 27/00 |
| WO | WO 99/42061 | 8/1999 | A61F 2/38 |
| WO | WO 99/47186 | 9/1999 | A61L 27/00 |
| WO | WO 99/51719 | 10/1999 | C12M 3/00 |
| WO | WO 00/09179 | 2/2000 | A61L 25/00 |
| WO | WO 00/13616 | 3/2000 | |
| WO | WO 00/15153 | 3/2000 | A61F 2/38 |
| WO | WO 00/19911 | 4/2000 | A61B 17/02 |
| WO | WO 00/35346 | 6/2000 | A61B 5/11 |
| WO | WO 00/48550 | 8/2000 | |
| WO | WO 00/59411 | 10/2000 | A61F 2/38 |
| WO | WO 00/68749 | 11/2000 | G05B 19/4099 |
| WO | WO 00/74554 | 12/2000 | |
| WO | WO 00/74741 | 12/2000 | A61L 27/00 |
| WO | WO 00/76428 | 12/2000 | A61F 2/38 |
| WO | WO 01/10356 | 2/2001 | A61F 2/46 |
| WO | WO 01/17463 | 3/2001 | A61F 2/30 |
| WO | WO 01/19254 | 3/2001 | A61B 17/00 |
| WO | WO 01/35968 | 5/2001 | A61K 35/00 |
| WO | WO 01/45764 | 6/2001 | A61L 27/36 |
| WO | WO 01/68800 | 9/2001 | C12M 3/00 |
| WO | WO 01/70142 | 9/2001 | A61F 2/38 |
| WO | WO 01/77988 | 10/2001 | G06F 19/00 |
| WO | WO 01/82677 | 11/2001 | |
| WO | WO 01/91672 | 12/2001 | A61F 2/36 |
| WO | WO 02/02021 | 1/2002 | A61B 17/56 |
| WO | WO 02/09623 | 2/2002 | A61F 2/38 |
| WO | WO 02/22013 | 3/2002 | A61B 5/55 |
| WO | WO 02/22014 | 3/2002 | A61B 5/55 |
| WO | WO 02/23483 | 3/2002 | A61B 5/55 |
| WO | WO 02/34310 | 5/2002 | A61L 31/04 |
| WO | WO 02/36147 | 5/2002 | A61K 31/04 |
| WO | WO 02/37423 | 5/2002 | G06T 17/00 |
| WO | WO 02/061688 | 8/2002 | G06T 17/00 |
| WO | WO 02/096268 | 12/2002 | |
| WO | WO 03/007788 | 1/2003 | |
| WO | WO 03/013373 | 2/2003 | A61B 17/17 |
| WO | WO 03/037192 | 5/2003 | A61B 17/15 |
| WO | WO 03/039377 | 5/2003 | A61B 17/15 |
| WO | WO 03/047470 | 6/2003 | A61F 2/34 |
| WO | WO 03/051210 | 6/2003 | A61B 17/58 |
| WO | WO 03/061522 | 7/2003 | |
| WO | WO 03/099106 | 12/2003 | |
| WO | WO 2004/006811 | 1/2004 | A61F 2/46 |
| WO | WO 2004/032806 | 4/2004 | A61F 2/30 |
| WO | WO 2004/043305 | 5/2004 | A61F 2/30 |
| WO | WO 2004/049981 | 6/2004 | A61F 2/46 |
| WO | WO 2004/051301 | 6/2004 | G01R 33/56 |
| WO | WO 2004/073550 | 9/2004 | |
| WO | WO 2005/002473 | 1/2005 | A61F 2/38 |
| WO | WO 2005/016175 | 2/2005 | |
| WO | WO 2005/020850 | 3/2005 | |
| WO | WO 2005/051239 | 6/2005 | A61F 2/08 |
| WO | WO 2005/051240 | 6/2005 | A61F 2/08 |
| WO | WO 2005/067521 | 7/2005 | |

(56) References Cited

FOREIGN PATENT DOCUMENTS

| | | | |
|---|---|---|---|
| WO | WO 2005/076974 | 8/2005 | |
| WO | WO 2006/012370 | 2/2006 | ............ B65D 45/04 |
| WO | WO 2006/058057 | 6/2006 | ............... A61F 2/38 |
| WO | WO 2006/060795 | 6/2006 | ............ A61B 17/17 |
| WO | WO 2006/065774 | 6/2006 | ............... A61F 2/44 |
| WO | WO 2006/092600 | 9/2006 | ............ A61B 19/00 |
| WO | WO 2007/041375 | 4/2007 | ............... A61F 2/38 |
| WO | WO 2007/062079 | 5/2007 | ............... A61F 2/30 |
| WO | WO 2007/092841 | 8/2007 | ............ A61B 17/15 |
| WO | WO 2007/106172 | 9/2007 | ............... A61F 2/38 |
| WO | WO 2007/109641 | 9/2007 | ............... A61F 2/30 |
| WO | 2007/119173 A2 | 10/2007 | |
| WO | WO 2008/021494 | 2/2008 | ............ G06F 19/00 |
| WO | WO 2008/055161 | 5/2008 | ............... A61F 2/44 |
| WO | WO 2008/101090 | 8/2008 | ............... A61F 2/38 |
| WO | WO 2008/117028 | 10/2008 | ............ A61B 17/15 |
| WO | WO 2008/157412 | 12/2008 | ............ A61B 17/17 |
| WO | WO 2009/068892 | 6/2009 | ............... A61C 9/00 |
| WO | 2009/105495 A1 | 8/2009 | |
| WO | WO 2009/140294 | 11/2009 | ............... A61F 2/30 |
| WO | WO 2010/099231 | 9/2010 | ............ A61B 2/38 |
| WO | WO 2010/099353 | 9/2010 | ............... A61F 2/30 |
| WO | WO 2010/099359 | 9/2010 | ............... A61F 2/00 |
| WO | WO 2010/140036 | 12/2010 | ............... A61F 2/38 |
| WO | WO 2010/151564 | 12/2010 | ............... A61F 2/38 |
| WO | 2011/028624 A1 | 3/2011 | |
| WO | WO 2011/028624 | 3/2011 | ............... A61F 2/38 |
| WO | 2011/056995 A2 | 5/2011 | |
| WO | WO 2011/056995 | 5/2011 | ............... A61F 2/38 |
| WO | 2011/072235 A2 | 6/2011 | |
| WO | WO 2011/072235 | 6/2011 | ............... A61F 2/38 |
| WO | WO 2011/075697 | 6/2011 | ............... A61F 2/46 |
| WO | WO 2011/101474 | 8/2011 | ............ G06F 19/00 |
| WO | WO 2012/027150 | 3/2012 | ............ G06F 19/00 |
| WO | WO 2012/027185 | 3/2012 | ............ G06T 17/00 |
| WO | WO 2012/112694 | 8/2012 | ............... A61B 6/00 |
| WO | WO 2012/112698 | 8/2012 | ............... A61F 2/30 |
| WO | WO 2012/112701 | 8/2012 | ............... A61F 2/30 |
| WO | WO 2012/112702 | 8/2012 | ............... A61F 2/30 |
| WO | 2013/020026 A1 | 2/2013 | |
| WO | WO 2013/020026 | 2/2013 | ............... A61F 2/30 |
| WO | WO 2013/025814 | 2/2013 | ............... A61F 2/38 |
| WO | WO 2013/056036 | 4/2013 | ............... A61F 2/38 |
| WO | WO 2013/131066 | 9/2013 | ............... A61F 2/38 |
| WO | WO 2013/152341 | 10/2013 | ............... A61F 2/38 |
| WO | WO 2014/035991 | 3/2014 | ............ A61B 17/56 |
| WO | WO 2014/047514 | 3/2014 | ............... A61F 2/76 |
| WO | 2014/152533 A1 | 9/2014 | |
| WO | WO 2014/150428 | 9/2014 | ............ G06F 19/00 |
| WO | WO 2014/152533 | 9/2014 | ............... A61F 2/38 |
| WO | WO 2014/153530 | 9/2014 | ............... A61F 2/34 |

OTHER PUBLICATIONS

Adam et al., "MR Imaging of the Knee: Three-Dimensional Volume Imaging Combined with Fast Processing," J. Compt. Asst. Tomogr., 13(6): 984-988 (1989).

Adams et al., "Quantitative Imaging of Osteoarthritis," Semin Arthritis Rheum, 20(6) Suppl. 2: 26-39 (Jun. 1991).

Ahmad et al., "Biomechanical and Topographic Considerations for Autologous Osteochondral Grafting in the Knee," Am J Sports Med, 29(2): 201-206 (Mar.-Apr. 2001).

Alexander, "Estimating the motion of bones from markers on the skin," University of Illinois at Chicago (Doctoral Dissertation) (1998).

Alexander et al., "Correcting for deformation in skin-based marker systems," Proceedings of the 3rd Annual Gait and Clinical Movement Analysis Meeting, San Diego, CA (1998).

Alexander et al., "Internal to external correspondence in the analysis of lower limb bone motion," Proceedings of the 1999 ASME Summer Bioengineering Conference, Big Sky, Montana (1999).

Alexander et al., "State estimation theory in human movement analysis," Proceedings of the ASME International Mechanical Engineering Congress (1998).

Alexander et al., "Optimization techniques for skin deformation correction," International Symposium on 3-D Human Movement Conference, Chattanooga, TN, (1998).

Alexander et al., "Dynamic Functional Imaging of the Musculoskeletal System," ASME Winter International Congress and Exposition, Nashville, TN (1999).

Allen et al., "Late degenerative changes after meniscectomy 5 factors affecting the knee after operations," J Bone Joint Surg 66B: 666-671 (1984).

Alley et al., "Ultrafast contrast-enhanced three dimensional MR Aagiography: State of the art," Radiographics 18: 273-285 (1998).

Andersson et al., "MacIntosh Arthroplasty in Rheumatoid Arthritis," Acta. Orthrop. Scand. 45(2):245-259 (1974).

Andriacchi, "Dynamics of knee Malalignment," Orthop Clin North Am 25: 395-403 (1994).

Andriacchi, et al., "A point cluster method for in vivo motion analysis: Applied to a study of knee kinematics," J. Biomech Eng 120(12): 743-749 (1998).

Andriacchi, et al., "Methods for evaluating the progression of Osterarthiritis," Journal of Rehabilitation Research and Development 37(2): 163-170 (2000).

Andriacchi et al., "Gait analysis as a tool to assess joint kinetics biomechanics of normal and pathological human articulating joints," Nijhoff, Series E 93: 83-102 (1985).

Andriacchi et al., "In vivo measurement of six-degrees-of-freedom knee movement during functional testing," Transactions of the Orthopedic Research Society 698 (1995).

Argenson et al., "Is There a Place for Patellofemoral Arthroplasty?," Clinical Orthopaedics and Related Research No. 321, pp. 162-167 (1995).

Aro et al., "Clinical Use of Bone Allografts," Ann Med 25:403-412 (1993).

Bashir, "Validation of Gadolinium-Enhanced MRI of FAF Measurement in Human Cartilage," Intl. Soc. Mag. Resonance Med. (1998).

Beaulieu et al., "Glenohumeral relationships during physiological shoulder motion and stress testing: Initial experience with open MRI and active Scan-25 plane registration," Radiology (1999).

Beaulieu et al., "Dynamic imaging of glenohumeral instability with open MRI," Int. Society for Magnetic Resonance in Medicine Sydney, Australia (1998).

Beckmann et al., "Noninvasive 3D MR Microscopy as Tool in Pharmacological Research: Application to a Model of Rheumatoid Arthritis," Magn Reson Imaging 13(7): 1013-1017 (1995).

Billet, Philippe, French Version—"Gliding Knee Prostheses—Analysis of Mechanical Failures", Thesis, Medical School of Marseilles, 1982, 64 pages.

Billet, Philippe, Translated Version—"Gliding Knee Prostheses—Analysis of Mechanical Failures", Thesis, Medical School of Marseilles, 1982, 93 pages.

Blazina et al., "Patellofemoral replacement: Utilizing a customized femoral groove replacement," 5(1)53-55 (1990).

Blum et al., "Knee Arthroplasty in Patients with Rheumatoid Arthritis," Ann. Rheum. Dis. 33 (1): 1-11 (1974).

Bobic, "Arthroscopic osteochondral autogaft transplantation in anterior cruciate ligament reconstruction: a preliminary clinical study," Knee Surg Sports Traumatol Arthrosc 3(4): 262-264 (1996).

Boe et al., "Arthroscopic partial meniscectomy in patients aged over 50," J. Bone Joint Surg 68B: 707 (1986).

Bogoch, et al., "Supracondylar Fractures of the Femur Adjacent to Resurfacing and MacIntosh Arthroplasties of the Knee in Patients with Rheumatoid Arthritis," Clin. Orthop. (229):213-220 (Apr. 1988).

Borthakur et al., "In Vivo Triple Quantum Filtered Sodium MRI of Human Articular Cartilage," Proc. Intl. Soc. Mag. Resonance Med., 7:549 (1999).

Brandt et al., In German: "CRIGOS—Development of a Compact Robot System for Image-Guided Orthopedic Surgery," Der Orthopäde, Springer-Verlag, vol. 29, No. 7, pp. 645-649 (Jul. 2000).

(56) References Cited

OTHER PUBLICATIONS

Brandt et al., English Translation with Certification: "CRIGOS—Development of a Compact Robot System for Image-Guided Orthopedic Surgery," *Der Orthopäde*, Springer-Verlag, vol. 29, No. 7, pp. 645-649 (Jul. 2000).
Bregler et al., "Recovering non-rigid 3D shape from image streams," Proc. IEEE Conference on Computer Vision and Pattern Recognition (Jun. 2000).
Brett et al., "Quantitative Analysis of Biomedical Images," Univ. of Manchester, Zeneca Pharmaceuticals, IBM UK, http://www.wiau.man.ac.uk/~ads/imv (1998).
Brittberg et al., "A critical analysis of cartilage repair," Acta Orthop Scand 68(2): 186-191 (1997).
Brittberg et al., "Treatment of deep cartilage defects in the knee with autologous chrondrocyte transplantation," N Engl J Med 331(14): 889-895 (1994).
Broderick et al., "Severity of articular cartilage abnormality in patients with osteoarthritis: evaluation with fast spin-echo MR vs. arthroscopy," AJR 162: 99-103 (1994).
Brown, Ph.D., et al., "MRI Basic Principles and Applications", Second Ed., Mark A. Brown and Richard C. Semelka, 1999, Wiley-Liss Inc., Title page and Table of Contents Pages Only (ISBN 0471330620).
Burgkart et al., "Magnetic Resonance Imaging-Based Assessment of Cartilage Loss in Severe Osteoarthritis," Arth Rheum; 44(9): 2072-2077 (Sep. 2001).
Butterworth et al., "A T1O2 Dielectric-Filled Toroidal Resonator," Depts of Biomedical Engineering, Medicine, Neurology, & Center for Nuclear Imaging Research, U. of Alabama at Birmingham, USA, 1 Page (1999).
Butts et al., "Real-Time MR imaging of joint motion on an open MR imaging scanner," Radiological Society of North America, 83rd Scientific Assembly and Annual Meeting, Chicago, IL (1997).
Cameron, et al., "Review of a Failed Knee Replacement and Some Observations on the Design of a Knee Resurfacing Prosthesis," Arch. Orthop Trauma Surg. 97(2):87-89 (1980).
Caos, "MIS meets CAOS Spring 2005 Symposium Schedule", *CAOS Spring 2005 Symposium*, pp. 1-9, May 19, 2005.
Carano et al., "Estimation of Erosive Changes in Rheumatoid Arthritis by Temporal Multispectral Analysis," Proc. Intl. Soc. Mag. Resonance Med., 7:408 (1999).
Carr et al., "Surface Interpolation with Radial Basis Functions for Medical Imaging," IEEE Transactions on Medical Imaging, IEEE, Inc. New York, vol. 16, pp. 96-107 (Feb. 1997).
Castriota-Scanderbeg et al., "Precision of Sonographic Measurement of Articular Cartilage: Inter-and Intraobserver Analysis," Skeletal Radiol 25: 545-549 (1996).
Chan et al., "Osteoarthritis of the Knee: Comparison of Radiography, CT and MR Imaging to Asses Extent and Severity," AJR Am J Roentgenol 157(4): 799-806 (1991).
Chelule et al., "Patient-Specific Template to Preserve Bone Stock in Total Knee Replacement: Preliminary Results", *15th Annual ISTA Symposium*, Sep. 2002, 1 page.
Clarke et al., "Human Hip Joint Geometry and Hemiarthroplasty Selection," The Hip. C.V. Mosby, St. Louis 63-89 (1975).
Clary et al., "Experience with the MacIntosh Knee Prosthesis," South Med. J. 65(3):265-272 (1972).
Cohen et al., "Knee cartilage topography, thickness, and contact areas from MRI: in-vitro calibration and in-vivo measurements," Osteoarthritis and Cartilage 7: 95-109 (1999).
Conaty, et al., "Surgery of the Hip and Knee in Patients with Rheumatoid Arthritis," J. Bone Joint Surg. Am. 55(2):301-314 (1973).
Creamer et al., "Quantitative Magnetic Resonance Imaging of the Knee: A Method of Measuring Response to Intra-Articular Treatments," Ann Rheum Dis. 378-381 (1997).
Daniel et al., "Breast cancer-gadolinium-enhanced MR imaging with a 0.5T open imager and three-point Dixon technique," Radiology 207(1): 183-190 (1998).

Dardzinski et al., "Entropy Mapping of Articular Cartilage", ISMRM Seventh Scientific Meeting, Philadelphia, PA (1999) T. 41, V. II.
Dardzinski et al., "T1-T2 Comparison in Adult Articular Cartilage," ISMRM Seventh Scientific Meeting, Philadelphia, PA (May 22-28, 1999).
Delp et al., Graphics-Based Software System to Develop and Analyze Models of Musculoskeletal Structures, Comput. Biol. Med., vol. 25, No. 1, pp. 21-34, 1995.
De Winter et al., "The Richards Type II Patellofemoral Arthroplasty", Acta Orthop Scand 2001; 72 (5): 487-490.
Disler, "Fat-suppressed three-dimensional spoiled gradient-recalled MR imaging: assessment of articular and physeal hyaline cartilage," AJR 169: 1117-1123 (1997).
Disler et al., "Fat-suppressed three-dimensional spoiled gradient-echo MR imaging of hyaline cartilage defects in the knee: comparison with standard MR imaging and arthroscopy," AJR 167: 127-132 (1996).
Disler et al., "Detection of knee hyaline cartilage defects using fat-suppressed three-dimensional spoiled gradient-echo MR imaging: comparison with standard MR imaging and correlation with arthroscopy," AJR 165: 377-382 (1995).
Doherty et al., Osteoarthritis, Oxford Textbook of Rheumatology, Oxford University Press 959-983 (1993).
Dougados et al., "Longitudinal radiologic evaluation of osteoarthritis of the knee," J Rheumatol 19: 378-384 (1992).
Du et al., "Vessel enhancement filtering in three-dimensional MR angiography," J. Magn Res Imaging 5: 151-157 (1995).
Du et al., "Reduction of partial-volume artifacts with zero filled interpolation in three-dimensional MR Angiography," J Magn Res Imaging 4: 733-741 (1994).
Dufour et al., "A Technique for the Dynamical Evaluation of the Acromiohumeral Distance of the Shoulder in the Seated Position under Open-field MRI," Proc. Intl. Soc. Mag. Resonance Med., 7:406 (1999).
Dumoulin et al., "Real-time position monitoring of invasive devises using magnetic resonance," Magn Reson Med 29: 411-5 (1993).
Dupuy et al., "Quantification of Articular Cartilage in the Knee with Three-Dimensional MR Imaging," Acad Radiol 3: 919-924 (1996).
Eckstein et al., "Determination of Knee Joint Cartilage Thickness Using Three-Dimensional Magnetic Resonance Chondro-Crassometry (3D MR-CCM)," Magn. Reson. Med. 36(2):256-265, (1996).
Eckstein et al., "Effect of Gradient and Section Orientation on Quantitative Analyses of Knee Joint Cartilage," Journal of Magnetic Resonance Imaging 11: 161-167 (2000).
Eckstein et al., "Effect of Physical Exercise on Cartilage Volume and Thickness In Vivo: An MR Imaging Study," Radiology 207: 243-248 (1998).
Eckstein et al., "Functional Analysis of Articular Cartilage Deformation, Recovery, and Fluid Flow Following Dynamic Exercise In Vivo," Anatomy and Embryology 200: 419-424 (1999).
Eckstein et al., "In Vivo Reproducibility of Three-Dimensional Cartilage Volume and Thickness Measurements With MR Imaging", AJR 170(3): 593-597 (1998).
Eckstein et al., "New Quantitative Approaches With 3-D MRI: Cartilage Morphology, Function and Degeneration", Medical Imaging International, Nov.-Dec. 1998.
Eckstein et al., "Side Differences of Knee Joint Cartilage Volume, Thickness, and Surface Area, and Correlation With Lower Limb Dominance—An MRI-Based Study," Osteoarthritis and Cartilage 10: 914-921 (2002).
Eckstein et al., Accuracy of Cartilage Volume and Thickness Measurements with Magnetic Resonance Imaging, Clin. Orthop. 1998; 352: 137-148 T. 60 V. II.
Eckstein et al., "Magnetic Resonance Chondro-Crassometry (MR CCM): A Method for Accurate Determination of Articular Cartilage Thickness?" Magn. Reson. Med. 35: 89-96 (1996).
Eckstein et al., "The Influence of Geometry on the Stress Distribution in Joints—A Finite Element Analysis," Anat Embryol, 189: 545-552 (1994).

(56) References Cited

OTHER PUBLICATIONS

Eckstein et al., "The Morphology of Articular Cartilage Assessed by Magnetic Resonance Imaging: Reproducibility and Anatomical Correlation," Sur. Radiol Anat 16: 429-438 (1994).
Elting et al., "Unilateral frame distraction: proximal tibial valgus osteotomy for medial gonarthritis," Contemp Orthrop 27(6): 522-524 (1993).
Faber et al., "Gender Differences in Knee Joint Cartilage Thickness, Volume and Articular Surface Areas: Assessment With Quantitative Three-Dimensional MR Imaging," Skeletal Radiology 30 (3): 144-150 (2001).
Faber et al., "Quantitative Changes of Articular Cartilage Microstructure During Compression of an Intact Joint," Proc. Intl. Soc. Mag. Resonance Med., 7:547 (1999).
Falcao et al., "User-steered image segmentation paradigms: Live wire and live lane," Graphical Models and Image Processing 60: 233-260 (1998).
Felson et al., "Weight Loss Reduces the risk for symptomatic knee osteoarthritis in women: the Framingham study," Ann Intern Med 116: 535-539 (1992).
Gandy et al., "One-Year Longitudinal Study of Femoral Cartilage Lesions in Knee Arthritis," Proc. Intl. Soc. Mag. Resonance Med., 7:1032 (1999).
Garrett, "Osteochondral allografts for reconstruction of articular defects of the knee," Instr Course Lect 47: 517-522 (1998).
Gerscovich, "A Radiologist's Guide to the Imaging in the Diagnosis and Treatment of Developmental Dysplasia of the Hip," Skeletal Radiol 26: 447-456 (1997).
Ghelman et al., "Kinematics of the Knee After Prosthetic Replacements", Clin. Orthop. May 1975: (108): 149-157.
Ghosh et al., "Watershed Segmentation of High Resolution Articular Cartilage Images for Assessment of Osteoarthritis," International Society for Magnetic Resonance in Medicine, Philadelphia, (1999).
Glaser et al., "Optimization and Validation of a Rapid Highresolution T1-W 3-D Flash Waterexcitation MR Sequ ence for the Quantitative Assessment of Articular Cartilage Volume and Thickness," Magnetic Resonance Imaging 19: 177-185 (2001).
Goodwin et al., "MR Imaging of Articular Cartilage: Striations in the Radial Layer Reflect the Fibrous Structure of Cartilage," Proc. Intl. Soc. Mag. Resonance Med., 7:546 (1999).
Gouraud, "Continuous shading of curved surfaces," IEEE Trans on Computers C-20(6) (1971).
Graichen et al., "Three-Dimensional Analysis of the Width of the Subacromial Space in Healthy Subjects and Patients With Impingement Syndrome," American Journal of Roentgenology 172: 1081-1086 (1999).
Hafez et al., "Computer Assisted Total Knee Replacement: Could a Two-Piece Custom Template Replace the Complex Conventional Instrumentations?" Session 6: Novel Instruments; *Computer Aided Surgery*, Session 6, vol. 9, No. 3, pp. 93-94 (Jun. 2004).
Hafez et al., "Computer-assisted Total Knee Arthroplasty Using Patient-specific Templating," *Clinical Orthopaedics and Related Research*, No. 444, pp. 184-192 (Mar. 2006).
Hall et al., "Quantitative MRI for Clinical Drug Trials of Joint Diseases; Virtual Biopsy of Articular Cartilage" NIH-FDA Conf. on Biomarkers and Surrogate Endpoints: Advancing Clinical Research and Applications (1998).
Hardy et al., "Measuring the Thickness of Articular Cartilage From MR Images," J. Magnetic Resonance Imaging 13: 120-126 (2001).
Hardy et al., "The Influence of the Resolution and Contrast on Measuring the Articular Cartilage Volume in Magnetic Resonance Images" Magn Reson Imaging. 18(8): 965-972 (Oct. 2000).
Hargreaves et al., "MR Imaging of Articular Cartilage Using Driven Equilibrium," Magnetic Resonance in Medicine 42(4): 695-703 (Oct. 1999).
Hargreaves et al., "Technical considerations for DEFT imaging," International Society for Magnetic Resonance in Medicine, Sydney, Australia (Apr. 17-24, 1998).
Hargreaves et al., "Imaging of articular cartilage using driven equilibrium," International Society for Magnetic Resonance in Medicine, Sydney, Australia (Apr. 17-24, 1998).
Hastings et al., "Double Hemiarthroplasty of the Knee in Rheumatoid Arthritis," A Survey of Fifty Consecutive Cases, J. Bone Joint Surg. Br. 55(1):112-118 (1973).
Haubner M, et al., "A Non-Invasive Technique for 3-Dimensional Assessment of Articular Cartilage Thickness Based on MRI Part @: Validation Using CT Arthrography," Magn Reson Imaging; 15(7): 805-813 (1997).
Haut et al., "A High Accuracy Three-Dimensional Coordinate Digitizing System for Reconstructing the Geometry of Diarthrodial Joints," J. Biomechanics 31: 571-577 (1998).
Hayes et al., "Evaluation of Articular Cartilage: Radiographic and Cross-Sectional Imaging Techniques," Radiographics 12: 409-428 (1992).
Henderson et al., "Experience with the Use of the Macintosh Prosthesis in Knees of Patients with Pheumatoid Arthritis," South. Med. J. 62(11):1311-1315 (1969).
Henkelman, "Anisotropy of NMR Properties of Tissues", Magn Res Med. 32: 592-601 (1994).
Herberhold et al., "An MR-Based Technique for Quantifying the Deformation of Articular Cartilage During Mechanical Loading in an Intact Cadaver Joint," Magnetic Resonance in Medicine 39(5): 843-850 (1998).
Herberhold, "In Situ Measurement of Articular Cartilage Deformation in Intact Femorapatellar Joints Under Static Loading", Journal of biomechanics 32: 1287-1295 (1999).
Herrmann et al., "High Resolution Imaging of Normal and Osteoarthritic Cartilage with Optical Coherence Tomogrqaphy," J. Rheumatoil 26: 627-635 (1999).
High et al., "Early Macromolecular Collagen Changes in Articular Cartilage of Osteoarthritis (OA): An In Vivo MT-MRI and Histopathologic Study," Proc. Intl. Soc. Mag. Resonance Med., 7:550 (1999).
Hohe, "Surface Size, Curvature Analysis, and Assessment of Knee Joint Incongruity With MR Imaging In Vivo", Magnetic Resonance in Medicine, 47: 554-561 (2002).
Holdsworth et al., "Benefits of Articular Cartilage Imaging at 4 Tesla: An In Vivo Study of Normal Volunteers," Proc. Intl. Soc. Mag. Resonance Med., 7:1028 (1999).
Hughes et al., "Technical Note: A Technique for Measuring the Surface Area of Articular Cartilage in Acetabular Fractures," Br. J. Radiol; 67: 584-588 (1994).
Husmann et al., "Three-Dimensional Morphology of the Proximal Femur," J. Arthroplasty; 12(4): 444-450 (Jun. 1997).
Hyhlik-Durr et al., "Precision of Tibial Cartilage Morphometry with a coronal water-excitation MR sequence," European Radiology 10(2): 297-303 (2000).
Ihara H., "Double-Contrast CT Arthrography of the Cartilage of the Patellofemoral Joint," Clin. Orthop.; 198: 50-55 (Sep. 1985).
Iida et al., "Socket L ocation in Total Hip Replacement: Preoperative Computed Tomography and Computer Simulation" Acta Orthop Scand; 59(1): 1-5 (1998).
Irarrazabal et al., "Fast three-dimensional magnetic resonance imaging," Mag Res. Med. 33: 656-662 (1995).
Jessop et al., "Follow-up of the MacIntosh Arthroplasty of the Knee Joint," Rheumatol Phys. Med. 11(5):217-224 (1972).
Johnson et al., "The distribution of load across the knee. A comparison of static and dynamic measurements," J. Bone Joint Surg 62B: 346-349 (1980).
Johnson, "In vivo contact kinematics of the knee joint: Advancing the point cluster technique," Ph.D. Thesis, University of Minnesota (1999).
Johnson et al., "Development of a knee wear method based on prosthetic in vivo slip velocity," Transaction of the Orthopedic Research Society, 46th Annual Meeting (Mar. 2000).
Jonsson et al., "Precision of Hyaline Cartilage Thickness Measurements," Acta Radiol 1992; 33(3): 234-239 (1992).
Kaneuji et al., "Three Dimensional Morphological Analysis of the Proximal Femoral Canal, Using Computer-Aided Design System, in Japanese Patients with Osteoarthrosis of the Hip," J. Orthop Sci; 5(4): 361-368 (2000).

(56) References Cited

OTHER PUBLICATIONS

Karvonen et al., "Articular Cartilage Defects of the Knee: Correlation Between Magnetic Resonance Imaging and Gross Pathology," Ann Rheum Dis. 49: 672-675 (1990).
Kass et al., "Snakes: Active contour models.," Int J Comput Vision 1: 321-331 (1988).
Kates, et al., "Experiences of Arthroplasty of the Rheumatoid Knee Using MacIntosh Prostheses," Ann. Rheum. Dis. 28(3):328 (1969).
Kaufman et al., "Articular Cartilage Sodium content as a function of compression" Seventh Scientific Meeting of ISMRM, p. 1022, 1999 T. 105, V. III.
Kay et al., The MacIntosh Tibial Plateau Hemiprosthesis for the Rheumatoid Knee, J. Bone Joint Surg. Br. 54(2):256-262 (1972).
Kidder et al., "3D Model Acquisition, Design, Planning and Manufacturing of Orthopaedic Devices: A Framework," Proceedings of the SPIE—Advanced Sensor and Control-System Interface, Boston, MA, vol. 2911, pp. 9-22, 21 (Nov. 1996).
Klosterman et al., "T2 Measurements in Adult Patellar Cartilage at 1.5 and 3.0 Tesla," ISMRM Seventh Scientific Meeting, Philadelphia, PA, (May 22-28, 1999).
Knauss et al., "Self-Diffusion of Water in Cartilage and Cartilage Components as Studied by Pulsed Field Gradient NMR," Magnetic Resonance in Medicine 41:285-292 (1999).
Koh et al., "Visualization by Magnetic Resonance Imaging of Focal Cartilage Lesions in the Excised Mini-Pig Knee," J. Orthop. Res; 14(4): 554-561 (Jul. 1996).
Korhonen et al., "Importance of the Superficial Tissue Layer for the Indentation Stiffness of Articular Cartilage," Med. Eng. Phys; 24(2): 99-108 (Mar. 2002).
Korkala et al., "Autogenous Osteoperiosteal Grafts in the Reconstruction of Full-Thickness Joint Surface Defects," Int. Orthop.; 15(3): 233-237 (1991).
Kshirsagar et al., "Measurement of Localized Cartilage Volume and Thickness of Human Knee Joints by Computer Analysis of Three-Dimensional Magnetic Resonance Images," Invest Radiol. 33(5): 289-299 (May 1998).
Kwak et al., "Anatomy of Human Patellofemoral Joint Articular Cartilage: Surface Curvature Analysis," J. Orthop. Res.; 15: 468-472 (1997).
LaFortune et al., "Three dimensional kinematics of the human knee during walking," J. Biomechanics 25: 347-357 (1992).
Lam et al., "X-Ray Diagnosis: A Physician's Approach", Editor Lam, 1998, Springer-Verlag publishers, Title page and Index Only (ISBN 9813083247).
Lang et al., "Functional joint imaging: a new technique integrating MRI and biomotion studies," International Society for Magnetic Resonance in Medicine, Denver (Apr. 18-24, 2000).
Lang et al., Risk factors for progression of cartilage loss: a longitudinal MRI study. European Society of Musculoskeletal Radiology, 6th Annual Meeting, Edinburgh, Scotland (1999).
Lang et al., Cartilage imaging: comparison of driven equilibrium with gradient-echo, SPAR, and fast spin-echo sequences. International Society for Magnetic Resonance in Medicine, Sydney, Australia, (Apr. 17-24, 1998).
Ledingham et al., "Factors affecting radiographic progression of knee osteoarthritis," Ann Rheum Dis 54: 53-58 (1995).
Leenslag et al., "A Porous Composite for Reconstruction of Meniscus Lesions," Biological and Biomechanical Perform. of Biomaterials, Elsevier Science Publishers Amsterdam pp. 147-152 (1986).
Lefebvre et al., "Automatic Three-Dimensional Reconstruction and Characterization of Articular Cartilage from High-Resolution Ultrasound Acquisitions," Ultrasound Med. Biol.; 24(9): 1369-1381 (Nov. 1998).
Li et al., A Boundary Optimization Algorithm for Delineating Brain Objects from CT Scans: Nuclear Science Symposium and Medical Imaging Conference 1993 IEEE Conference Record, San Francisco, CA (1993).
Lin et al., "Three-Dimensional Characteristics of Cartilagenous and Bony Components of Dysplastic Hips in Children: Three-Dimensional Computed Tomography Quantitative Analysis," J. Pediatr. Orthop.; 17: 152-157 (1997).
Lorensen et al., "Marching cubes: a high resolution 3d surface construction algorithm," Comput Graph 21: 163-169 (1987).
Losch et al., "A non-invasive technique for 3-dimensional assessment of articular cartilage thickness based on MRI part 1: development of a computational method," Magn Res Imaging 15(7): 795-804 (1997).
Lu et al., "Bone position estimation from skin marker co-ordinates using globals optimization with joint constraints," J Biomechanics 32: 129-134 (1999).
Lu et al., "In vitro degradation of porous poly(L-lactic acid) foams", Biomaterials, 21(15):1595-1605, Aug. 2000.
Lucchetti et al., "Skin movement artifact assessment and compensation in the estimation of knee-joint kinematics," J Biomechanics 31: 977-984 (1998).
Lusse et al., "Measurement of Distribution of Water Content of Human Articular Cartilage Based on Transverse Relaxation Times: An In Vitro Study," Seventh Scientific Meeting of ISMRM, p. 1020 (1999).
Lynch et al., "Cartilage segmentation of 3D MRI scans of the osteoarthritic knee combining user knowledge and active contours," Proc. SPIE 3979 Medical Imaging, San Diego pp. 925-935 (Feb. 2000).
MacIntosh, "Arthroplasty of the Knee in Rheumatoid Arthritis," Proceedings and Reports of Councils and Assotions, J. Bone & Joint Surg., vol. 48B No. (1): 179 (Feb. 1996).
MacIntosh et al., "The Use of the Hemiarthroplasty Prosthesis for Advanced Osteoarthritis and Rheumatoid Arthritis of the Knee," J. of Bone & Joint Surg., vol. 54B, No. 2, pp. 244-255 (1972).
MacIntosh, "Arthroplasty of the Knee in Rheumatoid Arthritis Using the Hemiarthroplasty Prosthesis," Synovectomy and Arthroplasty in Rheumatoid Arthritis pp. 79-80, Second Int'l. Symposium, Jan. 27-29, 1967 (Basle, Switzerland).
MacIntosh, "Hemiarthroplasty of the Knee Using a Space Occupying Prosthesis for Painful Varus and Valgus Deformities," J. Bone Joint Surg. Am. Dec. 1958:40-A:1431.
Maki et al., "SNR improvement in NMR microscopy using DEFT," J Mag Res; pp. 482-492 (1988).
Marler et al., "Soft-Tissue Augmentation with Injectable Alginate and Syngeneic Fibroblasts", Plastic & Reconstructive Surgery, 105(6):2049-2058, May 2000.
Marshall et al., "Quantitation of Articular Cartilage Using Magnetic Resonance Imaging and Three-Dimensional Reconstruction," J. Orthop. Res.; 13: 814-823 (1995).
Matsen, III et al., "Robotic Assistance in Orthopaedic Surgery: A Proof of Principle Using Distal Femoral Arthroplasty", Clinical Ortho. and Related Research, 296:178-186 (1993).
Mattila et al., "Massive Osteoarticular Knee Allografts: Structural Changes Evaluated with CT," Radiology; 196: 657-660 (1995).
McCollum et al., "Tibial Plateau Prosthesis in Arthroplasty of the Knee," J. Bone Joint Surg. Am. 1970 52(4):827-8 (Feb. 1996).
McKeever, "The Classic Tibial Plateau Prosthesis," Clin. Orthop. Relat. Res. (192):3-12 (1985).
Merkle et al., "A Transceiver Coil Assembly for Hetero-Nuclear Investigations of Human Breast at 4T," Proc. Intl. Soc. Mag. Resonance Med., 7:170 (1999).
Meyer et al., "Simultaneous spatial and spectral selective excitation," Magn Res Med 15: 287-304 (1990).
Mills et al., "Magnetic Resonance Imaging of the Knee: Evaluation of Meniscal Disease," Curr. Opin. Radiol. 4(6): 77-82 (1992).
Milz et al., "The Thickness of the Subchondral Plate and Its Correlation with the thickness of the Uncalcified Articular Cartilage in the Human Patella," Anat. Embryol.; 192: 437-444 (1995).
Minas, "Chondrocyte Implantation in the Repair of Chondral Lesions of the Knee: Economics and Quality of Life", Am. J. Orthop. Nov. 1998; 27: 739-744.
Modest et al., "Optical Verification of a Technique for In Situ Ultrasonic Measurement of Articular Cartilage Thickness," J. Biomechanics 22(2): 171-176 (1989).

(56) References Cited

OTHER PUBLICATIONS

Mollica et al., "Surgical treatment of arthritic varus knee by tibial corticotomy and angular distraction with an external fixator," Ital J Orthrop Traumatol 18(1): 17-23 (1992).
Moussa, "Rotational Malalignment and Femoral Torsion in Osteoarthritic Knees with Patellofemoral Joint Imvolvement: A CT Scan Study," Clin. Orthop.; 304: 176-183 (Jul. 1994).
Mundinger et al., "Magnetic Resonance Tomography in the Diagnosis of Peripheral Joints," Schweiz Med. Wochenschr. 121(15): 517-527 (1991) (Abstract Only).
Myers et al., "Experimental Assessment by High Frequency Ultrasound of Articular Cartilage Thickness and Osteoarthritic Changes," J. Rheumatol; 22: 109-116 (1995).
Nelson et al., "Arthroplasty and Arthrodesis of the Knee Joint," Orthop. Clin. North Am. 2 (1): 245-64 (1971).
Nieminen et al., "T2 Indicates Incompletely the Biomechanical Status of Enzymatically Degraded Articular Cartilage of 9.4T," Proc. Intl. Soc. Mag. Resonance Med., 7:551 (1999).
Nishii et al., "Three Dimensional Evaluation of the Acetabular and Femoral Articular Cartilage in the Osteoarthritis of the Hip Joint," Proc. Intl. Soc. Mag. Resonance Med., 7:1030 (1999).
Nizard, "Role of tibial osteotomy in the treatment of medical femorotibial osteoarthritis," Rev Rhum Engl Ed 65(7-9): 443-446 (1998).
Noll et al., "Homodyne detection in magnetic resonance imaging," IEEE Trans Med Imag 10(2): 154-163 (1991).
Ogilvie-Harris et al., "Arthroscopic management of the degenerative knee," Arthroscopy 7: 151-157 (1991).
Parkkinen et al., "A Mechanical Apparatus With Microprocessor Controlled Stress Profile for Cyclic Compression of Cultured Articular Cartilage Explants," J. Biomech.; 22 (11-12): 1285-1290 (1989).
Pearle et al., "Use of an external MR-tracking coil for active scan plane registration during dynamic Musculoskeletal MR imaging in a vertically open MR unit," American Roentgen Ray Society, San Francisco, CA (1998).
Peterfy et al., "Quantification of the volume of articular cartilage in the carpophalangeal joints of the hand: accuracy and precision of three-dimensional MR imaging," AJR 165: 371-375 (1995).
Peterfy et al., "MR Imaging of the arthritic knee: improved discrimination of cartilage, synovium, and effusion with pulsed saturation transfer and fat-suppressed TI-weighted sequences," Radiology 191(2): 413-419 (1994).
Peterfy et al., "Quantification of articular cartilage in the knee with pulsed saturation transfer subtraction and fat-suppressed MR imaging: optimization and validation," Radiology 192(2): 485-491 (1994).
Peterfy et al., "Emerging Applications of Magnetic Resonance Imaging in the Evaluation of Articular Cartilage," Radiol Clin North Am.; 34(2): 195-213 (Mar. 1996).
Pilch et al., "Assessment of Cartilage Volume in the Femorotibial Joint With Magnetic Resonance Imaging and 3D Computer Reconstruction," J. Rheumatol. 21(12): 2307-2319 (1994).
Piplani et al., "Articular cartilage volume in the knee: semi-automated determination from three-dimensional reformations of MR images," Radiology 198: 855-859 (1996).
Platt et al., "Mould Arthroplasty of the Knee: A Ten-Yr Follow-up Study," Oxford Regional Rheumatic Diseases Resch. Ctre, J. of Bone & Joint Surg., vol. 51B, pp. 76-87 (1969).
Porter et al., "MacIntosh Arthroplasty: A Long-Term Review," J. R. Coll. Surg. Edin. (192):199-201 (1988).
Portheine et al., "CT-Based Planning and Individual Template Navigation in TKA", Navigation and Robotics in Total Joint and Spine Surgery, Springer, 48:336-342 (2004).
Portheine et al., "Development of a Clinical Demonstrator for Computer Assisted Orthopedic Surgery with CT Image Based Individual Templates." In Lemke HU, Vannier MW, Inamura K (eds). Computer Assisted Radiology and Surgery. Amsterdam, Elsevier 944-949, 1997.
Potter, "Arthroplasty of the Knee With Tibial Metallic Implants of the McKeever and MacIntosh Design," Sug. Clin. North Am. 49(4):903-915 (1969).
Potter et al., "Arthroplasty of the Knee in Rheumatoid Arthritis and Osteoarthritis: A Follow-up Study After Implantation of the McKeever and MacIntosh Prostheses," J. Bone Joint Surg. Am. 54(1):1-24 (1972).
Potter et al., "Magnetic resonance imaging of articular cartilage in the knee: an evaluation with use of fast-spin-echo imaging," J Bone Joint Surg 80-A(9): 1276-1284 (1998).
Potter et al., "Sensitivity of Quantitative NMR Imaging to Matrix Composition in Engineered Cartilage Tissue" Proc. Intl. Soc. Mag. Resonance Med., 7:552 (1999).
Probst et al., "Technique for Measuring the Area of Canine Articular Surfaces," Am. J. Vet. Res. 48(4): 608-609 (1987).
Prodromos et al., "A relationship between gait and clinical changes following high tibial osteotomy," J Bone Joint Surg 67A: 1188-1194 (1985).
Radermacher et al., "Computer Assisted Orthopedic Surgery by Means of Individual Templates •Aspects and Analysis of Potential Applications •" *Proceedings of the First International Symposium on Medical Robotics and Computer Assisted Surgery*, vol. 1: Sessions I-III, MRCAS '94, Pittsburgh, PA, pp. 42-48 (Sep. 22-24, 1994).
Radermacher, English Translation: Helmholtz Institute of Biomedical Technology, "Computer-Assisted Planning and Execution of Orthopedic Surgery Using Individual Surgical Templates", May 18, 1999.
Radermacher, German Version: Helmholtz Institute of Biomedical Technology, "Computer-Assisted Planning and Execution of Orthopedic Surgery Using Individual Surgical Templates", May 18, 1999.
Radermacher, "Computer Assisted Orthopaedic Surgery With Image Based Individual Templates" Clinical Orthopaedics, Sep. 1998, vol. 354, pp. 28-38.
Radermacher et al., "Image Guided Orthopedic Surgery Using Individual Templates—Experimental Results and Aspects of the Development of a Demonstrator for Pelvis Surgery." In Troccaz J. Grimson E., Mosges R (eds). Computer Vision, Virtual Reality and Robotics in Medicine and Medical Robotics and Computer Assisted Surgery, Lecture Notes in Computer Science. Berlin, Springer-Verlag 606-615, 1997.
Radermacher et al., "Computer Integrated Orthopedic Surgery— Connection of Planning and Execution in Surgical Inventions." In Taylor, R., Lavallee, S., Burdea G. Mosges, R. (eds). Computer Integrated Surgery. Cambridge, MIT press 451-463, 1996.
Radermacher et al., "Technique for Better Execution of CT Scan Planned Orthopedic Surgery on Bone Structures." In Lemke HW, Inamura, K., Jaffe, CC, Vannier, MW (eds). Computer Assisted Radiology, Berlin, Springer 933-938, 1995.
Radermacher et al., "CT Image Based Planning and Execution of Interventions in Orthopedic Surgery Using Individual Templates— Experimental Results and Aspects of Clinical Applications." In Nolte LP, Ganz, R. (eds). CAOS—Computer Assisted Orthopaedic Surgery. Bern, Hans Huber (In Press) 1998.
Radin et al., "Mechanical Determination of Osteoarthrosis," Sem Arthr Rheum 21(3): 12-21 (1991).
Radin et al., Characteristics of Joint Loading as it Applies to Osteoarthrosis in: Mow VC, Woo S.Y., Ratcliffe T., eds. Symposium on Biomechanics of Diathrodial Joints, vol. 2, New York, NY: Springer-Verlag, pp. 437-451 (1990).
Ranawat et al., "MacIntosh Hemiarthroplasty in Rheumatoid Knee," Acta Orthop Belg., 39 (1): 1-11 (1973).
Recht et al., "Accuracy of fat-suppressed three-dimensional spoiled gradient-echo FLASH MR imaging in the detection of patellofemoral articular cartilage abnormalities," Radiology 198: 209-212 (1996).
Recht et al., "MR imaging of articular cartilage: current status and future directions," AJR 163: 283-290 (1994).
Reiser et al., "Magnetic Resonance in Cartilaginous Lesions of the Knee Joint With Three-Dimensional Gradient-Echo Imaging," Skeletal Radiol. 17(7): 465-471, (1988).
Ritter et al., "Postoperative alignment of total knee replacement," Clin Orthop 299: 153-156 (1994).

(56) References Cited

OTHER PUBLICATIONS

Robarts Research Institute, Abstract #1028 (1999).
Robson et al., "A Combined Analysis and Magnetic Resonance Imaging Technique for Computerized Automatic Measurement of Cartilage Thickness in Distal Interphalangeal Joint," Magnetic Resonance Imaging 13(5): 709-718 (1995).
Rushfeldt et al., "Improved Techniques for Measuring In Vitro the Geometry and Pressure Distribution in the Human Acetabulum—1. Ultrasonic Measurement of Acetabular Surfaces, Sphericity and Cartilage Thickness," J. Biomech; 14(4): 253-260 (1981).
Saied, "Assessment of Articular Cartilage and Subchondral Bone: Subtle and Progressive Changes in Experimental Osteoarthritis Using 50 MHz Echography In Vitro", J. Bone Miner Res. 1997; 12(9): 1378-1386.
Saito et al., "New algorithms for Euclidean distance transformation of an-dimensional digitized picture with applications," Pattern Recognition 27(11): 1551-1565 (1994).
Schiffers et al., In German: "Planning and execution of orthopedic surgery using individualized templates," Der Orthopäde, Springer-Verlag, vol. 29, No. 7, pp. 636-640, (Jul. 2000).
Schiffers et al., English Translation with Certification: "Planning and execution of orthopedic surgery using individualized templates," Der Orthopäde, Springer-Verlag, vol. 29, No. 7, pp. 636-640, (Jul. 2000).
Schipplein et al., "Interaction between active and passive knee stabilizers during level walking," J Orthop Res 9: 113-119 (1991).
Schorn et al., "MacIntosh Arthroplasty in Rheumatoid Arthritis," Rheumatol Rehabil. Aug. 1978:17(3):155-163.
Schouten et al., "A 12 year follow up study in the general population on prognostic factors of cartilage loss in osteoarthritis of the knee," Ann Rheum Dis 51: 932-937 (1992).
Shapiro et al., "In-Vivo Evaluation of Human Cartilage Compression and Recovery using 1H and 23Na MRI," Proc. Intl. Soc. Mag. Resonance Med., 7:548 (1999).
Sharif et al., "Serum hyaluronic acid level as a predictor of disease progression in osteoarthritis of the knee," Arthritis Rheum 38: 760-767 (1995).
Sharma et al., "Knee adduction moment, serum hyaluronic acid level, and disease severity in medial tibiofemoral osteoarthritis," Arthritis and Rheumatism 41(7): 1233-40 (1998).
Shoup et al., "The driven equilibrium Fourier transform NMR technique: an experimental study," J Mag Res p. 298-310 (1972).
Sittek et al., "Assessment of Normal Patellar Cartilage Volume and Thickness Using MRI: an Analysis of Currently Available Pulse Sequences", Skeletal Radiol 1996; 25: 55-61.
Slemenda et al., "Lower extremity lean tissue mass strength predict increases in pain and in functional impairment in knee osteoarthritis," Arthritis Rheum 39(suppl): S212 (1996).
Slemenda et al., "Lower extremity strength, lean tissue mass and bone density in progression of knee osteoarthritis," Arthritis Rheum 39(suppl): S169 (1996).
Slone et al., "Body CT: A Practical Approach", Editor Slone, 1999 McGraw-Hill publishers, Title page and Table of Contents pgs. Only (ISBN 007058219).
Solloway et al., "The use of active shape models for making thickness measurements of articular cartilage from MR images," Mag Res Med 37: 943-952 (1997).
Soslowsky et al., "Articular Geometry of the Glenohumeral Joint," Clin. Orthop.; 285: 181-190 (Dec. 1992).
Spoor et al., "Rigid body motion calculated from spatial coordinates of markers," J. Biomechanics 13: 391-393 (1980).
Stammberger et al., "A Method for Quantifying Time Dependent Changes in MR Signal Intensity of Articular Cartilage as a Function of Tissue Deformation in Intact Joints" Medical Engineering & Physics 20: 741-749 (1998).
Stammberger et al., "A New Method for 3D Cartilage Thickness Measurement with MRI, Based on Euclidean Distance Transformation, and its Reproducibility in the Living," Proc. Intl. Soc. Mag. Resonance Med., 6:562 (1998).
Stammberger et al., "Elastic Registration of 3D Cartilage Surfaces From MR Image Data for Detecting Local Changes of the Cartilage Thickness," Magnetic Resonance in Medicine 44: 592-601 (2000).
Stammberger et al., "Determination of 3D cartilage thickness data from MR imaging: computational method and reproducibility in the living," Mag Res Med 41: 529-536 (1999).
Stammberger et al., "Interobserver to reproducibility of quantitative cartilage measurements: Comparison of B-spline snakes and manual segmentation," Mag Res Imaging 17: 1033-1042 (1999).
Stauffer et al., "The MacIntosh Prosthesis. Prospective Clinical and Gait Evaluation," Arch. Surg. 110(6):717-720 (1975).
Steines et al., Segmentation of osteoarthritic femoral cartilage using live wire, Proc. Intl. Soc. Mag. Resonance Med., 8:220 (2000).
Steines et al., "Segmentation of osteoarthritis femoral cartilage from MR images," CARS—Computer-Assisted Radiology and Surgery, pp. 578-583, San Francisco (2000).
Steines et al., "Measuring volume of articular cartilage defects in osteoarthritis using MRI," ACR 64th Annual Scientific Meeting, Philadelphia, (Oct. 2000).
Stevenson et al., "The fate of articular cartilage after transplantation of fresh and cryopreserved tissue-antigen-matched and mismatched osteochondral allografts in dogs," J. Bone Joint Surg 71(9): 1297-1307 (1989).
Stout et al., "X-Ray Structure Determination: A Practical Guide", $2^{nd}$ Ed. Editors Stout and Jensen, 1989, John Wiley & Sons, Title page and Table of Contents pgs. Only (ISBN 0471607118).
Taha et al., "Modeling and Design of a Custom Made Cranium Implant for Large Skull Reconstruction Before a Tumor Removal", Phidias Newsletter No. 6, pp. 3, 6, Jun. 2001. Retrieved from the Internet: URL:http://www.materialise.com/medical/files/pdf.
Tamez-Pena et al., MRI Isotropic Resolution Reconstruction from two Orthogonal Scans:, Proceedings of the SPIE—The International Society for Optical Engineering SOIE-OMT. vol. 4322, pp. 87-97, 2001.
Tebben et al., "Three-Dimensional Computerized Reconstruction. Illustration of Incremental Articular Cartilage Thinning," Invest. Radiol. 32(8): 475-484 (1997).
Thoma et al., In German: "Use of a New Subtraction Procedure Based on Three-Dimensional CT Scans for the Individual Treatment of Bone Defects in the Hip and Knee," Journal DGPW, No. 17, pp. 27-28 (May 1999).
Thoma et al., English Translation with Certification: "Use of a New Subtraction Procedure Based on Three-Dimensional CT Scans for the Individual Treatment of Bone Defects in the Hip and Knee," Journal DGPW, No. 17, pp. 27-28 (May 1999).
Thoma et al., In German: "Custom-made knee endoprosthetics using subtraction data of three-dimensional CT scans—A new approach," Der Orthopäde, Springer-Verlag, vol. 29, No. 7, pp. 641-644, (Jul. 2000).
Thoma et al., English Translation with Certification: "Custom-made knee endoprosthetics using subtraction data of three-dimensional CT scans—A new approach," Der Orthopäde, Springer-Verlag, vol. 29, No. 7, pp. 641-644, (Jul. 2000).
Tieschky et al., "Repeatability of patellar cartilage thickness patterns in the living, using a fat-suppressed magnetic resonance imaging sequence with short acquisition time and three-dimensional data processing," J. Orthop Res 15(6): 808-813 (1997).
Tomasi et al., "Shape and motion from image streams under orthography—a factorization method," Proc. Nat. Acad. Sci. 90(21): 9795-9802 (1993).
Tsai et al., "Application of a flexible loop-gap resonator for MR imaging of articular cartilage at 3.TO," International Society for Magnetic Resonance in Medicine, Denver (Apr. 24-28, 2000) 8:2127.
Tyler et al., "Detection and Monitoring of Progressive Degeneration of Osteoarthritic Cartilage by MRI," Acta Orthop Scand 1995; 66 Suppl. 266: 130-138 (1995).
Van Leersum et al., "Thickness of Patellofemoral Articular Cartilage as Measured on MR Imaging: Sequence Comparison of accuracy, reproducibility, and interobserver variation," Skeletal Radiol 1995; 24: 431-435 (1995).

(56) References Cited

OTHER PUBLICATIONS

Vandeberg et al., "Assessment of Knee Cartilage in Cadavers with Dual-Detector Sprial CT ARthrography and MR Imaging", Radiology, Feb. 2002: 222(2): 430-435 T. 195, V.V.
Van der Linden et al., "MR Imaging of Hyaline Cartilage at 0.5 T: A Quantitative and Qualitative in vitro Evaluation of Three Types of Sequences" pp. 297-305 (Jun. 1998).
Velyvis et al. "Evaluation of Articular Cartilage with Delayed Gd(DTPA)2-Enhanced MRI: Promise and Pitfalls," Proc. Intl. Soc. Mag. Resonance Med., 7:554 (1999).
Wang et al., "The influence of walking mechanics and time on the results of proximal tibial osteotomy," J. Bone Joint Surg 72A: 905-909 (1990).
Warfield et al., "Automatic Segmentation of MRI of the Knee," ISMRM Sixth Scientific Meeting and Exhibition p. 563, Sydney, Australia (Apr. 17-24, 1998).
Warfield et al., "Adaptive Template Moderated Spatially Varying Statistical Classification," Proc. First International Conference on Medical Image Computing and Computer Assisted, MICCAI, pp. 231-238 (1998).
Warfield et al., "Adaptive, Template Moderated Spatially Varying Statistical Classification," Medical Image Analysis 4(1): 43-55 (2000).
Waterton et al., "Diurnal variation in the femoral articular cartilage of the knee in young adult humans," Mag Res Med 43: 126-132 (2000).
Waterton et al., "Magnetic Resonance Methods for Measurement of Disease Progression in Rheumatoid Arthritis," Mag. Res. Imaging; 11: 1033-1038 (1993).
Watson et al., "MR Protocols for Imaging the Guinea Pig Knee," Mag. Res. Imaging 15(8): 957-970 (1997).
Wayne et al., "Measurement of Articular Cartilage Thickness in the Articulated Knee," ANN Biomed Eng.; 26(1): 96-102 (1998).
Wayne et al., "Finite Element Analyses of Repaired Articular Surfaces," Proc. Instn. Mech. Eng.; 205(3): 155-162 (1991).
Wiese et al., "Biomaterial properties and biocompatibility in cell culture of a novel self-inflating hydrogel tissue expander", J. Biomedical Materials Research Part A, 54(2):179-188, Nov. 2000.
Wolff et al., "Magnetization transfer contrast: MR imaging of the knee," Radiology 179: 623-628 (1991).
Wordsworth et al., "MacIntosh Arthroplasty for the Rheumatoid Knee: A 10-year Follow Up," Ann. Rheum. Dis. 44(11):738-741 (1985).
Worring et al., "Digital curvature estimation. CVGIP," Image Understanding 58(3): 366-382 (1993).
Yan, "Measuring changes in local volumetric bone density," new approaches to quantitative computed tomography, Ph.D. thesis, Dept. of Electrical Engineering, Stanford University (1998).
Yao et al., "Incidental magnetization transfer contrast in fast spin-echo imaging of cartilage," J. Magn Reson Imaging 6(1): 180-184 (1996).
Yao et al., "MR imaging of joints: analytic optimization of GRE techniques at 1.5T," AJR 158(2): 339-345 (1992).
Yasuda et al., "A 10 to 15 year follow up observation of high tibial osteotomy in medial compartment osteoarthritis," Clin Orthop 282: 186-195 (1992).
Yusof et al., "Preparation and characterization of chitin beads as a wound dressing precursor", J. Biomedical Materials Research Part A, 54(1):59-68, Oct. 2000.
Zimmer, Inc., "There's a New Addition to the Flex Family! The Zimmer® Unicompartmental Knee System", pp. 1-8 (2004).
International Searching Authority, International Search Report—International Application No. PCT/US02/16945, dated Mar. 26, 2003, 6 pages.
European Patent Office, Supplementary European Search Report—Application No. 03713907.8, dated Dec. 6, 2006, 3 pages.
European Patent Office, Supplementary Partial European Search Report—Application No. 02737254.9, dated Mar. 2, 2007, 5 pages.
International Searching Authority, International Search Report—International Application No. PCT/US03/38158, dated Feb. 23, 2005, 7 pages.
European Patent Office, European Search Report—Application No. EP 03790194, dated Jul. 13, 2006, 7 pages.
International Searching Authority, International Search Report—International Application No. PCT/US03/32123, dated Mar. 17, 2004, 7 pages.
International Searching Authority, International Search Report—International Application No. PCT/US03/36079, dated Apr. 15, 2004, 7 pages.
International Searching Authority, International Search Report—International Application No. PCT/US04/39714, dated May 13, 2005, together with the Written Opinion of the International Searching Authority, 8 pages.
International Searching Authority, International Search Report—International Application No. PCT/US2005/042421, dated May 18, 2006, together with the Written Opinion of the International Searching Authority, 7 pages.
European Patent Office, Supplementary European Search Report—Application No. 04812273.3, dated Oct. 8, 2007, 5 pages.
International Searching Authority, Invitation to Pay Additional Fees—International Application No. PCT/US2007/064349 dated Aug. 7, 2007, 8 pages.
International Searching Authority, International Search Report—International Application No. PCT/US2007/064349, dated Oct. 12, 2007, together with the Written Opinion of the International Searching Authority, 20 pages.
European Patent Office, Supplementary European Search Report—Application No. 04812273.3-2310, dated Dec. 10, 2007, 7 pages.
International Searching Authority, International Search Report—International Application No. PCT/US06/45131, dated Jul. 11, 2007, together with the Written Opinion of the International Searching Authority, 6 pages.
International Searching Authority, International Search Report—International Application No. PCT/US06/38212, dated Apr. 22, 2008, together with the Written Opinion of the International Searching Authority, 7 pages.
International Searching Authority, International Preliminary Report on Patentability—International Application No. PCT/US2006/045131, dated Jun. 5, 2008, together with the Written Opinion of the International Searching Authority, 6 pages.
International Searching Authority, International Search Report—International Application No. PCT/US2009/043656, dated Jul. 9, 2009, together with the Written Opinion of the International Searching Authority, 8 pages.
United States Patent and Trademark Office, Office Action dated Jul. 30, 2009, pertaining to U.S. Appl. No. 11/537,318, 56 pages.
Sunstein Kann Murphy & Timbers LLP, Request for Continued Examination and Response dated Aug. 27, 2009 pertaining to U.S. Appl. No. 10/752,438, 22 pages.
United States Patent and Trademark Office, Office Action dated Nov. 10, 2009 pertaining to U.S. Appl. No. 10/752,438, 8 pages.
Sunstein Kann Murphy & Timbers LLP, Request for Continued Examination and Response dated Jul. 27, 2009 pertaining to U.S. Appl. No. 10/997,407, 26 pages.
United States Patent and Trademark Office, Office Action dated Nov. 24, 2009 pertaining to U.S. Appl. No. 10/997,407, 14 pages.
United States Patent and Trademark Office, Office Action dated Jan. 9, 2009, pertaining to U.S. Appl. No. 10/764,010 (US Patent Publication No. US 2004/0167390), 11 pages.
Bromberg & Sunstein LLP, Response to Office Action dated Jan. 9, 2009, pertaining to U.S. Appl. No. 10/764,010 (US Patent Publication No. US 2004/0167390), 25 pages.
United States Patent and Trademark Office, Office Action dated Oct. 23, 2009, pertaining to U.S. Appl. No. 10/764,010 (US Patent Publication No. US 2004/0167390), 13 pages.
United States Patent and Trademark Office, Office Action dated Jul. 9, 2009, pertaining to U.S. Appl. No. 10/160,667, 5 pages.
Sunstein Kann Murphy & Timbers LLP, Amendment dated Jan. 11, 2010, pertaining to U.S. Appl. No. 10/160,667, 12 pages.
United States Patent and Trademark Office, Office Action dated Aug. 6, 2009, pertaining to U.S. Appl. No. 10/681,749, 6 pages.

(56) References Cited

OTHER PUBLICATIONS

Sunstein Kann Murphy & Timbers LLP, Response to Office Action dated Aug. 6, 2009, pertaining to U.S. Appl. No. 10/681,749, 18 pages.
United States Patent and Trademark Office, Office Action dated Nov. 25, 2008, pertaining to U.S. Appl. No. 10/681,750, 21 pages.
Sunstein Kann Murphy & Timbers LLP, Response to Office Action dated Nov. 25, 2008, pertaining to U.S. Appl. No. 10/681,750, 17 pages.
United States Patent and Trademark Office, Office Action dated Sep. 22, 2009, pertaining to U.S. Appl. No. 10/681,750, 21 pages.
European Patent Office, European Search Report—International Application No. PCT/US2006/045131 dated Mar. 3, 2010, 6 pages.
United States Patent and Trademark Office, Office Action dated Apr. 24, 2009, pertaining to U.S. Appl. No. 10/704,208, 23 pages.
Sunstein Kann Murphy & Timbers LLP, Request for Continued Examination and Response dated Oct. 26, 2009, pertaining to U.S. Appl. No. 10/704,208, 17 pages.
United States Patent and Trademark Office, Office Action dated Dec. 30, 2009, pertaining to U.S. Appl. No. 10/704,208, 10 pages.
International Searching Authority, International Search Report—International Application No. PCT/US2010/025459, dated Apr. 20, 2010, together with the Written Opinion of the International Searching Authority, 15 pages.
Bromberg & Sunstein LLP, Request for Continued Examination dated May 24, 2007, pertaining to U.S. Appl. No. 10/305,652, 21 pages.
United States Patent and Trademark Office, Office Action dated Aug. 13, 2007, pertaining to U.S. Appl. No. 10/305,652, 6 pages.
Bromberg & Sunstein LLP, Response to Office Action dated Aug. 13, 2007, pertaining to U.S. Appl. No. 10/305,652, 10 pages.
United States Patent and Trademark Office, Office Action dated Dec. 19, 2007, pertaining to U.S. Appl. No. 10/305,652, 6 pages.
Bromberg & Sunstein LLP, Response to Office Action dated Dec. 19, 2007, pertaining to U.S. Appl. No. 10/305,652, 17 pages.
Bromberg & Sunstein LLP, Supplemental Response dated May 2, 2008, pertaining to U.S. Appl. No. 10/305,652, 12 pages.
United States Patent and Trademark Office, Office Action dated Jul. 29, 2008, pertaining to U.S. Appl. No. 10/305,652, 10 pages.
Bromberg & Sunstein LLP, Amendment After Final Rejection dated Aug. 26, 2008, pertaining to U.S. Appl. No. 10/305,652, 17 pages.
United States Patent and Trademark Office, Office Action dated Aug. 4, 2009, pertaining to U.S. Appl. No. 10/704,325, 11 pages.
Sunstein Kann Murphy & Timbers LLP, Response to Office Action dated Aug. 4, 2009, pertaining to U.S. Appl. No. 10/704,325, 15 pages.
United States Patent and Trademark Office, Notice of Allowance dated May 17, 2010, pertaining to U.S. Appl. No. 10/704,325, 20 pages.
United States Patent and Trademark Office, Office Action dated Jul. 23, 2010, pertaining to U.S. Appl. No. 12/317,416, 7 pages.
United States Patent and Trademark Office, Office Action dated Apr. 26, 2010, pertaining to U.S. Appl. No. 10/160,667, 11 pages.
United States Patent and Trademark Office, Office Action dated Aug. 2, 2010, pertaining to U.S. Appl. No. 12/317,472, 7 pages.
United States Patent and Trademark Office, Office Action dated Aug. 5, 2010, pertaining to U.S. Appl. No. 10/997,407, 12 pages.
United States Patent and Trademark Office, Office Action dated May 26, 2010, pertaining to U.S. Appl. No. 11/602,713, 10 pages.
United States Patent and Trademark Office, Office Action dated Jun. 28, 2010, pertaining to U.S. Appl. No. 10/752,438, 9 pages.
United States Patent and Trademark Office, Office Action dated Mar. 4, 2010, pertaining to U.S. Appl. No. 11/688,340, 15 pages.
Sunstein Kann Murphy & Timbers LLP, Response to Office Action dated Jul. 30, 2009, pertaining to U.S. Appl. No. 11/537,318, 9 pages.
United States Patent and Trademark Office, Office Action dated Jun. 3, 2010, pertaining to U.S. Appl. No. 11/537,318, 10 pages.
International Searching Authority, International Search Report—International Application No. PCT/US2010/039587, dated Aug. 19, 2010, together with the Written Opinion of the International Searching Authority, 15 pages.
European Patent Office, Extended European Search Report—European Application No. 06815884.9-2310, dated Sep. 14, 2010, 7 pages.
United States Patent and Trademark Office, Office Action dated Sep. 15, 2010, pertaining to U.S. Appl. No. 10/704,208, 13 pages.
International Searching Authority, International Search Report—International Application No. PCT/US2010/025274, dated Sep. 20, 2010, together with the Written Opinion of the International Searching Authority, 18 pages.
Sunstein Kann Murphy & Timbers LLP, Preliminary Amendment dated Jul. 31, 2009, pertaining to U.S. Appl. No. 11/739,326, 19 pages.
United States Patent and Trademark Office, Office Action dated Apr. 20, 2010, pertaining to U.S. Appl. No. 11/739,326, 13 pages.
Sunstein Kann Murphy & Timbers LLP, Response to Office Action dated Apr. 20, 2010, pertaining to U.S. Appl. No. 11/739,326, 22 pages.
United States Patent and Trademark Office, Notice of Allowance dated Nov. 24, 2010, pertaining to U.S. Appl. No. 11/739,326, 8 pages.
United States Patent and Trademark Office, Office Action dated May 17, 2010, pertaining to U.S. Appl. No. 10/764,010, 12 pages.
Sunstein Kann Murphy & Timbers LLP, Response to Office Action dated May 17, 2010, pertaining to U.S. Appl. No. 10/764,010, 21 pages.
United States Patent and Trademark Office, Notice of Allowance dated Dec. 16, 2010, pertaining to U.S. Appl. No. 10/764,010, 11 pages.
Sunstein Kann Murphy & Timbers LLP, Response to Office Action dated Aug. 2, 2010, pertaining to U.S. Appl. No. 12/317,472, 15 pages.
United States Patent and Trademark Office, Office Action dated Feb. 10, 2011, pertaining to U.S. Appl. No. 12/317,416, 10 pages.
International Searching Authority, International Search Report—International Application No. PCT/US2010/046868, dated Jan. 7, 2011, together with the Written Opinion of the International Searching Authority, 11 pages.
United States Patent and Trademark Office, Office Action dated Feb. 22, 2011, pertaining to U.S. Appl. No. 11/602,713, 10 pages.
United States Patent and Trademark Office, Office Action dated Feb. 24, 2011, pertaining to U.S. Appl. No. 12/317,472, 12 pages.
United States Patent and Trademark Office, Office Action dated Mar. 2, 2011, pertaining to U.S. Appl. No. 10/752,438, 8 pages.
European Patent Office, Extended European Search Report—European Application No. 10012404.9-2310, dated Apr. 1, 2011, 7 pages.
United States Patent and Trademark Office, Office Action dated Apr. 18, 2011, pertaining to U.S. Appl. No. 12/464,763, 13 pages.
United States Patent and Trademark Office, Notice of Allowance dated Aug. 5, 2011, pertaining to U.S. Appl. No. 10/764,010, 14 pages.
United States Patent and Trademark Office, Office Action dated Sep. 15, 2011, pertaining to U.S. Appl. No. 10/997,407, 13 pages.
United States Patent and Trademark Office, Office Action dated Dec. 6, 2010, pertaining to U.S. Appl. No. 12/853,599, 11 pages.
Sunstein Kann Murphy & Timbers LLP, Response to Office Action dated Dec. 6, 2010, pertaining to U.S. Appl. No. 12/853,599, 16 pages.
United States Patent and Trademark Office, Notice of Allowance dated Sep. 14, 2011, pertaining to U.S. Appl. No. 12/853,599, 9 pages.
International Searching Authority, International Search Report—International Application No. PCT/US2010/055483, dated Jul. 28, 2011, together with the Written Opinion of the International Searching Authority, 9 pages.
Bromberg & Sunstein LLP, Preliminary Amendment dated Aug. 22, 2006, pertaining to U.S. Appl. No. 11/410,515, 10 pages.
United States Patent and Trademark Office, Office Action dated Dec. 30, 2008, pertaining to U.S. Appl. No. 11/410,515, 32 pages.

(56) References Cited

OTHER PUBLICATIONS

Bromberg & Sunstein LLP, Amendment dated Jun. 30, 2009, pertaining to U.S. Appl. No. 11/410,515, 18 pages.
Sunstein Kann Murphy & Timbers LLP, Supplemental Amendment dated Aug. 26, 2009, pertaining to U.S. Appl. No. 11/410,515, 11 pages.
Sunstein Kann Murphy & Timbers LLP, Supplemental Amendment dated Sep. 21, 2009, pertaining to U.S. Appl. No. 11/410,515, 11 pages.
United States Patent and Trademark Office, Office Action dated Dec. 28, 2009, pertaining to U.S. Appl. No. 11/410,515, 43 pages.
Sunstein Kann Murphy & Timbers LLP, Amendment dated Jun. 28, 2010 pertaining to U.S. Appl. No. 11/410,515, 16 pages.
United States Patent and Trademark Office, Office Action dated Oct. 6, 2010 pertaining to U.S. Appl. No. 11/410,515, 20 pages.
Sunstein Kann Murphy & Timbers LLP, Amendment dated Apr. 6, 2011 pertaining to U.S. Appl. No. 11/410,515, 12 pages.
Sunstein Kann Murphy & Timbers LLP, Preliminary Amendment dated Jul. 31, 2009 pertaining to U.S. Appl. No. 11/769,434, 44 pages.
United States Patent and Trademark Office, Office Action dated Aug. 2, 2010 pertaining to U.S. Appl. No. 11/769,434, 83 pages.
Sunstein Kann Murphy & Timbers LLP, Amendment dated Feb. 2, 2011 pertaining to U.S. Appl. No. 11/769,434, 44 pages.
Sunstein Kann Murphy & Timbers LLP, Preliminary Amendment dated Aug. 12, 2011, pertaining to U.S. Appl. No. 13/017,886, 13 pages.
United States Patent and Trademark Office, Office Action dated Jun. 23, 2011 pertaining to U.S. Appl. No. 11/410,515, 13 pages.
International Searching Authority, International Search Report—International Application No. PCT/US2010/059910 dated Oct. 25, 2011, together with the Written Opinion of the International Searching Authority, 9 pages.
International Searching Authority, International Search Report—International Application No. PCT/US2012/025269 dated Aug. 31, 2012, together with the Written Opinion of the International Searching Authority, 14 pages.
International Searching Authority, International Search Report—International Application No. PCT/US2012/050964 dated Oct. 22, 2012, together with the Written Opinion of the International Searching Authority, 13 pages.
European Patent Office, European Search Report—Application No. 12170854.9-1526 dated Oct. 9, 2012, 6 pages.
International Searching Authority, International Search Report—International Application No. PCT/US12/59936 dated Jan. 9, 2013, together with the Written Opinion of the International Searching Authority, 11 pages.
European Patent Office, Extended European Search Report—Application No. 10792589.3-2310 dated Feb. 7, 2013, 9 pages.
European Patent Office, European Search Report—Application No. 10192339.9-1257 dated Jan. 23, 2013, 5 pages.
European Patent Office, Extended European Search Report—Application No. 10746859.7-1654 dated Mar. 4, 2013, 7 pages.
International Searching Authority, International Search Report—International Application No. PCT/US2009/036165 dated May 7, 2009, together with the Written Opinion of the International Searching Authority, 9 pages.
International Searching Authority, Invitation to Pay Additional Fees—International Application No. PCT/US2010/025274, dated Jun. 28, 2010, 4 pages.
U.S. Appl. No. 10/752,438, filed Jan. 5, 2004.
U.S. Appl. No. 12/317,416, filed Dec. 22, 2008.
U.S. Appl. No. 12/317,472, filed Dec. 22, 2008.
U.S. Appl. No. 12/031,239, filed Feb. 14, 2008.
U.S. Appl. No. 12/712,072, filed Feb. 24, 2010.
U.S. Appl. No. 12/660,529, filed Feb. 25, 2010.
U.S. Appl. No. 13/044,413, filed Mar. 9, 2011.
U.S. Appl. No. 13/312,339, filed Dec. 6, 2011.
Cohen et al., "Computer-Aided Planning of Patellofemoral Joint OA Surgery: Developing Physical Models from Patient MRI", MICCAI, Oct. 11-13, 1998, 13 pages.
Harryson et al., "Custom-Designed Orthopedic Implants Evaluated Using Finite Element Analysis of Patient-Specific Computed Tomoraphy Data: Femoral-Component Case Study", BMC Musculoskeletal Disorders, vol. 8(91), Sep. 2007, 10 pages.
Lombardi, Jr. et al., "Patient-Specific Approach in Total Knee Arthroplasty", Orthopedics, vol. 31, Issue 9, Sep. 2008, 8 pages.
Overhoff et al., "Total Knee Arthroplasty: Coordinate System Definition and Planning Based on 3-D Ultrasound Image Volumes", CARS 2001, pp. 283-288.
Robinson et al., "The Early Innovators of Today's Resurfacing Condylar Knees", The Journal of Arthroplasty, vol. 20, No. 1, Suppl. 1, 2005.
Tsai et al., "Accurate Surface Voxelization for Manipulating Volumetric Surfaces and Solids with Application in Simulating Musculoskeletal Surgery", Inst. of Information and Computer Engineering, pp. 234-243, 2001.
European Patent Office, Extended European Search Report—Application No. 12192903.8-1654 dated Apr. 17, 2013, 8 pages.
European Patent Office, European Search Report—Application No. 10829105.5-1654 dated Nov. 5, 2013, 3 pages.
European Patent Office, Extended European Search Report—Application No. 10838327.4-1654 dated Nov. 14, 2013, 6 pages.
International Searching Authority, Great Britain Search and Examination Report—Application No. GB1201112.8 dated Feb. 3, 2014, 4 pages.
International Searching Authority, International Search Report—International Application No. PCT/US2012/025274, dated Oct. 25, 2012, together with the Written Opinion of the International Searching Authority, 12 pages.
International Searching Authority, International Search Report—International Application No. PCT/US2012/025277, dated Oct. 25, 2012, together with the Written Opinion of the International Searching Authority, 12 pages.
International Searching Authority, International Search Report—International Application No. PCT/US2012/025280 dated Oct. 25, 2012, together with the Written Opinion of the International Searching Authority, 11 pages.
International Searching Authority, International Search Report—International Application No. PCT/US2013/035536 dated Jul. 18, 2013, 3 pages.
International Searching Authority, International Search Report—International Application No. PCT/US2013/028762 dated Jun. 21, 2013, 9 pages.
International Searching Authority, International Search Report—International Application No. PCT/US2013/061042 dated Jan. 10, 2014, together with the Written Opinion of the International Searching Authority, 12 pages.
International Searching Authority, International Search Report—International Application No. PCT/US13/56841 dated Feb. 12, 2014, together with the Written Opinion of the International Searching Authority, 9 pages.
Intergraph Corp. and Surgicad Corp., "Surgicad Design Combines 3-D Visualization with CAD Tools", Intergraph Corp. and Surgicad Corp. News Brief, 2 pages, Sep. 1993.
Birnbaum et al., "Computer-Assisted Orthopedic Surgery With Individual Templates and Comparison to Conventional Operation Method", Spine, vol. 26, No. 4, pp. 365-369, Feb. 2001.
Buechel et al., "Meniscal-Bearing Total Knee Arthroplasty", Chapter 10 of Surgical Techniques in Total Knee Arthroplasty, pp. 81-89, 2002.
Delp et al., "Computer Assisted Knee Replacement", Clinical Orthopaedics, pp. 49-56, Sep. 1998.
Froemel et al., "Computer Assisted Template Based Navigation for Total Knee Replacement", Documents presented at CAOS on Jun. 17, 2001, 4 pages.
Mahaisavariya et al., "Morphological Study of the Proximal Femur: A New Method of Geometrical Assessment Using 3 Dimensional Reverse Engineering", Med. Eng. and Phys., vol. 24, pp. 617-622, 2002.

(56) References Cited

OTHER PUBLICATIONS

Müller-Wittig et al., "A Computer-Assisted Planning System for Total Knee Replacement", CG Topics, pp. 17-19, Jun. 2000.
Udupa et al., "3D Imaging in Medicine", Second Edition, pp. 84-86, 2000.
International Searching Authority, International Search Report—International Application No. PCT/US2010/061141, dated Aug. 31, 2011, together with the Written Opinion of the International Searching Authority, 8 pages.
International Searching Authority, International Search Report—International Application No. PCT/US14/27446, dated Aug. 11, 2014, together with the Written Opinion of the International Searching Authority, 14 pages.
International Searching Authority, International Search Report—International Application No. PCT/US2014/023235 dated Sep. 24, 2014, together with the Written Opinion of the International Searching Authority, 15 pages.
International Searching Authority, International Search Report—International Application No. PCT/US2014/030015 dated Aug. 27, 2014, together with the Written Opinion of the International Searching Authority, 9 pages.
International Searching Authority, International Search Report—International Application No. PCT/US2014/031487 dated Sep. 2, 2014, together with the Written Opinion of the International Searching Authority, 17 pages.
European Patent Office, Extended European Search Report—Application No. 10836760.8-1654 dated Apr. 11, 2014, 6 pages.
European Patent Office, European Search Report—European Application No. 12000991.5 dated May 23, 2014, 6 pages.
U.S. Appl. No. 10/704,208, filed Nov. 7, 2003.
U.S. Appl. No. 10/997,407, filed Nov. 24, 2004.
U.S. Appl. No. 12/398,598, filed Mar. 5, 2009.
U.S. Appl. No. 12/772,683, filed May 3, 2010.
U.S. Appl. No. 12/777,809, filed May 11, 2010.
U.S. Appl. No. 12/777,859, filed May 11, 2010.
U.S. Appl. No. 12/777,878, filed May 11, 2010.
U.S. Appl. No. 12/778,518, filed May 12, 2010.
U.S. Appl. No. 12/821,301, filed Jun. 23, 2010.
U.S. Appl. No. 13/157,857, filed Jun. 10, 2011.
U.S. Appl. No. 13/294,564, filed Nov. 11, 2011.
U.S. Appl. No. 13/294,573, filed Nov. 11, 2011.
U.S. Appl. No. 13/294,579, filed Nov. 11, 2011.
U.S. Appl. No. 13/294,617, filed Nov. 11, 2011.
U.S. Appl. No. 13/397,457, filed Feb. 15, 2012.
U.S. Appl. No. 13/399,378, filed Feb. 17, 2012.
U.S. Appl. No. 13/761,818, filed Feb. 7, 2013.
U.S. Appl. No. 14/134,064, filed Dec. 19, 2013.
U.S. Appl. No. 14/148,511, filed Jan. 6, 2014.
U.S. Appl. No. 14/157,707, filed Jan. 17, 2014.
European Patent Office, Extended European Search Report—Application No. 12820490.6-1654, dated Jun. 26, 2015, 6 pages.
European Patent Office, European Search Report pertaining to European Application No. 15189568.6-1654 dated Feb. 9, 2016, 7 pages.
Intellectual Property Office of Singapore, Search Report dated Jun. 9, 2015 pertaining to Singapore Application No. 10201400158U, 15 pages.
International Searching Authority, International Search Report—International Application No. PCT/US2012/049472 dated Oct. 16, 2012, together with the Written Opinion of the International Searching Authority, 12 pages.
International Searching Authority, International Search Report—International Application No. PCT/US2014/030001 dated Aug. 27, 2014, together with the Written Opinion of the International Searching Authority, 10 pages.
Sunstein Kann Murphy & Timbers LLP, Response to Office Action dated Sep. 6, 2007, pertaining to U.S. Appl. No. 10/764,010, 22 pages.
United States Patent and Trademark Office Office, Action dated Apr. 10, 2008, pertaining to U.S. Appl. No. 10/764,010, 17 pages.
Intellectual Property Office of Singapore, Search Report and Written Opinion dated Jun. 10, 2015, pertaining to Singapore Application No. 11201405753X, 33 pages.
Intellectual Property Office of Singapore, Written Opinion pertaining to Singapore Patent Application No. 11201405753X, dated Jan. 20, 2016, 12 pages.
U.S. Appl. No. 10/160,667, filed May 28, 2002.
U.S. Appl. No. 10/305,652, filed Nov. 27, 2002, now U.S. Pat. No. 7,468,074.
U.S. Appl. No. 10/681,749, filed Oct. 7, 2003, now U.S. Pat. No. 7,799,077.
U.S. Appl. No. 10/681,750, filed Oct. 7, 2003.
U.S. Appl. No. 10/704,208, filed Nov. 7, 2003, now U.S. Pat. No. 8,932,363.
U.S. Appl. No. 10/704,325, filed Nov. 7, 2003, now U.S. Pat. No. 7,796,791.
U.S. Appl. No. 10/752,438, filed Jan. 5, 2004, now U.S. Pat. No. 8,545,569.
U.S. Appl. No. 10/997,407, filed Nov. 24, 2004, now U.S. Pat. No. 8,882,847.
U.S. Appl. No. 12/317,416, filed Dec. 22, 2008, now U.S. Pat. No. 8,343,218.
U.S. Appl. No. 12/317,472, filed Dec. 22, 2008, now U.S. Pat. No. 8,337,507.
U.S. Appl. No. 11/688,340, filed Mar. 20, 2007.
U.S. Appl. No. 11/602,713, filed Nov. 21, 2006.
U.S. Appl. No. 12/031,239, filed Feb. 14, 2008, now U.S. Pat. No. 8,617,242.
U.S. Appl. No. 12/398,598, filed Mar. 5, 2009, now U.S. Pat. No. 8,682,052.
U.S. Appl. No. 12/398,871, filed Mar. 5, 2009.
U.S. Appl. No. 12/398,880, filed Mar. 5, 2009.
U.S. Appl. No. 12/464,763, filed May 12, 2009.
U.S. Appl. No. 12/712,072, filed Feb. 24, 2010, now U.S. Pat. No. 8,234,097.
U.S. Appl. No. 12/772,683, filed May 3, 2010, now U.S. Pat. No. 8,709,089.
U.S. Appl. No. 12/777,859, filed May 11, 2010, now U.S. Pat. No. 8,768,028.
U.S. Appl. No. 12/777,878, filed May 11, 2010, now U.S. Pat. No. 8,690,945.
U.S. Appl. No. 12/778,506, filed May 12, 2010.
U.S. Appl. No. 12/778,518, filed May 12, 2010, now U.S. Pat. No. 8,945,230.
U.S. Appl. No. 12/660,529, filed Feb. 25, 2010, now U.S. Pat. No. 8,480,754.
U.S. Appl. No. 12/799,299, filed Apr. 21, 2010.
U.S. Appl. No. 12/799,355, filed Apr. 22, 2010.
U.S. Appl. No. 12/799,641, filed Apr. 28, 2010.
U.S. Appl. No. 12/821,301, filed Jun. 23, 2010, now U.S. Pat. No. 8,771,365.
U.S. Appl. No. 12/853,599, filed Aug. 10, 2010, now U.S. Pat. No. 8,077,950.
U.S. Appl. No. 12/965,493, filed Dec. 10, 2010.
U.S. Appl. No. 13/044,413, filed Mar. 9, 2011, now U.S. Pat. No. 8,556,983.
U.S. Appl. No. 13/157,857, filed Jun. 10, 2011, now U.S. Pat. No. 8,735,773.
U.S. Appl. No. 13/312,339, filed Dec. 6, 2011, now U.S. Pat. No. 8,634,617.
U.S. Appl. No. 13/294,564, filed Nov. 11, 2011, now U.S. Pat. No. 8,906,107.
U.S. Appl. No. 13/294,573, filed Nov. 11, 2011, now U.S. Pat. No. 8,974,539.
U.S. Appl. No. 13/294,579, filed Nov. 11, 2011, now U.S. Pat. No. 8,926,706.
U.S. Appl. No. 13/294,623, filed Nov. 11, 2011.
U.S. Appl. No. 13/397,457, filed Feb. 15, 2012, now U.S. Pat. No. 9,020,788.
U.S. Appl. No. 13/565,840, filed Aug. 3, 2012.
U.S. Appl. No. 14/238,989, filed Aug. 15, 2012.
U.S. Appl. No. 13/718,717, filed Dec. 18, 2012.
U.S. Appl. No. 13/718,735, filed Dec. 18, 2012.

(56) References Cited

OTHER PUBLICATIONS

U.S. Appl. No. 13/746,742, filed Jan. 22, 2013.
U.S. Appl. No. 14/380,212, filed Mar. 2, 2013.
U.S. Appl. No. 14/389,987, filed Apr. 6, 2013.
U.S. Appl. No. 13/835,863, filed Mar. 15, 2013.
U.S. Appl. No. 13/886,040, filed May 2, 2013.
U.S. Appl. No. 13/887,712, filed May 6, 2013.
U.S. Appl. No. 14/017,176, filed Sep. 3, 2013.
U.S. Appl. No. 14/040,890, filed Sep. 30, 2013.
U.S. Appl. No. 14/051,003, filed Oct. 10, 2013.
U.S. Appl. No. 14/157,707, filed Jan. 17, 2014, now U.S. Pat. No. 8,965,088.
U.S. Appl. No. 14/169,093, filed Jan. 30, 2014.
U.S. Appl. No. 14/168,947, filed Jan. 30, 2014.
U.S. Appl. No. 14/236,782, filed Feb. 3, 2014.
U.S. Appl. No. 14/774,970, filed Mar. 11, 2014.
U.S. Appl. No. 14/775,155, filed Mar. 14, 2014.
U.S. Appl. No. 14/775,190, filed Mar. 15, 2014.
U.S. Appl. No. 14/222,836, filed Mar. 24, 2014, now U.S. Pat. No. 9,180,015.
U.S. Appl. No. 14/222,253, filed Mar. 21, 2014.
U.S. Appl. No. 14/246,335, filed Apr. 7, 2014, now U.S. Pat. No. 9,186,254.
U.S. Appl. No. 14/285,151, filed May 22, 2014.
U.S. Appl. No. 14/308,070, filed Jun. 18, 2014.
U.S. Appl. No. 14/315,714, filed Jun. 26, 2014.
U.S. Appl. No. 14/537,175, filed Nov. 10, 2014.
U.S. Appl. No. 14/594,492, filed Jan. 12, 2015.
U.S. Appl. No. 14/696,724, filed Apr. 27, 2015.
U.S. Appl. No. 14/935,965, filed Nov. 9, 2015.
U.S. Appl. No. 11/537,318, filed Sep. 29, 2006.
U.S. Appl. No. 13/013,265, filed Jan. 25, 2011.
U.S. Appl. No. 13/013,354, filed Jan. 25, 2011.
U.S. Appl. No. 13/013,383, filed Jan. 25, 2011.
U.S. Appl. No. 13/013,461, filed Jan. 25, 2011.
U.S. Appl. No. 13/013,470. filed Jan. 25, 2011, now U.S. Pat. No. 9,113,921.
U.S. Appl. No. 13/014,474, filed Jan. 26, 2011.
U.S. Appl. No. 13/561,696, filed Jul. 30, 2012.
U.S. Appl. No. 13/625,694, filed Sep. 24, 2012, now U.S. Pat. No. 8,551,169.
U.S. Appl. No. 13/938,081, filed Jul. 9, 2013.
U.S. Appl. No. 14/051,087, filed Oct. 10, 2013.

* cited by examiner

AUTOMATED SYSTEMS FOR MANUFACTURING PATIENT-SPECIFIC ORTHOPEDIC IMPLANTS AND INSTRUMENTATION

RELATED APPLICATIONS

This application is a continuation application of U.S. patent application Ser. No. 12/712,072, filed Feb. 24, 2010, which in turn claims priority to U.S. Provisional Application 61/208,440, filed Feb. 24, 2009, entitled "Automated Systems for Manufacturing Patient-Specific Orthopedic Implants and Instrumentation."

U.S. patent application Ser. No. 12/712,072 also claims priority to U.S. Provisional Application 61/208,444, filed Feb. 24, 2009, entitled "Automated Systems for Manufacturing Patient-Specific Orthopedic Implants and Instrumentation."

U.S. patent application Ser. No. 12/712,072 also is a continuation-in-part application of U.S. patent application Ser. No. 11/671,745, filed Feb. 6, 2007, entitled "Patient Selectable Joint Arthroplasty Devices and Surgical Tools", which in turn claims the benefit of U.S. Ser. No. 60/765,592 entitled "Surgical Tools for Performing Joint Arthroplasty" filed Feb. 6, 2006; U.S. Ser. No. 60/785,168, entitled "Surgical Tools for Performing Joint Arthroplasty" filed Mar. 23, 2006; and U.S. Ser. No. 60/788,339, entitled "Surgical Tools for Performing Joint Arthroplasty" filed Mar. 31, 2006.

U.S. Ser. No. 11/671,745 is also a continuation-in-part of U.S. Ser. No. 11/002,573 for "Surgical Tools Facilitating Increased Accuracy, Speed and Simplicity in Performing Joint Arthroplasty" filed Dec. 2, 2004 which is a continuation-in-part of U.S. Ser. No. 10/724,010 for "Patient Selectable Joint Arthroplasty Devices and Surgical Tools Facilitating Increased Accuracy, Speed and Simplicity in Performing Total and Partial Joint Arthroplasty" filed Nov. 25, 2003 which is a continuation-in-part of U.S. Ser. No. 10/305,652 entitled "Methods and Compositions for Articular Repair," filed Nov. 27, 2002, which is a continuation-in-part of U.S. Ser. No. 10/160,667, filed May 28, 2002, which in turn claims the benefit of U.S. Ser. No. 60/293,488 entitled "Methods To Improve Cartilage Repair Systems", filed May 25, 2001, U.S. Ser. No. 60/363,527, entitled "Novel Devices For Cartilage Repair, filed Mar. 12, 2002 and U.S. Ser. Nos. 60/380,695 and 60/380,692, entitled "Methods And Compositions for Cartilage Repair," and "Methods for Joint Repair," filed May 14, 2002.

U.S. Ser. No. 11/671,745 is also a continuation-in-part of U.S. Ser. No. 10/728,731, entitled "Fusion of Multiple Imaging Planes for Isotropic Imaging in MRI and Quantitative Image Analysis using Isotropic or Near-Isotropic Imaging," filed Dec. 4, 2003, which claims the benefit of U.S. Ser. No. 60/431,176, entitled "Fusion of Multiple Imaging Planes for Isotropic Imaging in MRI and Quantitative Image Analysis using Isotropic or Near Isotropic Imaging," filed Dec. 4, 2002.

U.S. Ser. No. 11/671,745 is also a continuation-in-part of U.S. Ser. No. 10/681,750, entitled "Minimally Invasive Joint Implant with 3-Dimensional Geometry Matching the Articular Surfaces," filed Oct. 7, 2003, which claims the benefit of U.S. Ser. No. 60/467,686, entitled "Joint Implants," filed May 2, 2003 and U.S. Ser. No. 60/416,601, entitled Minimally Invasive Joint Implant with 3-Dimensional Geometry Matching the Articular Surfaces," filed Oct. 7, 2002.

Each of the above-described applications is hereby incorporated by reference in their entireties.

This application relates to U.S. patent application Ser. No. 12/398,753, filed Mar. 5, 2009, entitled "Patient Selectable Joint Arthroplasty Devices and Surgical Tools," which in turn claims priority to U.S. Provisional Patent Application No. 61/034,048, filed Mar. 5, 2008, entitled "Patient Selectable Joint Arthroplasty Devices and Surgical Tools," and U.S. Provisional Patent Application No. 61/034,048, filed Mar. 5, 2008, entitled "Patient Selectable Joint Arthroplasty Devices and Surgical Tools," each of these above-described applications hereby incorporated by reference in their entireties.

BACKGROUND

Technical Field

The embodiments described herein relate to automated systems for designing and manufacturing patient-specific orthopedic devices, such as implants and instrumentation, based on data, such as imaging data, representing an existing joint.

Description of the Related Art

Personalized medicine is one of the fastest growing trends in the healthcare industry. While this trend has mainly been seen in the drug sector, medical device manufacturers have also recognized the benefits of individualizing their products to meet the needs of different patient groups. The orthopedic implant manufacturers have recently launched implants optimized for different genders or geographies, or combining patient-specific instruments with standardized implants. However, these are not truly personalized, patient-specific or patient-matched approaches. Technological advances now allow for the design and manufacture of implants and associated instrumentation optimized for a specific individual. Such implants fall on a spectrum from, e.g., implants that are based on one or two aspects or dimensions of a patient's anatomy (such as a width of a bone, a location of a defect, etc.) to implants that are designed to conform entirely to that patient's anatomy and/or to replicate the patient's kinematics.

One example of such patient-specific or patient-matched technology is the ConforMIS iFit® technology used in the iUni® (unicompartmental knee resurfacing implant) and iDuo® (dual compartmental knee resurfacing implant). This technology converts Computed Axial Tomography ("CT") or Magnetic Resonance Imaging ("MRI") scans into individualized, minimally invasive articular replacement systems capable of establishing normal articular shape and function in patients with osteoarthritis. By starting with imaging data, the approach results in implants that conform to bone or cartilage, and reduce the need for invasive tissue resection. The implant is made to fit the patient rather than the reverse. By designing devices that conform to portions of the patient's anatomy, the implants allow the surgeon to resurface rather than replace the joint, providing for far more tissue preservation, a reduction in surgical trauma, and a simplified technique.

The image-to-implant process begins with the patient having a medical image such as a CT or MRI scan, which can be done on commonly available machines, using a standardized protocol that ensures the data needed to design the implant is captured properly. The image data is then combined with computer-aided design (CAD) methods to generate a patient-specific model of the knee from which a patient-specific implant and/or patient-specific instrumentation can be designed and manufactured. The electronic design file created during this process is used to fabricate the patient-specific implant and custom instrumentation, which is a process that takes approximately four to six weeks.

The development and manufacture time associated with all types of patient specific devices could be significantly reduced if some or all aspects of the design and manufacture process were fully automated or more fully automated. Automation of some or all aspects of the process, including, without limitation, imaging, diagnosis, surgical planning, instrumentation design, implant design, manufacture, quality systems and distribution could result in, among other advantages, faster and less costly production, which could result in patient's being able to have surgery sooner and at a lower cost. Additionally, such systems could improve productivity of designers, which would have several advantages such as improving profitability of manufacturing such implants. Further, such systems would both directly and indirectly improve the quality of such implants by, example, providing defined rules to ensure patient-specific implant designs meet specification, and also indirectly by improving the cost effectiveness of skilled designers, which makes the technically skilled employees found in more developed countries such as the United States more economically competitive and thereby reducing the impetus to outsource such production to countries with less technically skilled but cheaper labor that may result in reduced quality in the design process.

SUMMARY

Some embodiments described herein include new computer-based methods used to generate the designs for personalized joint implants that are custom-tailored to a patient's individual anatomy. The anatomic information is derived from medical images, such as CT or MRI scans. Other types of images also could be used, including, without limitation, x-ray images. A variety of segmentation methods can be applied to extract the relevant anatomic information.

In one embodiment, the anatomic information resulting from the segmentation can be composed of individual points, surface information, or solid bodies, preferably in 3 or more dimensions. In another embodiment, the anatomic information results in a virtual model of the patient's anatomy.

The processing of the anatomic information and the generation of the custom-fit implant design can have different degrees of automation. It can be fully automated, thus not requiring any user input. It can provide default settings that may be modified and fine-tuned by the operator. In any automated step performed by the system, constraints pertaining to a specific implant model, to a group of patients or to the individual patient may be taken into account. For example, the maximum implant thickness or allowable positions of implant anchors may depend on the type of implant. The minimum implant thickness can depend on the patient's bone quality.

In another embodiment, the system supports the operator by guiding him/her through the design workflow and prompting the user for required input. For example, the system follows a predefined step-by-step design protocol. It performs automated calculations whenever possible. For certain steps that require operator intervention, the system presents the operator with all information necessary to provide his input. This can include, without limitation, showing the design status from a specific viewpoint that allow the operator to best make the required decision on the particular design step. Once the information has been entered by the operator, the system can continue the automated design protocol until further operator interaction becomes necessary.

In another embodiment, the system uses anatomic landmarks to generate an implant design. The system can, for example, merge the patient's anatomic information with a generic atlas or model containing the landmark information. By merging the two pieces of information, the landmark information is transferred into the patient information, thus allowing the system to use the landmark information as reference in the implant design. Alternatively, the landmark information may be derived directly from the patient's anatomical data, for example and without limitation, by locating curvature maxima or minima or other extrema.

In another embodiment, the system automatically finds the best viewpoint to allow the user to perform a design step. This can be facilitated by using the landmark information derived from the patient's anatomical information. For example, the system can find the best view to allow the operator to define the implant's outer profile or contour.

In another embodiment, the implant profile is defined using a virtual template. The template may be fitted automatically to the patient's anatomical model, for example, by using the generic atlas, which may have the virtual template integrated into it. The anatomical model can be represented by a series of 2D images or a 3D representations. The model typically, but not always, will have at least one of bone or cartilage already segmented.

Alternatively, the virtual template can be user-adjustable. The system can provide an initial default fit of the template and then allow the user to make adjustments or fine-tune the shape or position. The system can update the implant as the operator makes adjustments to the template, thus providing real-time feedback about the status of the implant design. The adjustments can be made, for example, for irregularities of the articular surface including osteophytes or subchondral cysts, or flattening of an articular surface.

The virtual template can be a 3D template. In another embodiment, the virtual template is a 2D template that is projected onto a 2D or 3D anatomical model of the patient's anatomy. The template can be a composite of standard geometric shapes, such as straight lines, arcs or other curved elements in 2D and planes, spherical shapes or other curved elements in 3D. Alternatively, the template may have an irregular, free-form shape. To adjust the shape of the template, the system or the operator can move the standard shapes or adjust the radius of the curved elements. In another embodiment, the virtual template may have a number of control points that can be used to adjust its shape. In yet another embodiment, the center line of the profile can be used to adjust its shape.

In another embodiment, the final implant includes one or more bone cuts. The cut planes for these bone cuts can be automatically determined by the system, for example using anatomical landmarks. The cut planes can also be built into a generic virtual atlas that is merged with the patient's anatomical information. Optionally, the cut planes can be adjusted by the operator.

The system can also construct the implant surfaces. Surfaces may be composed of different elements. In one embodiment, elements of the surfaces will conform to the patient's anatomy. In these situations the system can build a surface using the patient's anatomical model, for example by constructing a surface that is identical with or mostly parallel to the patient's anatomical surface. In another embodiment, the system uses geometric elements such as arcs or planes to construct a surface. Transitions between surfaces can be smoothed using tapers or fillets. Additionally, the system may take into account constraints such as minimum or maximum thickness or length or curvature of parts or aspects of the implant when constructing the surfaces.

In another embodiment, the system can automatically or semi-automatically add other features to the implant design. For example, the system can add pegs or anchors or other attachment mechanisms. The system can place the features using anatomical landmarks. Constraints can be used to restrict the placement of the features. Examples of constraints for placement of pegs are the distance between pegs and from the pegs to the edge of the implant, the height of the pegs that results from their position on the implant, and forcing the pegs to be located on the center line.

Optionally, the system can allow the user to fine-tune the peg placement, with or without enforcing the constraints.

In another embodiment, the additional features are embedded with the generic virtual atlas and merged with the patient-specific anatomical information, thus overlaying the information about the position of the feature embedded in the atlas on top of the patient's anatomical model.

In other embodiments, devices that are tailored to only one or a few dimensions or aspects of a patient's anatomy are designed using automated processes.

The principals can also be applied to other devices, such as the design and manufacture of patient-specific instruments, such as jigs used in orthopedic surgeries or other instrumentation. Similarly, the concepts can be applied to portions of the design of an implant or instrument, such as the design of an articular surface of a patient-specific and/or patient-engineered articular implant.

DETAILED DESCRIPTION

Various embodiments of the invention can be adapted and applied to implants and other devices associated with any anatomical joint including, without limitation, a spine, spinal articulations, an intervertebral disk, a facet joint, a shoulder joint, an elbow, a wrist, a hand, a finger joint, a hip, a knee, an ankle, a foot and toes. Furthermore, various embodiments can be adapted and applied to implants, instrumentation used during surgical or other procedures, and methods of using various patient-specific implants, instrumentation and other devices.

One embodiment is a nearly-fully automated system to design a patient-specific implant that requires minimal input from a designer or other operator and that is capable of designing an implant in a small fraction of the time it takes for a designer to design such an implant using computer aided design (CAD) tools.

Automated Design of a Patient-Specific Unicompartmental Femoral Implant

Referring to FIGS. 1-13 below, an exemplary patient-specific implant is illustrated, including references to the bone cuts made to implant the device. The implant is designed based on a medical image, such as a CT scan of a particular patient, and includes both a resurfacing component that attaches to the femoral condoyle of the patient and a tibial tray component that attaches to the top of the tibia as illustrated. When implanted, the unicompartmental resurfacing component and the tibial tray form an articular surface of the knee joint in the patient.

Such an implant can be designed and manufactured using traditional CAD-based design rules. However, in the present embodiment, it is designed using an automated system that, for example, partially automates the design process. The specifics attributes of such a system are more fully described below. Similarly, other devices, such as patient-specific instrumentation, other types of knee resurfacing devices, other types of knee joint replacement devices, and other orthopedic implants and instrumentation for other joints or other parts of the anatomy can be designed and manufactured using such partially or fully automated design and manufacturing processes.

Figure 1:
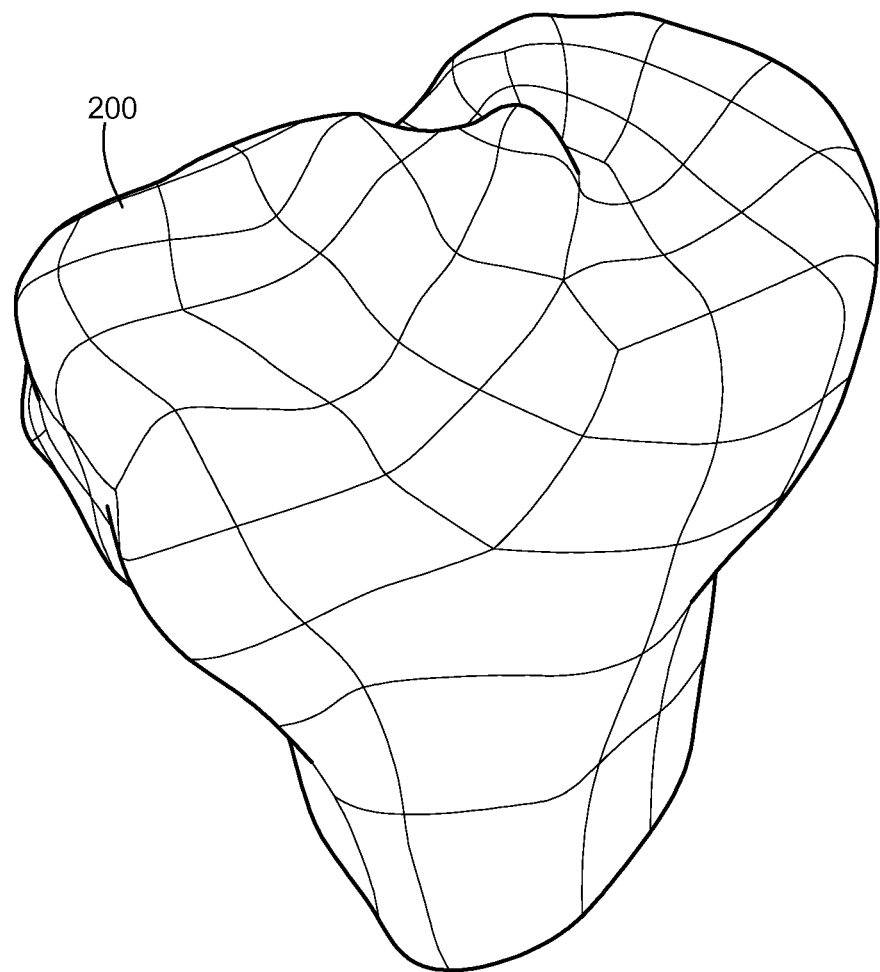
FIG. 1 is a graphic representation of a virtual model illustrating a front perspective view of a proximal portion of a tibia.

FIGS. 1-6 illustrate the design process for an exemplary tibial component of a patient-specific unicompartmental knee implant. The image data from the CT scan is transferred to the system and used to build a virtual model of the patient's anatomy. Referring to FIG. 1, the virtual model includes the tibial surface 200 of the patient, which is derived from the image data. An image of the surface of the tibia 200 can be generated from the virtual model and displayed on a computer screen during the design process.

Figure 2:
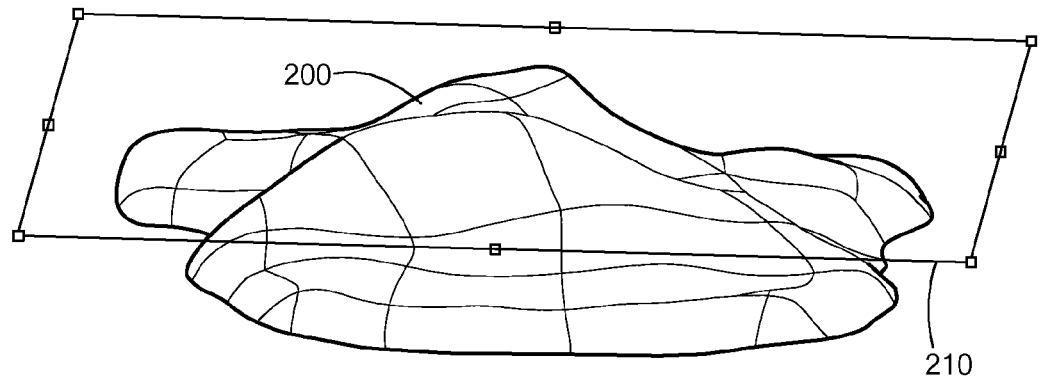
FIG. 2 is a graphic representation of a virtual model illustrating a front perspective view of a portion of the tibial bone of FIG. 1 to be removed along a cutting place.
Figure 3:
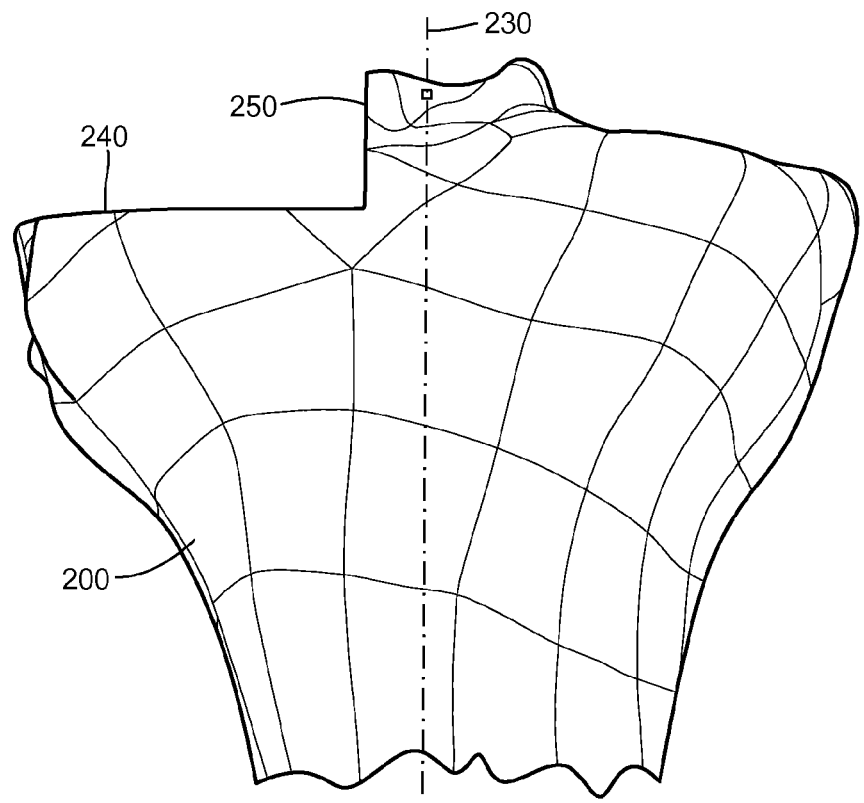
FIG. 3 is a graphic representation of a virtual model illustrating a front perspective view of the tibia of FIG. 1 with a portion of bone removed.
Figure 4:
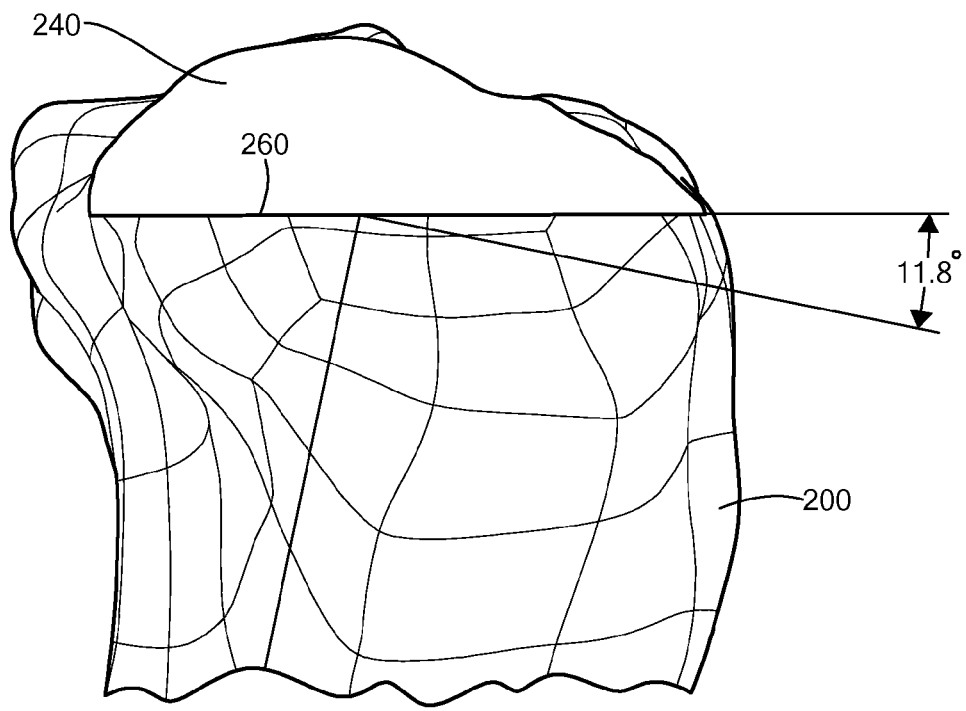
FIG. 4 is a graphic representation of a virtual model illustrating a side perspective view of the tibia of FIG. 3 with the portion of bone removed.

Referring also to FIG. 2, the tibial surface 200 can be used to define mathematically the natural slope of the patient's tibia. In this embodiment, the slope is graphically illustrated by a plane 210. Referring to FIG. 3, a horizontal cut is then designed. First, an anatomical axis 230 of the tibia is determined, and the positions of a horizontal cut 240 and vertical cut 250 are determined. In the coronal plane, the horizontal cut 240 preferably is perpendicular to the anatomical axis 230, but many other orientations and positions are possible. As shown in FIG. 4, with respect to the sagittal plane, the horizontal tibial cut 240 can be derived with respect to the patient's slope 260. Preferably, the cut 240 is approximately 11.5 degrees relative to the patient's existing tibial slope 250 in the sagittal plane.

Figure 5:
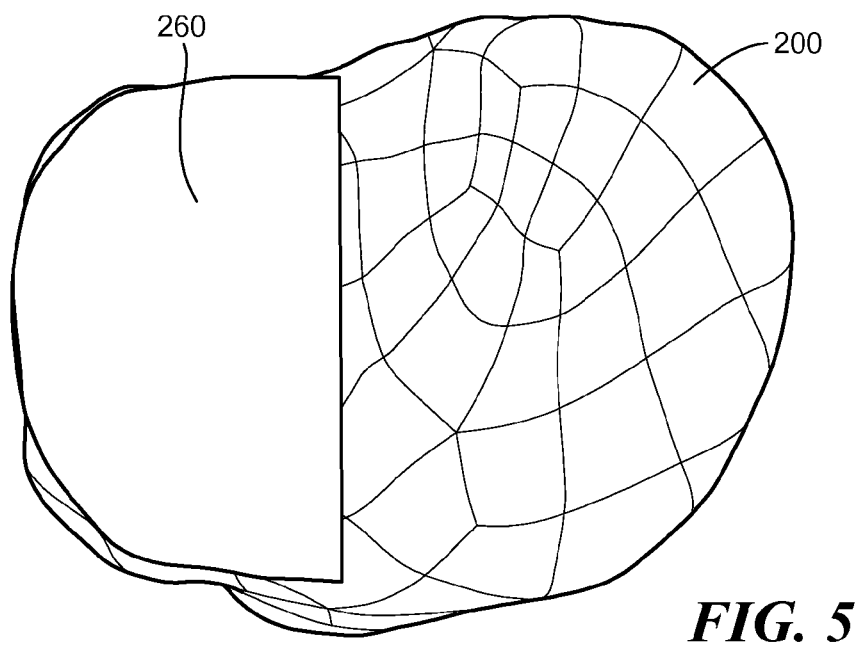
FIG. 5 is a graphic representation of a virtual model illustrating a top perspective view in an axial direction of the tibia of FIG. 3.
Figure 6:
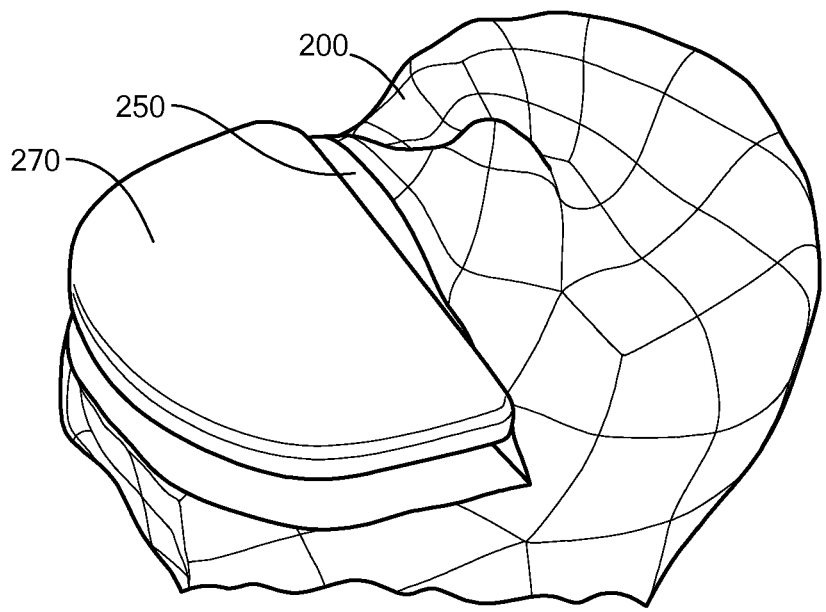
FIG. 6 is a graphic representation of a virtual model illustrating a top perspective view of the tibial of FIG. 3 and an implant placed where the portion of bone was removed.
Figure 7:
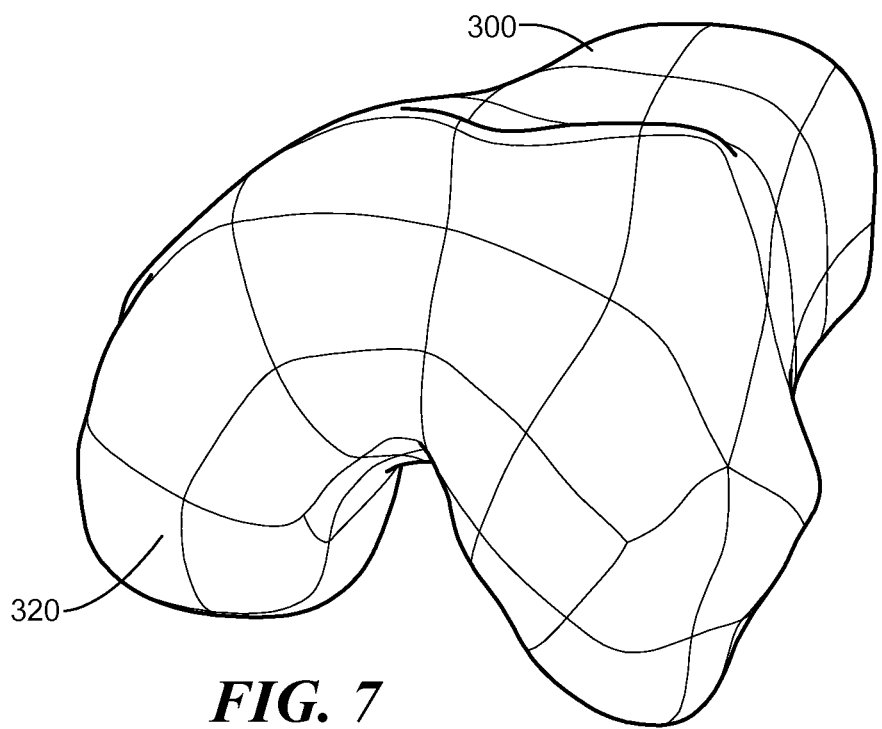
FIG. 7 is a graphic representation of a virtual model illustrating an end perspective view of a condyle portion of a femur.

Referring to FIGS. 5 and 6, the resulting cut leaves a shelf 260 upon which the tibial component 270 of a unicondylar knee implant will be placed. The tibial component 270 preferably is designed to maximize coverage of the tibial shelf 260. In some embodiments, a tibial component can be designed to exactly match a perimeter of the tibial shelf.

Figure 8:
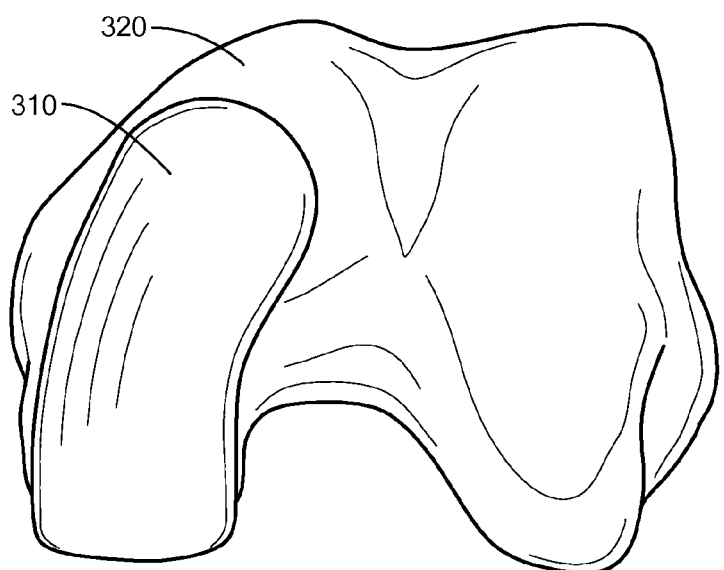
FIG. 8 is a graphic representation of a virtual model illustrating an end perspective view in an axial direction of the femur of FIG. 7 with an initial form of an implant placed on one of the condyles of the femur.

Referring to FIGS. 7-13, a femoral component of the patient-specific unicompartmental knee implant is also designed using automated design principles. As with the tibial, the surface 300 of the patient's femur is derived from the image data, including a virtual representation of the condyle 320 of the femur. Referring to FIG. 8, a coronal profile 310 of the implant can be superimposed on the condyle 320 of the femur to assess the orientation and sizing of the implant to be designed.

Figure 9:
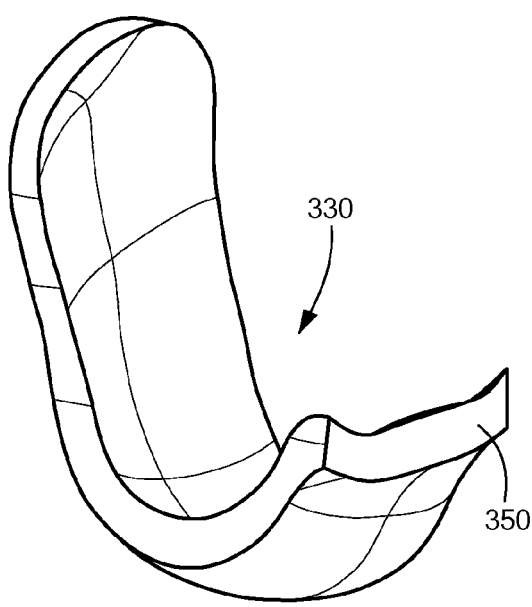
FIG. 9 is a graphic representation of a virtual model illustrating a side perspective view of the initial form of the implant of FIG. 8
Figure 10:
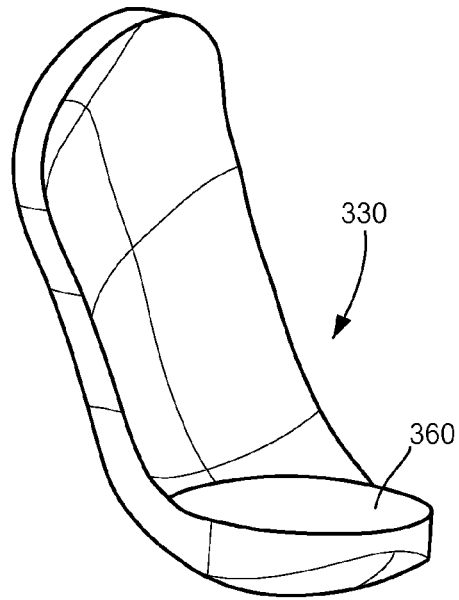
FIG. 10 is a graphic representation of a virtual model illustrating a side perspective view of the implant of FIG. 8 in a later stage of design.
Figure 11:
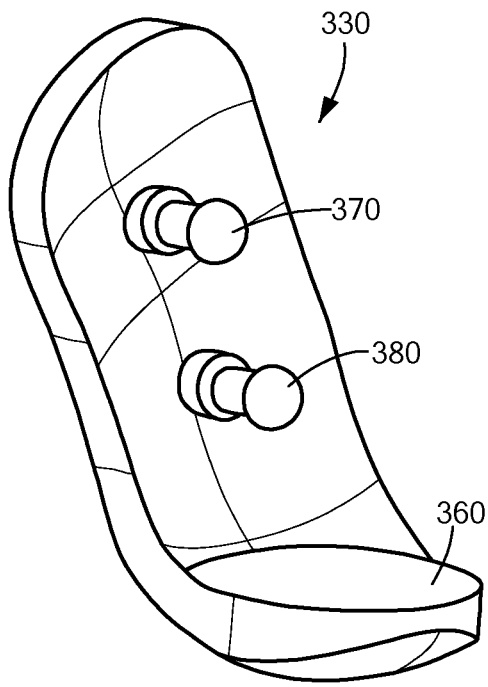
FIG. 11 is a graphic representation of a virtual model illustrating a side perspective view of the implant of FIG. 11 in a later stage of design.

As shown in FIGS. 9-10, a virtual interim implant 330 is used to design a posterior cut into the implant. The virtual interim implant 330 allows the system to optimize the placement of the posterior cut, and includes a posterior cut surface 350 to align the posterior cut on the virtual model of the condyle. Once the posterior bone cut surface 350 is properly positioned, a posterior tray 360 is filled in on the virtual implant and trimmed to optimize the design of the implant. As shown in FIG. 11, fixation pegs 370 and 380 can then be added. Preferably, the pegs 370 and 380 are positioned in a flexed position relative to the mechanical axis and/or the primary direction of the forces on the knee applied by the femur.

Figure 12:
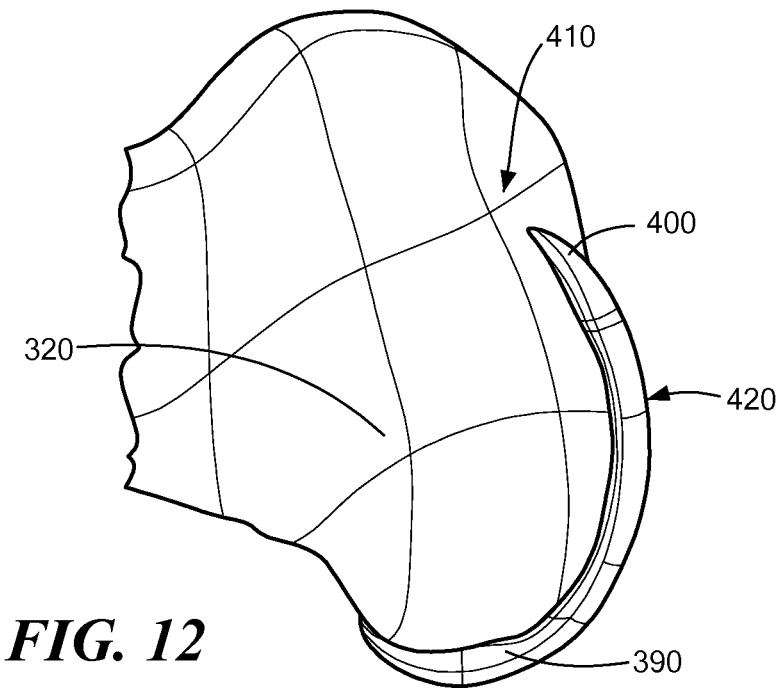
FIG. 12 is a graphic representation of a virtual model illustrating a side perspective view of the implant of FIG. 10 in a still later stage of design and attached to the femur of FIG. 7.

Referring to FIG. 12, the virtual model of the femoral component of the unicompartmental implant 390 is then fit to the virtual model of the condyle 320, and the proper orientation of the implant relative to the condyle is finalized. A tapering portion 400 is included in an anterior portion of the implant to provide a gradual transition from an articular surface 410 of the implant and an articular surface 420 of the implant.

Figure 13:
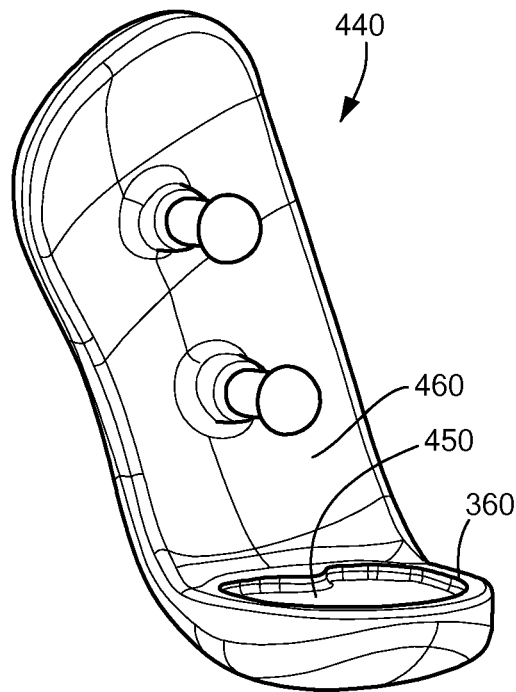
FIG. 13 is a graphic representation of a virtual model illustrating a side perspective view of the final design of the implant.

Referring to FIG. 13, a virtual model of the final femoral component 440 is created by position a cement pocket 450 in a bone-facing surface 460 of the posterior tray 360.

Automated Design of an Implant with a "Patient-Engineered" Articular Surface

Figure 14:
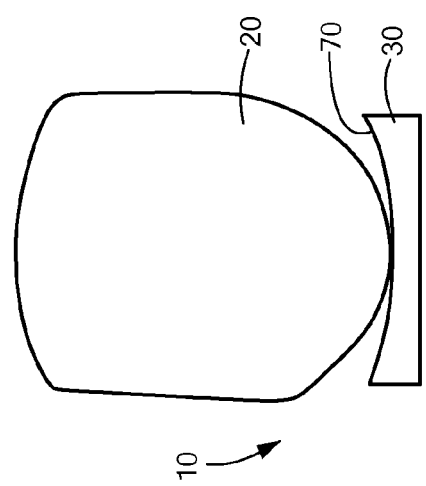
FIG. 14 is a schematic view of a unicompartmental implant.
Figure 15:
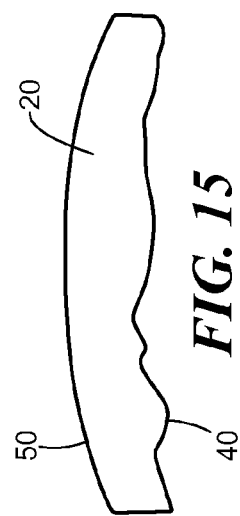
FIG. 15 is a cross-sectional schematic view in the coronal plane of a femoral component of the implant of FIG. 14.

Preferably, patient-specific implants include articular surface and other attributes that are engineered from the patient's own anatomy, but that provide an improved function. For example, an articular surface can create a healthy and variable "J" curve of the patient in the sagittal plane and a constant curvature in the coronal plane that is based on the patient's specific anatomy, but that does not seek to mimic or precisely recreate that anatomy, may be preferred. For example, referring to FIGS. 14-15, in another exemplary embodiment of a patient-specific device, a unicompartmental resurfacing implant has an enhanced articular surface that is engineered based on the specific anatomy of a patient. A unicompartmental implant 10 similar to the device in Example 1, having a femoral resurfacing component 20 and a tibial tray component 30, is designed based on patient-specific data. An inner, femoral-facing surface 40 of the resurfacing component 20 conforms to the corresponding surface of the femoral condoyle. However, the outer, articular surface 50 of the resurfacing component 20 is enhanced to incorporate a smooth surface having a nearly constant radius in the coronal plane. The corresponding articular surface 70 of the tibial tray 30 has a surface contour in the coronal plane that is matched to the outer articular surface 50. In this embodiment, the articular surface 70 has a radius that is five times the radius of outer articular surface 50.

Figure 16:
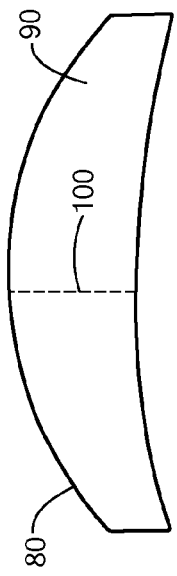
FIG. 16 is a cross-sectional schematic view in the coronal plane of an alternate embodiment of a femoral component of a unicompartmental implant.
Figure 17:
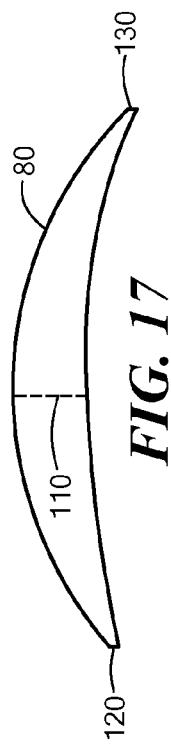
FIG. 17 is a cross-sectional schematic view in the coronal plane of an alternate embodiment of a femoral component of a unicompartmental implant.
Figure 18:
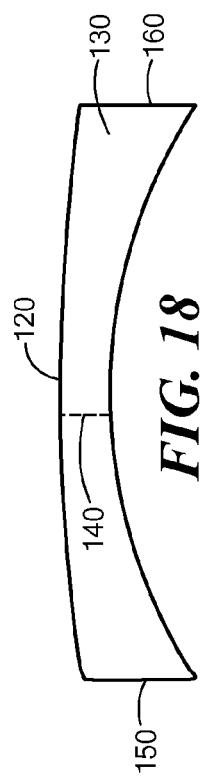
FIG. 18 is a cross-sectional schematic view in the coronal plane of an alternate embodiment of a femoral component of a unicompartmental implant.

The design of implant 10 has several advantages. First, the design of articular surface 50 allows the thickness of femoral component to be better controlled as desired. For example, referring to FIG. 16, if a curve of an articular surface 80 of a femoral component 90 is too large, the thickness of the femoral component may be too thick along a centerline 100 of the implant, thereby requiring an excessive amount of bone to be removed when the implant is placed on the femoral condoyle. On the other hand, referring to FIG. 17, if the same curve 80 is applied to a device having an appropriate centerline thickness 110, the margins or sidewalls 120 and 130 of the device may be too thin to provide proper structural support. Similarly, referring to FIG. 18, if the curve of the outer articular surface 120 of a femoral component 130 is too flat, the device will not exhibit the tapering from a centerline 140 to the margins or sidewalls 150 and 160 of the device and may not function well.

Referring again to FIGS. 14 and 15, a second advantage of the implant 10 over certain other embodiments of patient-specific devices is that the smooth articular surface 50 is thought to provide better kinematics than a true representation of the surface of the patient's femoral condoyle may provide.

Figure 19:
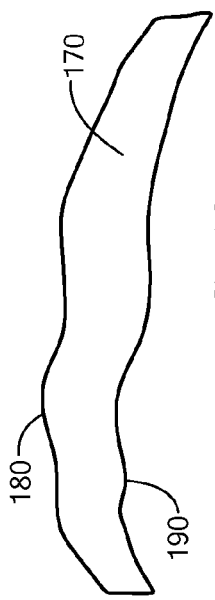
FIG. 19 is a cross-sectional schematic view in the coronal plane of an alternate embodiment of a femoral component of a unicompartmental implant.

For example, referring also to FIG. 19, one method of making patient specific implants is to use a simple offset, in which a femoral component 170 is designed using a standard offset from each point of the modeled surface of the patient's femoral condoyle. Using such a design, the thickness of the device will remain essentially constant, and an outer surface 180 will essentially match or conform to the underlying inner femoral-facing surface 190, as well as the modeled surface of the femoral condoyle on which it is based. While this provides a truly patient-matched outer surface, it is not necessarily optimal for the kinematics of the resulting implant, due to, for example, rough areas that may produce higher, more localized loading of the implant. By using a smooth surface with an essentially pre-determined shape, the loading of the implant can be better managed and distributed, thereby reducing the wear on the tibial tray component 30.

The third advantage, which is also related to the loading and overall kinematics of the implant, is in the matching of the tibial articular surface 70 to the femoral articular surface 50 in the coronal plane. By providing a radius that is predetermined, e.g., five times the radius of the femoral articular surface 50 at its centerline in the present embodiment, the loading of the articular surfaces can be further distributed. Thus, the overall function and movement of the implant is improved, as is the wear on the tibial tray, which is polyethylene in this embodiment. While the present embodiment uses a ratio of five times the radius of the outer surface at its centerline (note that the radius of the outer surface may be slightly different at other locations of the outer surface 50 away from the centerline), other embodiments are possible, including an outer tibial surface that, in the coronal plane, is based on other ratios of curvature, other curvatures, other functions or combinations of curves and/or functions at various points. Additionally, while the embodiments shown in FIGS. 16-19 are not considered to be optimal designs generally, they are embodiments that can be generated using automated systems and may have preferable characteristics in some instances.

An Exemplary Automated System for Designing Patient-Specific Implants

The implants described in both Examples 1 and 2 can be designed and manufactured using CAD-based design rules or other largely manual procedures, i.e., procedures that are either entirely manual, or that may contain certain automated components but that are still predominately manual in nature.

Alternatively, those implants, as well as essentially any type of patient-specific implant, can be designed and manufactured using an automated system that, for example, partially or fully automates the design process. Such an automated process is more fully described below. Similarly, other devices, such as patient-specific instrumentation, other types of knee resurfacing devices, other types of knee joint replacement devices, and other orthopedic implants and instrumentation for other joints or other parts of the anatomy can be designed and manufactured using such partially or fully automated design and manufacturing processes. In the following example, an embodiment of an automated process is described. This embodiment is one of many potential embodiments that may vary in many ways, each having its own specifications, design goals, advantages and tradeoffs.

Automated Design of a Femoral Component a. Sketching a Sulcus Line

Referring to FIGS. 20-31, a sulcus line can be sketched as a curve on a condylar surface of a femur before sketching a femoral implant contour. The sulcus point can be viewed more easily in a view other than a profile view. It is preferable to start sketching the sulcus line in a view where the sulcus point is easily visible and then change the view with each new segment, finally making the line visible in the profile view.

The automation system constructs the curve segment by segment, interpolating the sketch points by a local cubic spline. The spline does not lie on the surface, and typically will not be close to it. The curve will pass near the surface on the outside part of it to make it highly visible in any view. To do this, the spline segments are interpolated, and, for each intermediate point, a ray extending from an essentially infinitely distant point and perpendicular to the screen plane intersects with the surface. As the view can be different for each segment, the directions of projects may also be different for each segment.

When a new sketch point is added, the spline is changed only at its last created segment. But the sketch points and the directions of projection are kept until the curve construction is complete. This allows the system to reject as many segments as the system wants and redefine the spline until the system has developed a satisfactory shape using an iterative process.

The cubic spline is a local cubic spline with a special rule of defining tangent vectors of interpolating points. By way of example in this particular embodiment:

Suppose there are n+1 points p0, p1, . . . , pn.

For inner points (i=n−1), the system defines tangent vector as a bisect of a triangle formed by two neighbor chord vectors starting from the point:

$$v_0 = p_i - p_{i-1} \text{ incoming chord} \quad (a)$$

$$v_1 = p_{i+1} - p_i \text{ outgoing chord} \quad (b)$$

$$h_0 = |v_0| \text{ length of the incoming chord} \quad (c)$$

$h_1 = |v_1|$ length of the outgoing chord (d)

$m_i = \dfrac{h_1 * v_0 + h_0 * v_1}{h_0 + h_1}$ tangent at the inner point (e)

For the first and the last points the system define the tangent vector from the constraint of zero curvature at the end points:

$v_0 = p_1 - p_0$ first chord (f)

$m_i = \dfrac{3 * v_0 - m_1}{2}$ first tangent (g)

$v_{n-1} = p_n - p_{n-1}$ last chord (h)

$m_n = \dfrac{3 * v_{n-1} - m_{n-1}}{2}$ last tangent (i)

The interpolation inside each segment is done according a classic cubic segment formula:

$f0 = 1 - 3\mu^2 + 2\mu^3$ (j)

$f1 = 3\mu^2 - 2\mu^3$ (k)

$g0 = \mu^3 - 2\mu^2 + \mu$ (l)

$g1 = \mu 3 - \mu^2$ (m)

$pt = f_0 * pt_0 + g_0 * m_0 +$ (n)

$f_1 * pt_1 + g_1 * m_1$ (o)

When the system has sketched the sulcus line 520, it then begins to develop the curve of the shape of the implant. This is performed by an object that interpolates points lying close to the surface. In the present embodiment, the spline or the projection directions array is not used for this purpose, but many other implementations are possible. This curve serves as an indicator of approximate position where the femoral implant should stop.

b. Making Profile View

In the next phase of the design, a profile view is created. The system defines the profile view using the following steps:
  Set bottom view
  Rotate it 180 degrees around the z-axis
  Rotate it 15 degrees around x-axis
  Find common tangent to both condoyles in that view
  Change the view to make the common tangent horizontal
  Offer class for making additional rotations around x-axis and z-axis In the present embodiment, all steps except the last one are done automatically. (But, this step could also be automated.) Here, the user interface for making additional rotations is done using a UI class derived from CManager. The view can be rotated around x-axis and around z-axis either by moving the sliders or by setting the rotation angles in the toolbar edit boxes. This allows the designer to better view and examine the implant surfaces during the automated design process. When a designer, customer or other user clicks "Accept" in the toolbar, the system stores the entity of the view information in the document. The entity contains the view parameters and two correction angles.

c. Sketching Implant Contour

Figure 20:
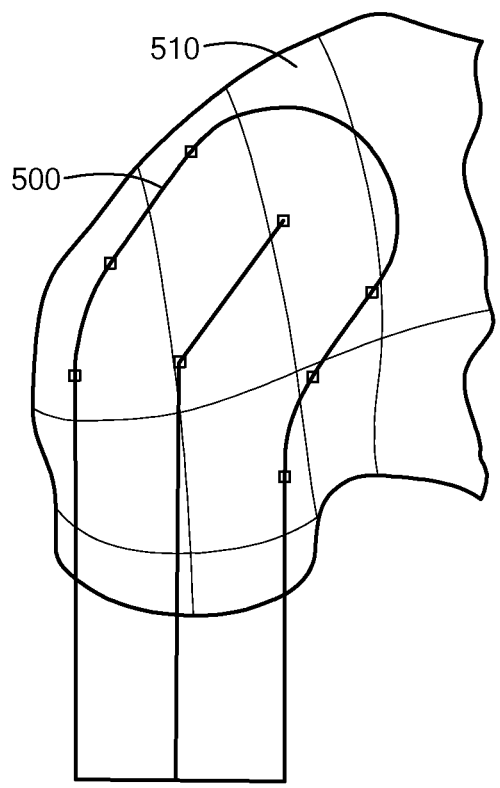
FIG. 20 is a graphic representation of a virtual model illustrating a side perspective view of a condyle of a femur having an implant contour on a profile plane superimposed.

Referring to FIG. 20, the profile view discussed above is used to sketch the implant. Designing the contour occurs in three steps:
  Sketch the original contour
  Preview the contour in 3d
  Modify the contour The second and third steps can be repeated until the contour shape is acceptable.

The initial implant contour 500 is sketched in the profile plane of condyle 510 of the femur of the patient. The contour is projected onto the femur surface orthogonally to the screen plane (profile plane). To close the contour on the posterior side, there are two points on the vertical edges of the contour which are the closest to a so-called 93 degrees plane. The system computes the cutting plane as the plane passing through those two points and forming minimal angle with 93 degrees plane. Making a cross-section by the cutting plane allows us to close the implant contour.

The two dimension contour to be projected on the femur surface consists of lines and arcs. There are two vertical lines, two slopped parallel lines, one horizontal line, two fillet arcs and two 90 degrees arcs on the top, forming one 180 degrees arc. Each of these arcs and lines is called a contour element; the contour consists of nine elements. The system also considers center-line elements, including two center lines and two points (shown as bold markers on the screen).

The members of this data structure are called "defining elements." The system can uniquely compute contour elements based on this information. When the software stores the profile contour in an external file, the software stores the defining elements. The defining elements can include those listed below in Table 1, but other embodiments are possible.

TABLE 1

Exemplary Defining Elements Used In Automated Design Process

| Defining Element | Definition |
|---|---|
| pt0, pt1, pt2 | ends of two center lines, from bottom to top |
| h1 | half distance between two vertical lines |
| h2 | half distance between two slopped lines |
| r0 and r1 | radii of fillet arcs |
| bFixedRad | Boolean flag |
| True | means preserving the radii during modification |
| False | re-compute the radii after modifications |

If the system wants to adjust fillets, the system sets a flag to true. The system then leaves the radii being to the original value and does not re-compute them automatically.

The initial sketching starts with indicating the upper point of the first vertical line. Then the system indicates the upper end of the first slopped line and makes the first fillet automatically. The last action in the initial sketching is indicating the upper point of the second slopped line—the rest of the contour can be uniquely defined automatically with the assumption that h1=h2. This condition can be changed during modification phase. After the initial sketch is complete, the contour is projected on the femur surface and is displayed.

In most cases the contour built after the initial sketch requires some modification, which can be automated using an iterative process that checks against a predefined set of rules and compares to a specification. Alternatively, a designer can intervene to check to progression of the automated design. To switch to modification phase, the user clicks a "Modify" button in the toolbar. When a user moves the mouse over some contour element, the element is highlighted by displaying in bold lines. The user can drag the element along the direction, associated with each element, by pressing left button, moving the mouse and releasing it in a new position. The whole contour will be rebuilt accordingly.

When the contour shape, which serves as the footprint and starting point of the implant, is satisfactory, the user clicks the button "Make" in the toolbar and the process of constructing the implant starts.

d. Making Implant

Constructing of the implant is done by the following main steps of the process:

Projecting the contour on femur surface
Making vertical sections
Computing posterior cutting plane
Making posterior section
Making the contour on femur surface
Making a center line
Making side lines
Approximating inner surface
Constructing an outer surface
Making the implant BREP
Marking inner and outer surfaces
Cutting by posterior cylinder
Flattening the cutting area
Filleting In the present embodiment, the process starts with projecting the sketched contour on the femur surface. This function does two things. First, it traverses all contour elements, computes 30 points on each of them and projects them onto femur BREP. Second, it takes two center line elements, extends the top one up to the top arcs, makes a fillet between the two lines and projects the resulted center line onto femur BREP. This is a first step in constructing the femur center line.

When the system projects contour and center line points onto the femur BREP, some points may miss the surface. This happens on a portion of a region where the contour elements are vertical lines. As the system constructs the contour on the femur in this area, the system will make cross-sections of the femur by those vertical lines. The system also finds the "lowest" (the closest to the 93 degrees plane) points on the side sections.

When the system calculates the two "lowest" points on the side sections, the system computes the cutting plane. It computes a temporary plane passing through the two lowest points perpendicular to the 93 degrees plane and then makes a cutting plane as passing through two lowest points perpendicular to the temporary plane. As the result, the cutting "profile" plane forms a minimal angle of 93 degrees from all planes passing through the two lowest points.

The next step is cutting the femur with the profile plane. The function finds a cross-section as an array of curves, discards the ones belonging to the other condoyle, approximates the best curve with a single spline and re-orients it so that it has the same direction at the starting lowest point as the projected contour.

The final step in making the contour on the femur is assembling all aspects together. This is done by a function that forms the contour from the main portion of the projection, i.e., the two segments of the vertical sections which start where the projection portion finishes and end at the "lowest" points, and the portion of the cutting plane cross-section.

Figure 21:
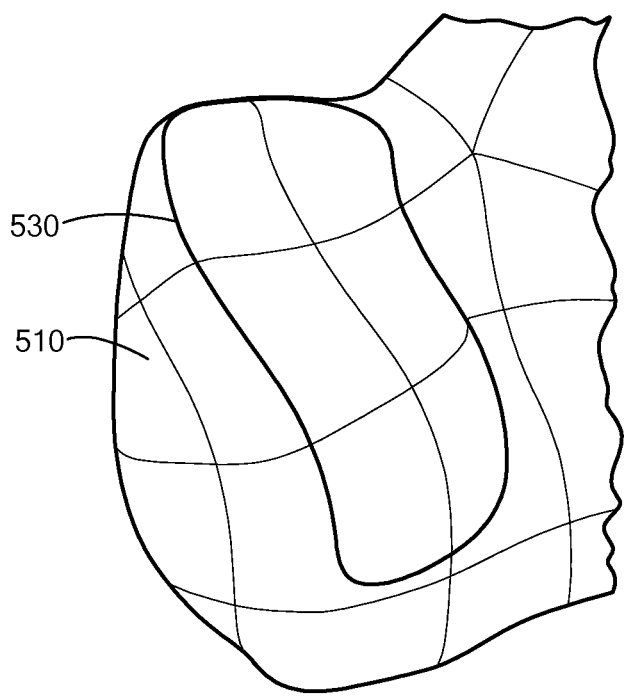
FIG. 21 is a graphic representation of a virtual model illustrating a side perspective view of the condyle of the femur of FIG. 20 having an implant contour superimposed on the femur surface.

FIG. 21 shows the resulting contour 530 superimposed on the condyle 510 of the femur. Now, when the system has the implant contour, it completes the center line. So far the system has the center line in the form of a point array on the femur from one end of the contour to the other. The function extends this array behind both ends along the corresponding cross-sections and approximates the resulted array with a relatively large tolerance (e.g., 0.5). A larger tolerance leads to a smoother outer-femoral curve, which is a design goal of the present embodiment (although other embodiments may have different implementations and/or design goals). However, while using a larger tolerance in the approximation make a smoother outer curve, but it may result in deviation from the vertical center line. To accommodate this phenomenon, a function is implemented that corrects the control points of the center line B-spline—adjusting them into the vertical line starting at some point.

Figure 22:
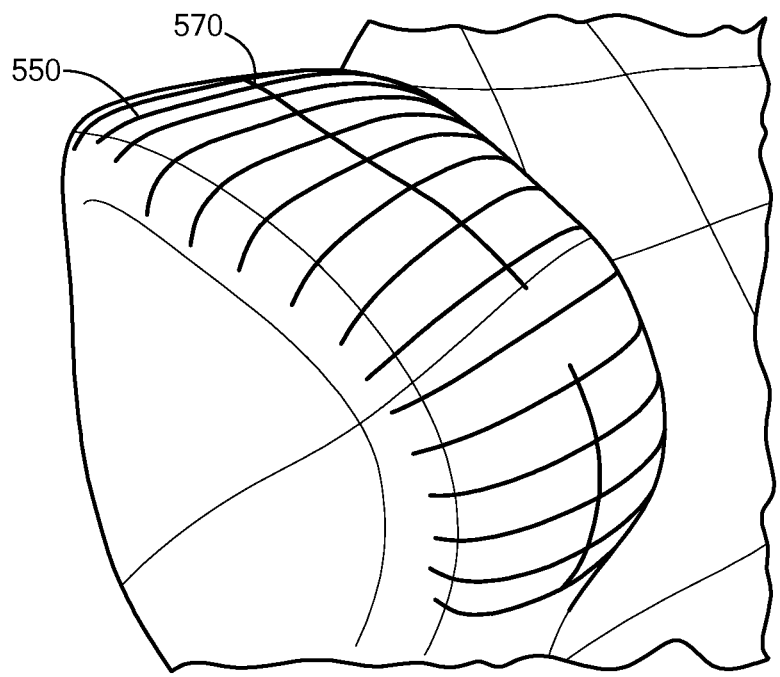
FIG. 22 is a graphic representation of a virtual model illustrating a side perspective view of the condyle of the femur of FIG. 20 having cross-sections of the condyle in an anterior taper zone of the implant superimposed.
Figure 23:
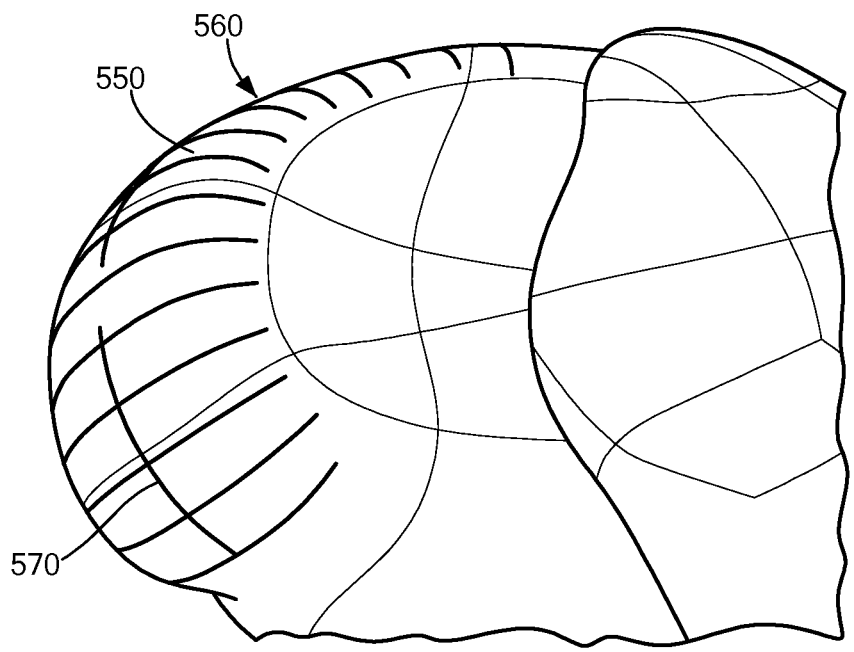
FIG. 23 is a graphic representation of a virtual model illustrating a side perspective view of the condyle of the femur of FIG. 20 showing an alternative view of the anterior taper zone shown in FIG. 22.

As shown in FIGS. 22-23, the system then computes the tapering arcs 550. Two functions compute the arcs 550 lying on the outer surface 560 of condyle 510. The arcs 550 are not connected to the center line 570, which passes closer to the inner surface of the implant being designed.

The system then computes the side rails of the implant by extending the side lines of the contour behind the end points to provide good intersection of the inner and outer surfaces with the cutting surfaces.

Figure 24A:
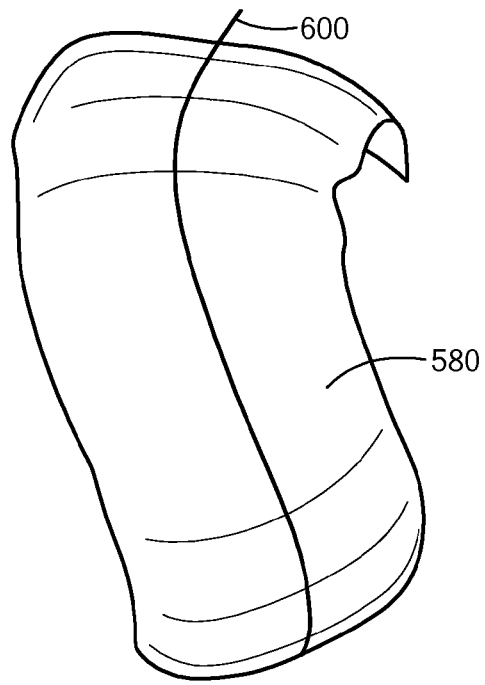
FIGS. 24A and 24B graphic representations of a virtual model illustrating a front and a side perspective view respectively of a surface of a condyle of FIG. 20 for use in designing an implant.
Figure 24B:
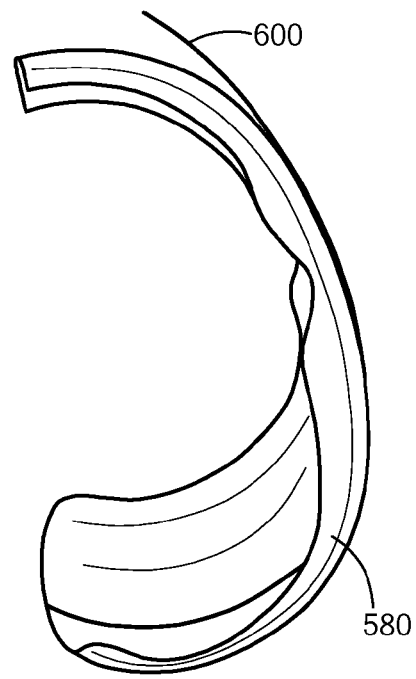
Figure 26:
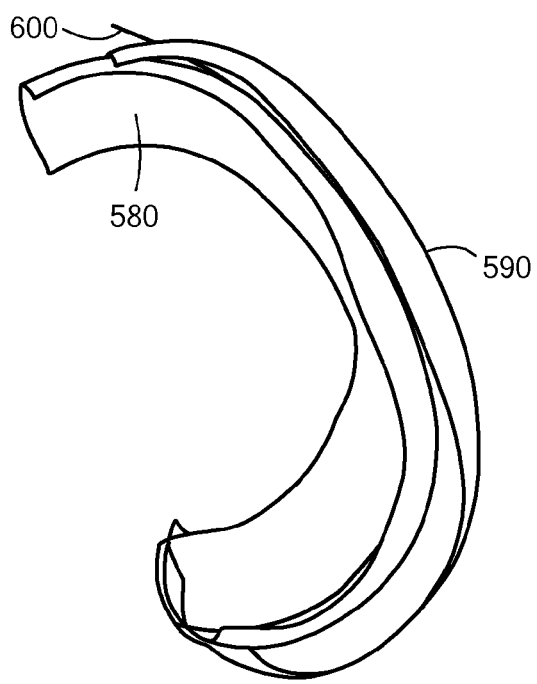
FIG. 26 is a graphic representation of a virtual model illustrating a side perspective view of inner and outer surfaces of an implant derived from the condyle of FIG. 20.

Referring also to FIGS. 24A and 24B and 26, the system then constructs the inner and outer surfaces 580 and 590. The inner surface 580 is constructed by a function that computes 15 points on the portion of a center line 600 between the end point of anterior taper and the end of the center line 570. For each of these points it makes a cross-section of the femur BREP by the plane, passing through the point and perpendicular to the center line. This cross-section is trimmed by the side rails, extended a little behind the side rails and added as single B-spline curve to the section array. Now, the system adds the cross-sections in the tapered zone. To do that, the system takes the first computed cross-section and creates additional sections. The system inserts the additional sections in the beginning of the section array.

Figure 25:
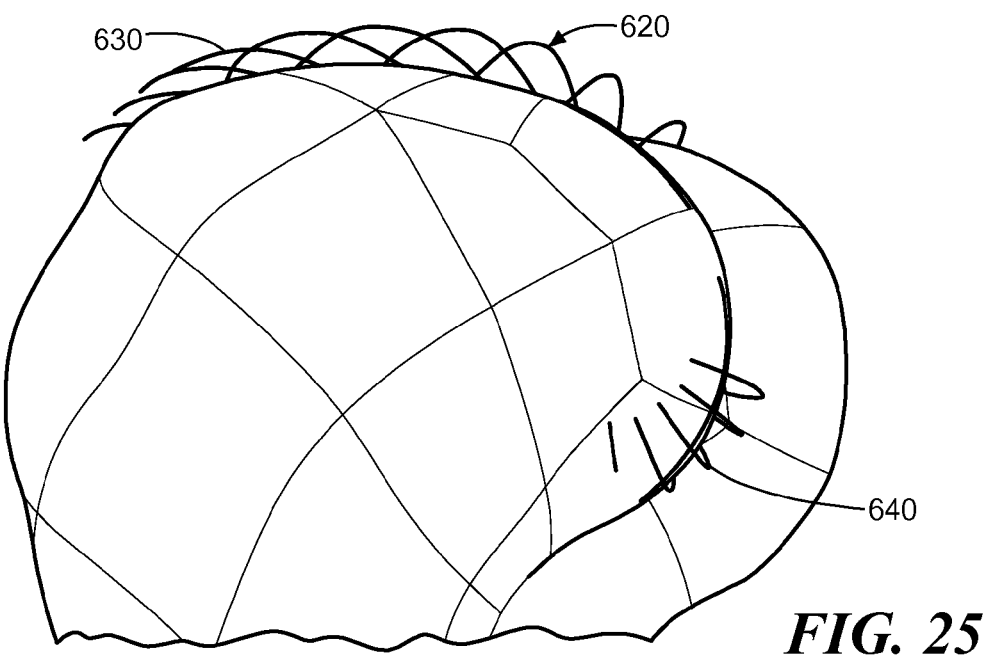
FIG. 25 is a graphic representation of a virtual model illustrating a side perspective view of the condyle of the femur of FIG. 20 having a set of arcs superimposed to loft an outer surface of an implant from the surface of the condyle.

Referring to FIGS. 25-26, the system then constructs a loft surface 620 using an array of cross-sections. A center line 630 and cross-sections 640 are used for making the outer surface 580 of the implant.

The outer surface 590 is constructed by sweeping an arc of the constant radius and angle along a center line trajectory. The trajectory is defined by the center line curve and an offset value. The ending portions of the trajectory are defined by the tapering arcs. The system function assumes that the arc radius and the offset value are given; for example, the system may use a radius=25.0 and offset=3.5.

The function then determines the angle of the sweeping arc. To find the angle, the system uses a heuristic approach. It computes several (e.g., 10) points on the center line in between tapering zones. For each of these points the system makes a plane perpendicular to the center line and find two points where the plane intersects with two side curves. Then the system computes the "center" by offsetting the point on the center line against the surface normal by a value equal the difference (radius—offset). The system then makes two lines from the center to the points on side curves and computes the angle between them. This angle approximates the possible sweeping arc angle at this cross-section. The system sets the angle of the sweeping arc to the maximum of those arcs angles.

Once the system determines the sweeping arc angle, it processes the anterior taper arc, the portion of the center line between taper zones, and the posterior taper arc. For taper arcs, the system computes an array of points on the curve and constructs an arc of the given radius and angle, lying in the plane perpendicular to the curve and having the calculated point as its middle point. The center line that the system processes is almost the same, except that the system offsets the point on the curve along the femur normal to the offset value. This results in a set of arcs as shown. Thus, the outer surface 590 is created as a loft surface using the set of created arcs as cross-sections.

Figure 27:
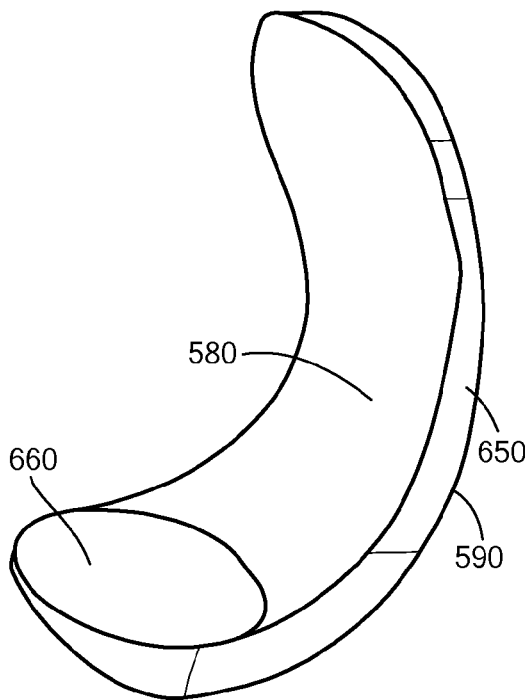
FIG. 27 is a graphic representation of a virtual model illustrating a side perspective view of an implant in an initial stage of design and having the inner and outer surfaces of FIG. 26.

Referring now to FIG. 27, after the system has designed the inner and the outer surfaces 580 and 590, it creates the side walls 650 of the implant. The system generates the side wall 650 by making two additional surfaces: a tabulated cylinder passing through the implant contour with an axis perpendicular to the profile plane, and a half of a regular cylinder with an axis perpendicular to the 93-degree plane.

Ideally, in this embodiment, the radius of the cylinder should be the half of the distance between the side lines, although other embodiments may employ different implementations. The implementation of this embodiment allows the cylinder to be tangential to the walls of the tabulated cylinder, and thus to create a smooth side surface.

The system then eliminates the angles of the side surfaces. The system can do this either by filleting the angles, or by using Boolean subtraction. Boolean operation will provide a more exact result, but risks instability in some cases. The system then flattens the posterior area 660 of the inner surface.

e. Measuring Thickness

Figure 28:
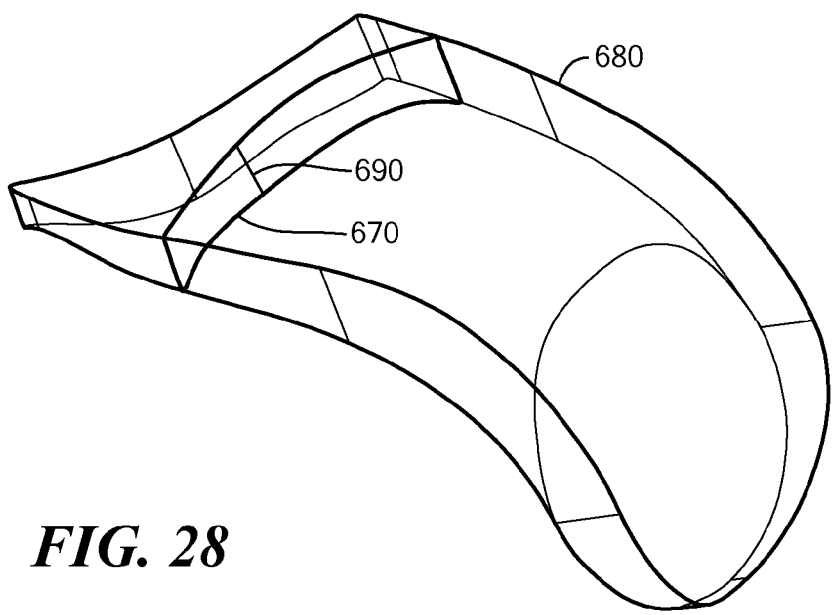
FIG. 28 is a graphic representation of a virtual model illustrating a side perspective view of an outline of the implant of FIG. 27 having a cross section noted by a lighter-colored line.

Referring to FIG. 28, the next step after the implant is created is controlling its thickness. With a sweeping arc radius that is small enough (e.g., 25 mm), the thickness may need to be altered in some portions. If the system keeps the thickness of the implant along the spine of the implant at about 3.5 mm, the thickness may be too small thickness along the edges. Generally, the thickness of the implant along the center line should be bigger than at the edges, but neither the center line nor the edges of the implant should get too thick or too thin. The design rules may result in such a condition, however, in the process of constructing other parts of the implant. Thus, the system checks the final thickness and makes adjustments to ensure the thickness meets the specifications of the implant.

In this embodiment, a functions to check the implant thickness is provided as a menu item that a user can select, but the feature could be automated to run automatically. As shown in FIG. 28, the menu item allows the system to move an implant cross-section 670 along a center line 690 and to move a line across that section and measure the distance between inner and outer surfaces along that line.

When the system begins to measure the implant thickness, it can display the implant in wireframe mode 680 and display the cross-section 670 in some initial position. The cross-section 670 is displayed, for example, in white, and the center-line 690 is displayed, for example, in red. The initial position of the cross-section is at the point on the center line 690 where anterior taper begins. The cross-line default position is in the middle of the cross-section 670.

f. Making Attachment Pegs

Figure 30:
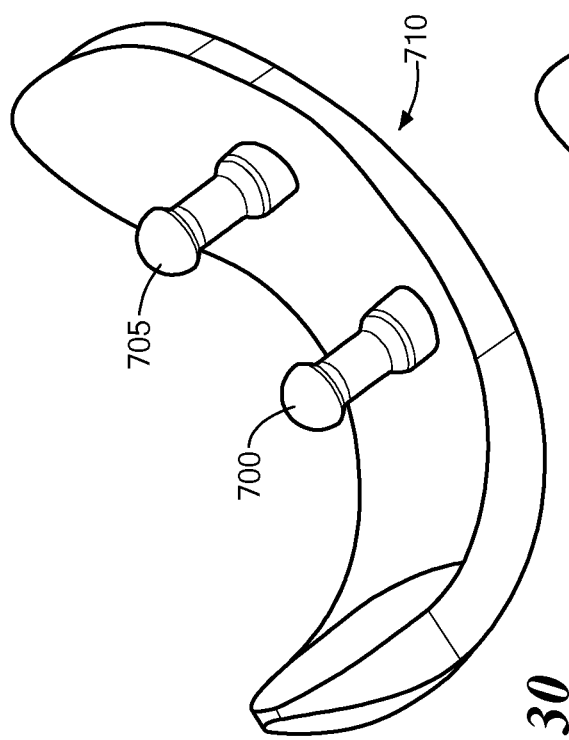
FIG. 30 is a graphic representation of a virtual model illustrating a side perspective view of the implant of FIG. 27 in a later stage of development with the pegs added.
Figure 29:
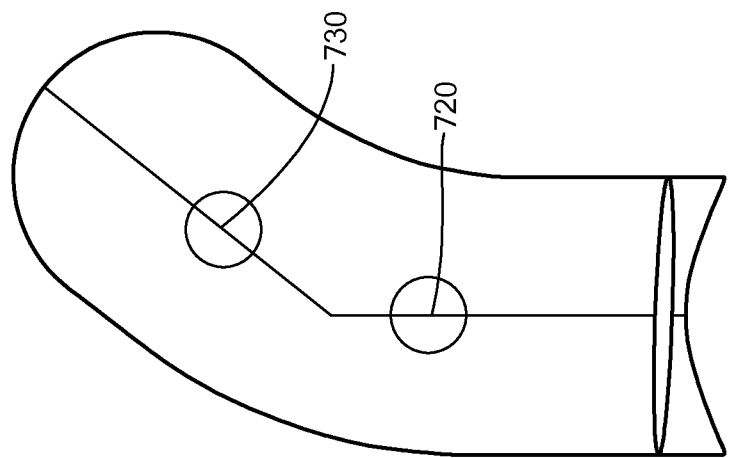
FIG. 29 is a graphic representation of a virtual model illustrating a bottom schematic view of the outline of FIG. 27 in a later stage of development during which pegs are added to the implant.

Referring to FIGS. 29 and 30, the system provides a function for positioning of pegs 700, 705 for attachment of the implant 710 to bone. The system allows a user to control the distances and the pegs heights, but these aspects could also be automated in other embodiments.

When started, the class displays the implant in the wireframe mode in the profile view and suggests default positions 720, 730 for the pegs, marked on the screen as circles:

The user can move the pegs by dragging them. The pegs are moved along the center lines keeping constant distance between them. The toolbar displays the distances between the cutting plane and the first peg (d1), between the two pegs (d2), and between the second peg and the apex point of the implant contour (d3). It also displays the pegs heights.

The pegs 700, 705 can be pre-viewed with dynamic view changing by clicking button Preview and made with filleting their intersection with the implant inner surface by clicking Accept.

The class automatically computes initial positions of the pegs, trying to make equal all three distances d1, d3, d3. The distance d2 should be integer number, so it is rounded to the nearest integer. The other two, d1, and d3, are updated accordingly. A user can set the distance d2 right in the toolbar; again, the other two distances will be updated.

The toolbar has a button "Constraints". Clicking on this button invokes a modal dialog with a set of conditions. It sets the minimum value for d1 (11), the min/max values for d2 (11-18) and the min/max values for pegs heights (11-12). If one (or more) of conditions is violated, the corresponding value is displayed in red and moving the pegs produces an alarm.

The system requires that the distances from pegs apex points to the profile plane be equal. Although many other embodiments are possible. For every position of the pegs, the system extends them up to a plane, parallel to the profile plane and measure their heights, h1 and h2. Then the system adjusts them so that (h1+h2)/2 becomes 11.5. This allows the system to place both of pegs in the range 11-12 and their heights differ from 11.5 the same distance.

g. Inserting a Cement Pocket

Figure 31:
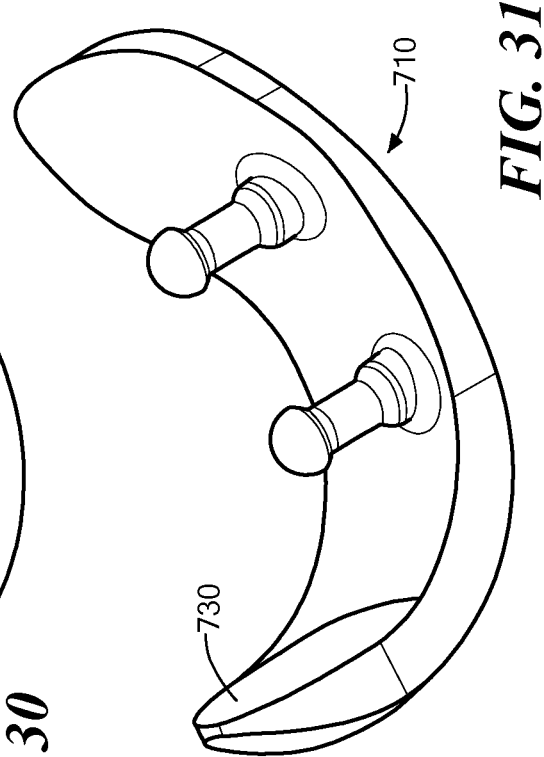
FIG. 31 is a graphic representation of a virtual model illustrating a side perspective view of the implant of FIG. 30 in final form and with fillets added around the pegs.

Referring to FIG. 31, a cement pocket 740 is then placed in the posterior section of the implant 710 as shown below.

The embodiments disclosed herein are exemplary only, and one skilled in the art will realize that many other embodiments are possible, including, without limitation, many variations on the embodiments described above as well as other entirely different applications of automated systems for designing patient specific implants of various types and for various joints and other parts of a patient's anatomy. The embodiments described herein are not intended to limit the scope of the claims.

What is claimed is:

1. A method of designing a patient-specific implant using a computer system for repairing a diseased or damaged knee joint of a patient, comprising:
   obtaining image data of at least a portion of the patient's knee joint including a femoral condyle;
   creating a virtual model of at least a portion of the femoral condyle from the image data; processing the virtual model to design a patient-specific implant based at least in part on the virtual model,
   wherein the patient-specific implant includes one or more planar bone-facing portions, and
   wherein at least a portion of the femoral condyle portion of the implant is adapted based on a dimension of the femoral condyle.

2. The method of claim 1, wherein processing the virtual model is automated without human intervention.

3. The method of claim 1, further comprising checking the design to determine whether the parameters of the design meet predetermined specifications.

4. The method of claim 1, wherein the virtual model is processed predominately without human intervention.

5. The method of claim 1, wherein the step of processing further comprises identifying anatomic landmarks to generate an implant design.

6. The method of claim 5, wherein identifying anatomic landmarks includes locating maxima or minima on the curvature of a surface portion of the virtual model.

7. The method of claim 1, wherein the step of process further comprises: identifying anatomic landmarks; and merging information regarding the anatomic landmarks with a generic model to create an implant design.

8. The method of claim 4, further comprising automatically determining an optimal viewpoint to allow a user to perform a design step.

9. The method of claim 1, further comprising combining a virtual template with the virtual model to design the patient-specific implant.

10. The method of claim 9, wherein the template may be adjusted by a user.

11. The method of claim 9, wherein the template is three dimensional.

12. The method of claim 1, wherein the one or more planar bone-facing portions are configured to accommodate one or more corresponding bone cuts of the femoral condyle.

13. The method of claim 12, wherein the position of each bone cut is automatically determined.

14. The method of claim 12, wherein the position of each bone cut is automatically determined using anatomical landmarks.

15. The method of claim 1, wherein the computer system is configured to automatically design attachment features.

16. The method of claim 15, wherein the attachment features are at least one of pegs and anchors.

17. The method of claim 1, wherein the coronal curvature of the femoral condyle portion of the patient-specific implant is constant.

18. The method of claim 1, wherein the coronal curvature of the femoral condyle portion of the patient-specific implant is derived from the patient's image data.

19. The method of claim 12, wherein the position of at least one bone cut is automatically determined.

20. The method of claim 12, wherein the position of at least one bone cut is automatically determined using anatomical landmarks.

21. A method of designing a patient-specific implant using a computer system for repairing a diseased or damaged knee joint of a patient, comprising:
   obtaining image data of the diseased or damaged knee joint including a femoral condyle;
   creating a virtual model of at least a portion of the femoral condyle from the image data;
   processing the virtual model to design a patient-specific implant based at least in part on the virtual model in two or more planes,
   wherein the patient-specific implant includes one or more planar bone-facing portions, and
   wherein at least a portion of a sagittal curvature of the femoral condyle portion of the implant is adapted based on a shape of the femoral condyle in two or more dimensions.

22. The method of claim 21, further comprising producing the patient-specific implant from the design.

23. The method of claim 21, wherein the step of processes further comprises: identifying anatomic landmarks; and merging information regarding the anatomic landmarks with a generic model containing to create an instrument design.

24. The method of claim 21, wherein the coronal curvature of the femoral condyle portion of the patient-specific implant is constant.

25. The method of claim 21, wherein the coronal curvature of the femoral condyle portion of the patient-specific implant is derived from the patient's image data.

26. The method of claim 21, wherein the one or more planar bone-facing portions are configured to accommodate one or more corresponding bone cuts of the femoral condyle.

27. The method of claim 26, wherein the position of at least one bone cut is automatically determined.

28. The method of claim 26, wherein the position of at least one bone cut is automatically determined using anatomical landmarks.

* * * * *